US009611286B2

(12) United States Patent
Pamplona et al.

(10) Patent No.: US 9,611,286 B2
(45) Date of Patent: Apr. 4, 2017

(54) RUTHENIUM CARBON MONOXIDE RELEASING MOLECULES AND USES THEREOF

(71) Applicant: Alfama, Inc., Cambridge, MA (US)

(72) Inventors: Ana Pamplona, Lisbon (PT); Gonçalo J. L. Bernardes, Torres Vedras (PT); Maria M. Mota, Lisbon (PT); Carlos C. Romão, Cascais (PT)

(73) Assignee: Alfama, Inc., Cambridge, MA (US)

( * ) Notice: Subject to any disclaimer, the term of this patent is extended or adjusted under 35 U.S.C. 154(b) by 0 days.

(21) Appl. No.: 14/711,113

(22) Filed: May 13, 2015

(65) Prior Publication Data

US 2015/0322105 A1  Nov. 12, 2015
US 2016/0237105 A9  Aug. 18, 2016

Related U.S. Application Data

(63) Continuation of application No. 14/234,024, filed as application No. PCT/US2012/047661 on Jul. 20, 2012, now Pat. No. 9,062,089.

(60) Provisional application No. 61/510,136, filed on Jul. 21, 2011.

(51) Int. Cl.
*A61K 31/7135* (2006.01)
*C07H 5/10* (2006.01)
*C07H 5/08* (2006.01)
*C07F 15/00* (2006.01)
*A61K 45/06* (2006.01)
*C07H 23/00* (2006.01)

(52) U.S. Cl.
CPC ........... *C07H 5/10* (2013.01); *A61K 31/7135* (2013.01); *A61K 45/06* (2013.01); *C07F 15/0046* (2013.01); *C07H 5/08* (2013.01); *C07H 23/00* (2013.01)

(58) Field of Classification Search
None
See application file for complete search history.

(56) References Cited

U.S. PATENT DOCUMENTS

| | | |
|---|---|---|
| 2,870,180 A | 1/1959 | Kozikowski et al. |
| 3,065,250 A | 11/1962 | Levering |
| 3,278,570 A | 10/1966 | Wilkinson et al. |
| 3,694,232 A | 9/1972 | Hall et al. |
| 3,812,166 A | 5/1974 | Wiechert |
| 3,829,504 A | 8/1974 | Hall et al. |
| 3,980,583 A | 9/1976 | Mitchell et al. |
| 4,189,487 A | 2/1980 | Klosa |
| 4,312,989 A | 1/1982 | Spielvogel et al. |
| 4,322,411 A | 3/1982 | Vinegar et al. |
| 4,535,167 A | 8/1985 | Freidinger |
| 4,613,621 A | 9/1986 | Horrmann |
| 4,649,151 A | 3/1987 | Dougherty et al. |
| 4,657,902 A | 4/1987 | Kappas et al. |
| 4,668,670 A | 5/1987 | Ridoeout et al. |
| 4,699,903 A | 10/1987 | Ridoeout et al. |
| 4,709,083 A | 11/1987 | Spielvogel |
| 4,792,452 A | 12/1988 | Howard et al. |
| 4,910,211 A | 3/1990 | Imamura et al. |
| 4,938,949 A | 7/1990 | Borch et al. |
| 5,010,073 A | 4/1991 | Kappas et al. |
| 5,086,060 A | 2/1992 | Haley et al. |
| 5,102,670 A | 4/1992 | Abraham et al. |
| 5,254,706 A | 10/1993 | Spielvogel et al. |
| 5,312,816 A | 5/1994 | Spielvogel et al. |

(Continued)

FOREIGN PATENT DOCUMENTS

DE   4014762 A1   11/1991
DE   44 21 433    6/1995

(Continued)

OTHER PUBLICATIONS

[No Author Listed] "supramolecule" IUPAC compendium of chemical terminology. 2nd Edition. 1997. Retrieved from the internet at www.iupac.org/goldbook/SO6153.pdf on May 8, 2006.
[No Author Listed] Biosis Chem Abstracts Database. Accession No. PREV200600414130. 2005. Otterbein et al., Cell Mol Biol (Noisy-le-grand). Oct. 3, 2005;51(5):433-40. Abstract.
[No Author Listed] Chemical Abstracts. 2002;137:119662. (FR2816212).
[No Author Listed] Chemical Abstracts. 2004;140:400075. (WO2004/043341).
[No Author Listed] Chemical Abstracts. 2004;141:270758. (Ryter et al.).
[No Author Listed] Chemical Abstracts. 2004;142:211995. (Stein et al.).

(Continued)

*Primary Examiner* — Traviss C McIntosh, III
(74) *Attorney, Agent, or Firm* — Wolf, Greenfield & Sacks, P.C.

(57) ABSTRACT

The present invention provides novel ruthenium compounds of Formula (I):

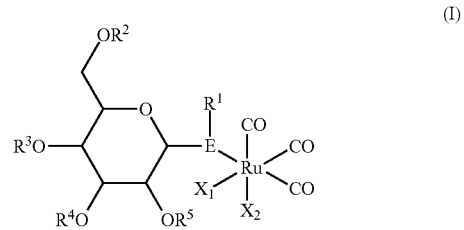

or salts, isomers, hydrates, or solvates thereof, or combinations thereof; wherein E, $R^1$, $R^2$, $R^3$, $R^4$, $R^5$, $X_1$, and $X_2$ are as defined herein, and pharmaceutical compositions thereof. Also provided are methods of use and treatment. Such compounds have been found useful in the treatment of malaria infection. Such compounds may also be useful in the treatment of inflammatory conditions, such as acute lung injury and acute resipiratory distress syndrome, which optionally may be associated with a malaria infection.

18 Claims, 19 Drawing Sheets

(56) References Cited

U.S. PATENT DOCUMENTS

| | | |
|---|---|---|
| 5,350,767 A | 9/1994 | Hallberg et al. |
| 5,447,939 A | 9/1995 | Glasky et al. |
| 5,621,000 A | 4/1997 | Arena et al. |
| 5,631,284 A | 5/1997 | Legzdins et al. |
| 5,659,027 A | 8/1997 | Spielvogel et al. |
| 5,664,563 A | 9/1997 | Schroeder et al. |
| 5,670,664 A | 9/1997 | Kao et al. |
| 5,700,947 A | 12/1997 | Soldato |
| 5,756,492 A | 5/1998 | Buelow et al. |
| 5,767,157 A | 6/1998 | Van Moerkerken |
| 5,801,184 A | 9/1998 | Glasky et al. |
| 5,811,463 A | 9/1998 | Legzdins et al. |
| 5,824,673 A | 10/1998 | Abrams et al. |
| 5,861,426 A | 1/1999 | del Soldato et al. |
| 5,882,674 A | 3/1999 | Herrmann et al. |
| 5,885,621 A | 3/1999 | Head et al. |
| 5,888,982 A | 3/1999 | Perrella et al. |
| 5,891,689 A | 4/1999 | Takle et al. |
| 6,025,376 A | 2/2000 | Laurent et al. |
| 6,025,394 A | 2/2000 | Menander et al. |
| 6,027,936 A | 2/2000 | Glasky et al. |
| 6,040,341 A | 3/2000 | del Soldato et al. |
| 6,051,576 A | 4/2000 | Ashton et al. |
| 6,060,467 A | 5/2000 | Buelow et al. |
| 6,066,333 A | 5/2000 | Willis et al. |
| 6,177,471 B1 | 1/2001 | Menander et al. |
| 6,203,991 B1 | 3/2001 | Nabel et al. |
| 6,211,233 B1 | 4/2001 | del Soldato |
| 6,218,417 B1 | 4/2001 | del Soldato |
| 6,242,432 B1 | 6/2001 | del Soldato |
| 6,251,927 B1 | 6/2001 | Lai et al. |
| 6,284,752 B1 | 9/2001 | Abrams et al. |
| 6,331,564 B1 | 12/2001 | Brugnara et al. |
| 6,338,963 B1 | 1/2002 | Glasky et al. |
| 6,344,178 B1 | 2/2002 | Alberto et al. |
| 6,350,752 B1 | 2/2002 | Glasky et al. |
| 6,417,182 B1 | 7/2002 | Abrams et al. |
| 6,518,269 B1 | 2/2003 | Camden et al. |
| 6,645,938 B2 | 11/2003 | Oeltgen et al. |
| 6,673,908 B1 | 1/2004 | Stanton |
| 7,011,854 B2 | 3/2006 | Haas et al. |
| 7,045,140 B2 | 5/2006 | Motterlini et al. |
| 7,053,242 B1 | 5/2006 | Alberto et al. |
| 7,569,214 B2 | 8/2009 | Kozlowski |
| 7,964,220 B2 | 6/2011 | Haas et al. |
| 7,968,605 B2 | 6/2011 | de Matos et al. |
| 7,989,650 B2 | 8/2011 | Motterlini et al. |
| 8,236,339 B2 | 8/2012 | Motterlini et al. |
| 8,389,572 B2 | 3/2013 | Motterlini et al. |
| 9,023,402 B2 | 5/2015 | Haas et al. |
| 9,062,089 B2 * | 6/2015 | Pamplona ............... C07H 5/08 |
| 9,163,044 B2 | 10/2015 | Blattler et al. |
| 2002/0043595 A1 | 4/2002 | Bridgers et al. |
| 2002/0045611 A1 | 4/2002 | Abrams et al. |
| 2002/0049190 A1 | 4/2002 | Bridger et al. |
| 2002/0155166 A1 | 10/2002 | Choi et al. |
| 2002/0165242 A1 | 11/2002 | Glasky et al. |
| 2002/0193363 A1 | 12/2002 | Bridger et al. |
| 2003/0039638 A1 | 2/2003 | Bach et al. |
| 2003/0064114 A1 | 4/2003 | Motterlini et al. |
| 2003/0068387 A1 | 4/2003 | Buelow et al. |
| 2003/0124157 A1 | 7/2003 | Engles et al. |
| 2003/0157154 A1 | 8/2003 | Fuller et al. |
| 2003/0207786 A1 | 11/2003 | Miracle et al. |
| 2003/0219496 A1 | 11/2003 | Otterbein et al. |
| 2003/0219497 A1 | 11/2003 | Otterbein et al. |
| 2004/0052866 A1 | 3/2004 | Otterbein et al. |
| 2004/0067261 A1 | 4/2004 | Haas et al. |
| 2004/0122091 A1 | 6/2004 | Dasseux et al. |
| 2004/0131602 A1 | 7/2004 | Buelow et al. |
| 2004/0131703 A1 | 7/2004 | Bach et al. |
| 2004/0143025 A1 | 7/2004 | Buelow et al. |
| 2004/0214900 A1 | 10/2004 | Forbes et al. |
| 2004/0228930 A1 | 11/2004 | Billiar et al. |
| 2004/0258772 A1 | 12/2004 | Otterbein et al. |
| 2005/0048133 A1 | 3/2005 | Pinksy et al. |
| 2005/0175555 A1 | 8/2005 | Stradi et al. |
| 2006/0115542 A1 | 6/2006 | Motterlini et al. |
| 2006/0127501 A1 | 6/2006 | Motterlini et al. |
| 2006/0147548 A1 | 7/2006 | Motterlini et al. |
| 2006/0148900 A1 | 7/2006 | Haas et al. |
| 2006/0233890 A1 | 10/2006 | Haas et al. |
| 2007/0049640 A1 | 3/2007 | Pavliv |
| 2007/0065485 A1 | 3/2007 | Motterlini et al. |
| 2007/0207217 A1 | 9/2007 | Haas et al. |
| 2007/0207993 A1 | 9/2007 | Haas et al. |
| 2007/0219120 A1 | 9/2007 | de Matos et al. |
| 2008/0026984 A1 | 1/2008 | de Matos et al. |
| 2010/0105770 A1 | 4/2010 | Motterlini et al. |
| 2010/0196516 A1 | 8/2010 | Nobre |
| 2011/0015263 A1 | 1/2011 | Motterlini et al. |
| 2011/0038955 A1 | 2/2011 | Rodrigues et al. |
| 2011/0237546 A1 | 9/2011 | Haas et al. |
| 2014/0142176 A1 | 5/2014 | Blattler et al. |
| 2014/0212514 A1 | 7/2014 | Rodrigues et al. |
| 2014/0219996 A1 | 8/2014 | Pamplona et al. |
| 2016/0137679 A1 | 5/2016 | Blättler et al. |

FOREIGN PATENT DOCUMENTS

| | | |
|---|---|---|
| EP | 0 034 238 | 8/1981 |
| EP | 0 076 493 | 4/1983 |
| EP | 0 181 721 | 5/1986 |
| EP | 0 632 026 | 1/1995 |
| FR | 2816212 | 5/2002 |
| GB | 1107510 | 6/1965 |
| GB | 0111872.8 | 7/2001 |
| GB | 0227135.1 | 12/2002 |
| GB | 0227138.5 | 12/2002 |
| GB | 2395431 | 5/2004 |
| GB | 2395432 A | 5/2004 |
| HU | 57595 | 12/1991 |
| HU | 211 084 | 10/1995 |
| WO | WO 85/04326 A1 | 10/1985 |
| WO | WO 91/01128 | 2/1991 |
| WO | WO 91/01301 | 2/1991 |
| WO | WO 92/03402 | 3/1992 |
| WO | WO 92/04905 | 4/1992 |
| WO | WO 93/05795 | 4/1993 |
| WO | WO 94/01413 | 1/1994 |
| WO | WO 94/22482 | 10/1994 |
| WO | WO 95/05814 | 3/1995 |
| WO | WO 95/09831 | 4/1995 |
| WO | WO 95/35105 A1 | 12/1995 |
| WO | WO 96/03125 | 2/1996 |
| WO | WO 96/09038 | 3/1996 |
| WO | WO 97/16405 | 5/1997 |
| WO | WO 97/36615 | 10/1997 |
| WO | WO 97/37644 | 10/1997 |
| WO | WO 98/09618 | 3/1998 |
| WO | WO 98/13058 A1 | 4/1998 |
| WO | WO 98/29115 | 7/1998 |
| WO | WO 98/38179 | 9/1998 |
| WO | WO 98/48848 | 11/1998 |
| WO | WO 99/67231 | 12/1999 |
| WO | WO 00/10613 | 3/2000 |
| WO | WO 00/21965 A1 | 4/2000 |
| WO | WO 00/36113 | 6/2000 |
| WO | WO 00/56145 | 9/2000 |
| WO | WO 00/56743 | 9/2000 |
| WO | WO 00/61537 | 10/2000 |
| WO | WO 01/12584 | 2/2001 |
| WO | WO 01/16359 | 3/2001 |
| WO | WO 01/25243 | 4/2001 |
| WO | WO 01/28545 | 4/2001 |
| WO | WO 02/078684 | 10/2002 |
| WO | WO 02/080923 | 10/2002 |
| WO | WO 02/092072 | 11/2002 |
| WO | WO 02/092075 A2 | 11/2002 |
| WO | WO 03/000114 | 1/2003 |
| WO | WO 03/066067 | 8/2003 |
| WO | WO 03/067598 | 8/2003 |
| WO | WO 03/072024 | 9/2003 |
| WO | WO 03/082850 A2 | 10/2003 |

(56) References Cited

FOREIGN PATENT DOCUMENTS

| | | |
|---|---|---|
| WO | WO 03/088923 | 10/2003 |
| WO | WO 03/088981 | 10/2003 |
| WO | WO 03/094932 | 11/2003 |
| WO | WO 03/096977 | 11/2003 |
| WO | WO 03/103585 | 12/2003 |
| WO | WO 2004/029033 | 4/2004 |
| WO | WO 2004/043341 | 5/2004 |
| WO | WO 2004/045598 | 6/2004 |
| WO | WO 2004/045599 | 6/2004 |
| WO | WO 2004/080420 | 9/2004 |
| WO | WO 2005/013691 A1 | 2/2005 |
| WO | WO 2005/090400 | 9/2005 |
| WO | WO 2006/012215 | 2/2006 |
| WO | WO 2007/073226 | 6/2007 |
| WO | WO 2007/085806 A2 | 8/2007 |
| WO | WO 2008/003953 A2 | 1/2008 |
| WO | WO 2008/069688 | 6/2008 |
| WO | WO 2008/130261 A1 | 10/2008 |
| WO | WO 2009/013612 A1 | 1/2009 |

OTHER PUBLICATIONS

[No Author Listed], Solutions, emulsions, suspensions, and extractives. Remington's Pharmaceutical Science. 1985; 17th edition. Gennaro, ed. Ch. 84. p. 1511-2.
Abe et al., The effects of prostacyclin analog OP-41483 on normothermic liver ischemia and reperfusion injury in rats. Prostaglandins Leukot Essent Fatty Acids. Jun. 1993;48(6):417-22.
Abel et al., Anionic halogenopentacarbonyls of chromium, molybdenum, and tungsten. J Chem Soc. Apr. 16, 1963:2068-70.
Abel et al., Carbonyl halides of manganese and some related compounds. J Chem Soc. 1959;Part 2:1501-5.
Abel et al., Reaction of molybdenum carbonyl with various halides: a potassium etherate salt. Chem Indust. 1960;442.
Abel et al., Transition-metal complexes of seven-membered ring systems. Part I: the cycloHeptatriene-Metal Complexes and Related Compounds. J. Chem. Soc. 1958:4559-63.
Abraham et al., The biological significance and physiological role of heme oxygenase. Cell Physiol Biochem. 1996;6:129-68.
Aburaya et al., Heme oxygenase-1 protects gastric mucosal cells against non-steroidal anti-inflammatory drugs. J Biol Chem. Nov. 3, 2006;281(44):33422-32. Epub Aug. 31, 2006.
Adkison et al., Semicarbazone-based inhibitors of cathepsin K, are they prodrugs for aldehyde inhibitors? Bioorg Med Chem Lett. Feb. 15, 2006;16(4):978-83. Epub Nov. 15, 2005. Abstract only.
Akamatsu et al., Heme oxygenase-1-derived carbon monoxide protects hearts from transplant associated ischemia reperfusion injury. FASEB J. Apr. 2004;18(6):771-2. Epub Feb. 20, 2004.
Albers et al., Cobalt chloride: An inexpensive catalyst for the substitution of CO by isonitriles on M(CO)6 (M=Cr, Mo, W). J of Orgnaometallic Chemistry. Oct. 21, 1980;199(1):55-62.
Albers et al., The use of supported transition metals and metal oxides as catalysts for the metal carbonyl substitution reaction. J Chem Soc, Chem Commun. 1982:96-7.
Alberto et al., A novel organometallic aqua complex of technetium for the labeling of biomolecules: synthesis of [99mTc(OH2)3(CO)3]+ from [99mTcO4]− in aqueous solution and its reaction with a bifunctional ligand. J Am Chem Soc. 1998;120:7987-8. Epub Jul. 24, 1998.
Alberto et al., Synthesis and properties of boranocarbonate: a convenient in situ CO source for the aqueous preparation of [(99m)Tc(OH(2))3(CO)3]+. J Am Chem Soc. Apr. 4, 2001;123(13):3135-6. Epub Mar. 13, 2001.
Alessio et al., Carbonyl Derivatives of Chloride-Dimethyl Sulfoxide-Ruthenium(II) Complexes: Synthesis, Structural Characterization, and Reactivity of Ru(CO)x(DMSO)4-xC12 Complexes (x=1-3). Inorg Chem. 1995;34(19):4722-34.
Alessio et al., Carbonyl Derivatives of Chloride-Dimethyl Sulfoxide-Ruthenium(III) Complexes: Synthesis, Crystal Structure, and Reactivity of [(DMSO)2H][trans-RuCl4(DMSO-O)(CO)] and mer,cis-RuC13(DMSO-O)2(CO). Inorg Chem. 1995;34(19):4716-21.
Allanson et al., Ultraviolet A (320-400 nm) modulation of ultraviolet B (290-320 nm)-induced immune suppression is mediated by carbon monoxide. J Invest Dermatol. Mar. 3, 2005;124(3):644-50.
Allardyce et al., Development of organometallic (organo-transition metal) pharmaceuticals. Appl Organomet Chem. Jan. 2005;19:1-10.
Amersi et al., Ex vivo exposure to carbon monoxide prevents hepatic ischemia/reperfusion injury through p38 MAP kinase pathway. Hepatology. Apr. 2002;35(4):815-23.
Andreadis et al., Oxidative and nitrosative events in asthma. Free Radic Biol Med. Aug. 1, 2003;35(3):213-25. Review. Abstract only.
Angelici et al., Carboxamido carbonyl complexes of manganese(I). Inorg Chim Acta. Mar. 1968;2:3-7. Abstract only.
Angelici, Preparation, characterization, and reactions of the cis-Dihalotetracarbonylmanganate(I) anions. Inorg Chem. Aug. 1964;3(8):1099-1102.
Aujard et al., Tridemethylisovelleral, a potent cytotoxic agent. Bioorg Med Chem. Nov. 15, 2005;13(22):6145-50. Epub Aug. 1, 2005. Abstract only.
Bagul et al., Carbon monoxide protects against ischemia-reperfusion injury in an experimental model of controlled nonheartbeating donor kidney. Transplantation. Feb. 27, 2008;85(4):576-81.
Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.
Bannenberg et al., Therapeutic applications of the gaseous mediators carbon monoxide and hydrogen sulfide. Expert Opin Ther Pat. May 2009;19(5):663-82. Review.
Barkoudah et al., The permissive role of endothelial NO in CO-induced cerebrovascular dilation. Am J Physiol Heart Circ Physiol. Oct. 2004;287(4):H1459-65. Epub Jun. 10, 2004.
Bauer et al., Evidence for a functional link between stress response and vascular control in hepatic portal circulation. Am J Physiol. Nov. 1996;271(5 Pt 1):G929-35.
Bauerová et al., Role of reactive oxygen and nitrogen species in etiopathogenesis of rheumatoid arthritis. Gen Physiol Biophys. Oct. 1999;18 Spec No. 15-20. Review. Abstract only.
Beal, Oxidatively modified proteins in aging and disease. Free Radic Biol Med. May 1, 2002;32(9):797-803. Review. Abstract only.
Beaty et al., An in vitro model for the in vivo mobilization of cadmium by chelating agents using 113Cd-NMR spectroscopy. Chem Res Toxicol. Jul.-Aug. 1992;5(4):568-75. Abstract only.
Beck et al., Metallkomplexe mit biologisch wichtigen liganden : XVIII. Histidinato-carbonyl-komplexe von molybdän und wolfram. J Organometallic Chemistry. May 27, 1980;191(1):73-7.
Becker et al., Age-related changes in antibody-dependent cell-mediated cytotoxicity in mouse spleen. Isr J Med Sci. Feb. 1979;15(2):147-50.
Becker et al., NO-independent regulatory site of direct sGC stimulators like YC-1 and BAY 41/2272. BMC Pharmacol. 2001;1:13. Epub Dec. 28, 2001.
Berman et al., Sensitization and catalysis of light-induced decarbonylation of aldehydes. J Am Chem Soc. 1963;85(24):4010-4013.
Beutler, The effect of carbon monoxide on red cell life span in sickle cell disease. Blood. Aug. 1975;46(2):253-9.
Boissiere et al., Exercise and vasorelaxing effects of CO-releasing molecules in hypertensive rats. Med Sci Sports Exerc. Apr. 2006;38(4):652-9.
Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.
Brashears et al., Effect of meat packaging technologies on the safety and spoilage-indicating characteristics of ground beef—Phase 1: safety characteristics. Jun.-Jul. 2006. National Cattleman's Beef Asscoiation. 22 pages. Available at www.fda.gov/ohrms/dockets/dockets/05p0459/05p-0459-c000009-01-vol2.pdf.

(56) References Cited

OTHER PUBLICATIONS

Brisdon et al., The preparation and charactisation of tri-μ-halogenohexacarbonyl-dimetallate(I) anions of manganese and rhenium. J Organometallic Chem. 1978;161:233-43.
Brooks et al., The spoilage characteristics of ground beef packaged in high-oxygen and low-oxygen modified atmosphere packages. Proc. Reciprocal Meat Conference. University of Illinois at Urbana-Champaign. Jun. 18-21, 2006:61-5.
Brouard et al., Carbon monoxide generated by heme oxygenase 1 suppresses endothelial cell apoptosis. J Exp Med. Oct. 2, 2000;192(7):1015-25.
Brüne et al., Inhibition of platelet aggregation by carbon monoxide is mediated by activation of guanylate cyclase. Mol Pharmacol. Oct. 1987;32(4):497-504.
Bundgaard et al., Pro-drugs as delivery systems. Pharm Int. 1981;2:136-40.
Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.
Burgmayer et al., Synthesis and structure of a 7-coordinate molybdenum carbonyl fluoride derivative—Et4n Mo(Co)2(S2cnet2)2f. Inorganic Chem. 1985;24:2224-30.
Burleson et al., The effect of dyes used to evaluate the in situ, ex-vivo, and perfused kidney. Invest Urol. Nov. 1981;19(3):165-8. Abstract only. Accession No. PREV198273058212.
Campbell et al., Molecular targets in immune-mediated diseases: the case of tumour necrosis factor and rheumatoid arthritis. Immunol Cell Biol. Oct. 2003;81(5):354-66.
Carroll et al., Ligand abstraction in the reaction of aryldiazonium ions with some iron complexes containing coordinated cysteine, maleonitriledithiol, or triarylphosphine. Can J Chem. 1974;52:1914-22.
Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191. Epub Nov. 8, 2007.
Chakravortty et al., Inducible nitric oxide synthase and control of intracellular bacterial pathogens. Microbes Infect. Jun. 2003;5(7):621-7. Review. Abstract only.
Chatterjee, Water-soluble carbon monoxide-releasing molecules: helping to elucidate the vascular activity of the 'silent killer'. Br J Pharmacol. Jun. 2004;142(3):391-3. Epub May 17, 2004.
Chauveau et al., Gene transfer of heme oxygenase-1 and carbon monoxide delivery inhibit chronic rejection. Am J Transplant. Aug. 2002;2(7):581-92.
Chlopicki et al., Carbon monoxide released by CORM-3 inhibits human platelets by a mechanism independent of soluble guanylate cyclase. Cardiovasc Res. Jul. 15, 2006;71(2):393-401. Epub Mar. 22, 2006.
Cihonski et al., Crown ethers in inorganic chemistry—preparation and characterization of group 6 pentacarbonyl hydroxides and fluorides. Inorganic Chem. 1975;14(7):1717-20.
Clark et al., Cardioprotective actions by a water-soluble carbon monoxide-releasing molecule. Circ Res. Jul. 25, 2003;93(2):e2-8. Epub Jul. 3, 2003.
Clark et al., Heme oxygenase-1-derived bilirubin ameliorates postischemic myocardial dysfunction. Am J Physiol Heart Circ Physiol. Feb. 2000;278(2):H643-51.
Clark et al., Measuring left ventricular function in the normal, infarcted and CORM-3-preconditioned mouse heart using complex admittance-derived pressure volume loops. J Pharmacol Methods Toxicol. Mar.-Apr. 2009;59(2):94-9.
Coburn et al., Endogenous carbon monoxide production in man. J Clin Invest. Jul. 1963;42(7):1172-8.
Coceani et al., Carbon monoxide formation in the ductus arteriosus in the lamb: implications for the regulation of muscle tone. Br J Pharmacol. Feb. 1997;120(4):599-608.
Coceani, Carbon monoxide in vasoregulation: the promise and the challenge. Circ Res. Jun. 23, 2000;86(12):1184-6. Review.

Cohen et al., Dithiobenzoatotetracarbonylmanganese(I). Inorg Chem. 1964;3(11):1641-42.
Conant et al., Trimethylacetaldehyde and dimethylethylacetaldehyde. J Am Chem Soc. Apr. 1929;51(4):1246-55.
Cotton et al., Dimethyl- and diethyldithiocarbamate complexes of some metal carbonyl compounds. Inorg Chem. Jun. 2, 1964;3:1398-1402.
Cotton et al., X-ray molecular structures of Mn(CO)5(O2CCF3) and Mn(CO)3(C5H5N)2(O2CCF3). Inorg Chem. 1981;20(4):1287-91.
Coville et al., Steric measurement of substituted cyclopentadiene ligands and the synthesis and proton NMR spectral analysis of [(.eta.5-C5H4R)Fe(CO)(L)I] complexes with variable R. Organometallics. 1992;11(3):1082-90.
Crabtree, Immune and inflammatory responses to Helicobacter pylori infection. Scandinavian J Gastroenterology. 1996;31(s215):3-10. Abstract only.
De Backer et al., Mechanisms of relaxation by carbon monoxide-releasing molecule-2 in murine gastric fundus and jejunum. Eur J Pharmacol. Oct. 31, 2007;572(2-3):197-206. Epub Jun. 13, 2007.
De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.
De Backer et al., Water-soluble CO-releasing molecules reduce the development of postoperative ileus via modulation of MAPK/HO-1 signalling and reduction of oxidative stress. Gut. Mar. 2009;58(3):347-56. Epub Nov. 20, 2008.
De Filippo et al., Inductive effect in dithiocarbanate decomposition mechanism. J Org Chem. 1973;38(3):560-3.
Deicas et al., Synthesis, characterization and spectroscopic properties of [CuI(alkylisocyanide)4]BF4 complexes. X-ray crystal structures of [Cu(MIBI)4]BF4 and [Cu(CPI)4]BF4. Polyhedron. 1997; 16(4):2397-403.
Desmard et al., A carbon monoxide-releasing molecule (CORM-3) exerts bactericidal activity against Pseudomonas aeruginosa and improves survival in an animal model of bacteraemia. FASEB J. Apr. 2009;23(4):1023-31. Epub Dec. 18, 2008.
Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.
Dharmaraj, Ruthenium (II) complexes containing bidentate Schiff bases and their antifungal activity. Transition Metal Chemistry. 2001; 26(1-2): 105-109.
Di Pascoli et al., Chronic CO levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.
Diamantis et al., Preparation and structure of ethylenediaminetetraacetate complexes of ruthenium(II) with dinitrogen, carbon monoxide, and other π-acceptor ligands. Inorg Chem. 1981;20:1142-50.
Douglas et al., Preparation of some group Vi fluorometal carbonyl derivatives. J Organometal Chem. 1974;65:65-9.
Drew et al., Synthesis, spectral properties, and reactions of manganese and rhenium pentacarbonyl phosphine and phosphite cation derivatives and related complexes. Inorg. Chem. 1975;14(7):1579-84.
Dröge, Free radicals in the physiological control of cell function. Physiol Rev. Jan. 2002;82(1):47-95. Review.
Duchêne et al., Cyclodextrins in targeting. Application to nanoparticles. Adv Drug Deliv Rev. Mar. 1, 1999;36(1):29-40.
Duckers et al., Heme oxygenase-1 protects against vascular constriction and proliferation. Nat Med. Jun. 2001;7(6):693-8.
Durante, Heme oxygenase-1 in growth control and its clinical application to vascular disease. J Cell Physiol. Jun. 2003;195(3):373-82. Review.
Egli et al., Organometallic 99mTc-aquaion labels peptide to an unprecedented high specific activity. J Nucl Med. Nov. 1999;40(11):1913-7.

(56) References Cited

OTHER PUBLICATIONS

El-Kholy, Catalysis by crown ether complexes—part III effect of cation on the catalytic activity of crown ether-alkali metal halide complexes in the liquid phase oxidation of ethylbenzene. Egypt J Chem. 1979;22(1):23-8.
Elliott et al., Nitric oxide: a regulator of mucosal defense and injury. J Gastroenterol. Dec. 1998;33(6):792-803. Review. Abstract only.
Fairlamb et al., η4-pyrone iron(0)carbonyl complexes as effective CO-releasing molecules (CO-RMs). Bioorg Med Chem Lett. Feb. 15, 2006;16(4):995-8. Epub Nov. 11, 2005.
Fang, Antimicrobial reactive oxygen and nitrogen species: concepts and controversies. Nat Rev Microbiol. Oct. 2004;2(10):820-32. Review. Abstract only.
Feldmann et al., Anti-TNF alpha therapy of rheumatoid arthritis: what have we learned? Annu Rev Immunol. 2001;19:163-96. Review.
Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.
Ferrier et al., FTIR spectrometric study of geometrical isomers of dicarbonyl ferrobiscyteinate influence of the counter cation.J Molec Struct. 1995;344(3):189-93.
Fischer et al., Methylpyridin-Chrom(O)-Tricarbonyl. Zeitschrift Fur Naturforschung Part-B-Chemie Biochemie Biophysik Biologie Und Verwandten Gebiete. 1959;14:736-7. English translation provided.
Fischer et al., Uber aromatenkomplexe von metallen .37. zur aromatenkomplexebildung des pyridins mit chromhexacarbonyl. Chemische berichte-recueil. 1960;93:1156-61. English abstract provided.
Fischer, Crystal structure of 1,4,7,10,13-pentaoxacylcopentadecane sodium bromide, C10H20BrNaO5. Zeitschrift fur kristallographie. 1996;211:827-8. English translation provided.
Fiumana et al., Carbon monoxide mediates vasodilator effects of glutamate in isolated pressurized cerebral arterioles of newborn pigs. Am J Physiol Heart Circ Physiol. Apr. 2003;284(4):H1073-9.
Flemstrom et al., Gastroduodenal HCO3(–) transport: characteristics and proposed role in acidity regulation and mucosal protection. Am J Physiol. Mar. 1982;242(3):G183-93.
Foresti et al., Reviewing the use of carbon monoxide-releasing molecules (CO-RMs) in biology: implications in endotoxin-mediated vascular dysfunction. Cell Mol Biol (Noisy-le-grand). Sep. 30, 2005;51(4):409-23.
Foresti et al., The heme oxygenase pathway and its interaction with nitric oxide in the control of cellular homeostasis. Free Radic Res. Dec. 1999;31(6):459-75. Review.
Foresti et al., Use of carbon monoxide as a therapeutic agent: promises and challenges. Intensive Care Med. Apr. 2008;34(4):649-58.
Foresti et al., Vasoactive properties of CORM-3, a novel water-soluble carbon monoxide-releasing molecule. Br J Pharmacol. Jun. 2004;142(3):453-60. Epub May 17, 2004.
Frangogiannis et al., The inflammatory response in myocardial infarction. Cardiovasc Res. Jan. 2002;53(1):31-47. Review.
Friebe et al., Sensitizing soluble guanylyl cyclase to become a highly CO-sensitive enzyme. EMBO J. Dec. 16, 1996;15(24):6863-8.
Friebe et al., YC-1 potentiates nitric oxide- and carbon monoxide-induced cyclic GMP effects in human platelets. Mol Pharmacol. Dec. 1998;54(6):962-7.
Fujita et al., Paradoxical rescue from ischemic lung injury by inhaled carbon monoxide driven by derepression of fibrinolysis. Nat Med. May 2001;7(5):598-604.
Fukuda et al., Induction of heme oxygenase-1 (HO-1) after traumatic brain injury in the rat. Neurosci Lett. Oct. 20, 1995;199(2):127-30.
Furchgott et al., Endothelium-dependent and -independent vasodilation involving cyclic GMP: relaxation induced by nitric oxide, carbon monoxide and light. Blood Vessels. 1991;28(1-3):52-61.
Giboreau et al., Procedure for the preparation of pure dithiocarbamates. J Org Chem. 1994;59:1205-7.
Girolami et al., Reaction of binuclear carboxylate complexes of molybdenum, rhenium, ruthenium, and rhodium with tert-Butyl Isocyanide: metal-metal bond cleavage vs. bond retention. Inorganic Chemistry. Jul. 1981;20(7):2040-4.
Gordeuk et al., Carbonyl iron therapy for iron deficiency anemia. Blood. Mar. 1986;67(3):745-52.
Gottschaldt et al., Sugar-selective enrichment of a D-glucose-substituted ruthenium bipyridyl complex inside HepG2 cancer cells. Chembiochem. Mar. 22, 2010;11(5):649-52. Epub Feb. 15, 2010.
Greener et al., Now you're signaling, with gas: gasotransmitters open a window on biology and drug development. The Scientist. Sep. 13, 2004;18(17):20-2.
Günther et al., Carbon monoxide protects pancreatic beta-cells from apoptosis and improves islet function/survival after transplantation. Diabetes. Apr. 2002;51(4):994-9. MEDLINE Abstract. Accession No. NLM11916917.
Guo et al., Administration of a CO-releasing molecule at the time of reperfusion reduces infarct size in vivo. Am J Physiol Heart Circ Physiol. May 2004;286(5):H1649-53. Epub Jan. 2, 2004.
Haag et al., Polymer therapeutics: concepts and applications. Angew Chem Int Ed Engl. Feb. 13, 2006;45(8):1198-215. Review. Abstract only.
Haddleton et al., [N-Alkyl-(2-pyridypmethanimine]copper(I) complexes: characterisation and application as catalysts for atom-transfer polymerisation. Eur J Inorg Chem. Dec. 7, 1998;1998(11):1799-1806. Abstract only.
Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.
Hadjigogos, The role of free radicals in the pathogenesis of rheumatoid arthritis. Panminerva Med. Mar. 2003;45(1):7-13. Review. Abstract only.
Hall et al., DNA interaction with metal complexes and salts of substituted boranes and hydroborates in murine and human tumor cell lines. Anticancer Drugs. Aug. 1991;2(4):389-99.
Hall et al., The anti-inflammatory activity of boron derivatives in rodents. Met Based Drugs. 1995;2(1):1-12.
Hall et al., The anti-inflammatory activity of metal complexes and salts of amine carboxyboranes. Appl Organomett Chem. 1994;8:473-80.
Hall et al., The hypolipidemic activity of metal complexes of amine carboxyboranes in rodents. Met Based Drugs. 1994;1(4):329-36.
Hancock et al., Antibody-induced transplant arteriosclerosis is prevented by graft expression of anti-oxidant and anti-apoptotic genes. Nat Med. Dec. 1998;4(12):1392-6.
Henricks et al., Reactive oxygen species as mediators in asthma. Pulm Pharmacol Ther. 2001;14(6):409-20. Review. Abstract only.
Herrick et al., Flash photolytic investigation of photinduced carbon monoxide dissociation from dinuclear manganese carbonyl compounds. Inorg Chem. 1984;23:4550-3.
Herrmann et al., Synthetic Methods of Organometallic and Inorganic Chemistry, vol. 1, Chapter 3 Commonly Used Starting Materials. Georg Thieme Verlag, New York, 1996, p. 129.
Hieber et al., Derivate des Mangancarbonyls mit schwefelorganischen Liganden. Chemische Berichte. 1966;99(7):2312-21. English abstract provided.
Hitchon et al., Oxidation in rheumatoid arthritis. Arthritis Res Ther. 2004;6(6):265-78. Epub Oct. 13, 2004. Review.
Hogg, Free radicals in disease. Semin Reprod Endocrinol. 1998;16(4):241-8. Review. Abstract only.
Holmuhamedov et al., Mitochondrial ATP-sensitive K+ channels modulate cardiac mitochondrial function. Am J Physiol. Nov. 1998;275(5 Pt 2):H1567-76.
Hosgood et al., Application of nitric oxide and carbon monoxide in a model of renal preservation. Br J Surg. Aug. 2008;95(8):1060-7.
Huang et al., Photolysis of the histidine-heme-CO complex. J Am Chem Soc. Nov. 1, 1991;113:9141-4.
Huebers et al., Absorption of carbonyl iron. J Lab Clin Med. Nov. 1986;108(5):473-8.

(56) References Cited

OTHER PUBLICATIONS

Ignat'ev et al., Reactivity of perfluoroakyl halides towards nucleophiles. Russ J Electrochem. Dec. 1995;31(12):1235-9. Translated from Elektrokhimiya. 1995:31(12):1337-42.

Jander et al., Neutralisationenanaloge reaktionen in essigaureanhybrid. Zietschrift fur anorganische chemie. 1948;255:238-52. English abstract provided.

Jellum et al., Quantitative determination of biologically important thiols and disulfides by gas-liquid chromatography. Analyt Biochem. 1969;31:339-47. Abstract only.

Johansen et al., Spectrophotometric determination of the rates of hydrolysis of aldehyde-releasing pro-drugs in aqueous solution and plasma. Intl J Pharma. Dec. 1982;13(1):89-98. Abstract only.

Johnson et al., Metal carbonyls as pharmaceuticals? [Ru(CO)3Cl(glycinate)], a CO-releasing molecule with an extensive aqueous solution chemistry. Dalton Trans. Apr. 21, 2007;(15):1500-8. Epub Mar. 8, 2007.

Johnson et al., Metal carbonyls: a new class of pharmaceuticals? Angew Chem Int Ed Engl. Aug. 18, 2003;42(32):3722-9.

Johnson et al., Role of endogenous carbon monoxide in central regulation of arterial pressure. Hypertension. Oct. 1997;30(4):962-7.

Józkowicz et al., Heme oxygenase and angiogenic activity of endothelial cells: stimulation by carbon monoxide and inhibition by tin protoporphyrin-IX. Antioxid Redox Signal. Apr. 2003;5(2):155-62.

Kamimura et al., The protective effect of carbon monoxide on the ischemia-induced cell death. The J Biochem. Aug. 2002;74(8):926. Japanese abstract. English translation provided.

Kharitonov et al., Basis of guanylate cyclase activation by carbon monoxide. Proc Natl Acad Sci U S A. Mar. 28, 1995;92(7):2568-71.

Kharitonov et al., Kinetics and equilibria of soluble guanylate cyclase ligation by CO: effect of YC-1. Biochemistry. Aug. 17, 1999;38(33):10699-706.

King et al, CAS Database Accession No. 1974:83184. 1 page.

Kirtley, Molybdenum Compounds with $nu^1$-Carbon Ligands in Comprehensive Organometallic Chemistry I. Pergamon, Oxford. Sections 27.1.2.5 and 27.1.3.2. 1982; vol. 3:1120-26 and 1134-45.

Krueger et al., Potential of tumor necrosis factor inhibitors in psoriasis and psoriatic arthritis. Arch Dermatol. Feb. 2004;140(2):218-25. Review.

Kubic et al., Metabolism of dihalomethanes to carbon monoxide. I. In vivo studies. Drug Metab Dispos. Jan.-Feb. 1974;2(1):53-7. Abstract only.

Kuiate et al., Composition of the essential oil from leaves and flowers of *Dichrocephala integrifolia* (L.) O. Kuntze Chev. From Cameroon. Flavour and Fragrance J. Nov./Dec. 1999;14(6):419-20. Abstract only.

Lambert et al., O,O'-Diphenyldithiophosphatotetracarbonylmanganese(I) and related compounds. Inorg Chem. 1966;5(7):1287-9.

Lawton et al., Myocardial oxygen consumption in the rabbit heart after ischemia: hyperpolarized arrest with pinacidil versus depolarized hyperkalemic arrest. Circulation. Nov. 4, 1997;96(9 Suppl):II-247-52.

Ledger, Carbon monoxide-releasing metal carbonyls: a new class of pharmaceuticals? Drug Disc Today. Dec. 2003;8(23):1096.

Lee et al., Heme oxygenase-1 mediates the anti-inflammatory effect of interleukin-10 in mice. Nat Med. Mar. 2002;8(3):240-6.

Levrand et al., Controlled release of volatile aldehydes and ketones by reversible hydrazone formation—classical profragrances are getting dynamic. Chem. Commun. 2006;28:2965-7. Epub Apr. 3, 2006.

Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90. Epub Feb. 20, 2006.

Lipmann et al., Organometallic Lewis Acids. LI. Reactivity of organometallic Lewis Acids (OC)4Re(OEt2)FBF3 and (OC)2(PPh3)2Ru(FBF3)2. Journal of Organometallic Chemistry. 1994;466(1-2):167-174. English abstract provided.

Liu et al., Cyclic GMP-dependent protein kinase activation and induction by exisulind and CP461 in colon tumor cells. J Pharmacol Exp Ther. Nov. 2001;299(2):583-92.

Loftsson et al., Cyclodextrins in topical drug formulations: theory and practice. Int J Pharm. Aug. 28, 2001;225(1-2):15-30. Review.

Loganson et al., Metal carbonyl complexes with ligands of biological origin. Russ Chem Rev. 1985;54(3):277-92.

Lovell et al., Biologic agents for the treatment of juvenile rheumatoid arthritis: current status. Paediatr Drugs. 2004;6(3):137-46.

Mahmoud et al., Potential anticancer agents. XVI. Isolation of bicyclofarnesane sesquiterpenoids from Capsicodendron dinisii. J Nat Prod. May-Jun. 1980;43(3):365-71. Abstract only.

Mai et al., Soluble surface proteins from Helicobacter pylori activate monocytes/macrophages by lipopolysaccharide-independent mechanism. J Clin Invest. Mar. 1991;87(3):894-900.

Maines, Heme oxygenase: function, multiplicity, regulatory mechanisms, and clinical applications. FASEB J. Jul. 1988;2(10):2557-68. Review.

Maines, The heme oxygenase system: a regulator of second messenger gases. Annu Rev Pharmacol Toxicol. 1997;37:517-54. Review.

Marks et al., Does carbon monoxide have a physiological function? Trends Pharmacol Sci. May 1991;12(5):185-8. Review.

Martins et al., Induction of carbon monoxide in the donor reduces graft immunogenicity and chronic graft deterioration. Transplant Proc. Jan.-Feb. 2005;37(1):379-81.

Matsuda et al., Mediators of non-adrenergic non-cholinergic inhibitory neurotransmission in porcine jejunum. Neurogastroenterol Motil. Oct. 2004;16(5):605-12.

Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.

McLaughlin et al., Potentiation of carbon monoxide-induced relaxation of rat aorta by YC-1 [3-(5'-hydroxymethyl-2'-furyl)-1-benzylindazole]. Can J Physiol Pharmacol. Apr. 2000;78(4):343-9.

McMillen et al., Hydrocarbon bond dissociation energies. Ann Rev Phys Chem. Oct. 1982;33:493-532.

Meder et al., Metallkomplexe mit biologisch wichtigen liganden, XLII [1] carbonylmetallkomplexe mit anionen von mehrfunktionellen alpha-aminosaeuren [Metal complexes with biologically important ligands], XLII [1] carbonyl metal complexes with anions of polyfunctional alpha-amino acids]. Zeitchrift fur Naturforschung;1986:1247-54. German language reference. English abstract provided.

Megías et al., The carbon monoxide-releasing molecule tricarbonyldichlororuthenium(II) dimer protects human osteoarthritic chondrocytes and cartilage from the catabolic actions of interleukin-1beta. J Pharmacol Exp Ther. Apr. 2008;325(1):56-61. Epub Jan. 14, 2008.

Miguel et al., Manganese(I) complexes with (tricyclohexylphosphonio)dithiocarboxylate as chelate and unidentate ligand. X-Ray crystal structure of fac-[Mn(CO)3{S2CP(C6H11)3}2]ClO4•H2O. J Chem Soc, Dalton Trans. 1987;12:2875-80.

Mikuls et al., Benefit-risk assessment of infliximab in the treatment of rheumatoid arthritis. Drug Saf. 2003;26(1):23-32. Review. Abstract only.

Miller et al., The pharmacological activities of the metabolites of N-[(trimethylamineboryl)- carbonyl]-L-phenylalanine methyl ester. Met Based Drugs. 1996;3(5):219-26.

Moncada et al., Nitric oxide: physiology, pathophysiology, and pharmacology. Pharmacol Rev. Jun. 1991;43(2):109-42.

Moncada et al., The discovery of nitric oxide and its role in vascular biology. Br J Pharmacol. Jan. 2006;147 Suppl 1:S193-201.

Moore et al., Brief inhalation of low-dose carbon monoxide protects rodents and swine from postoperative ileus. Crit Care Med. Jun. 2005;33(6):1317-26.

Morita et al., Carbon monoxide controls the proliferation of hypoxic vascular smooth muscle cells. J Biol Chem. Dec. 26, 1997;272(52):32804-9.

(56) References Cited

OTHER PUBLICATIONS

Morita et al., Endothelial cell expression of vasoconstrictors and growth factors is regulated by smooth muscle cell-derived carbon monoxide. J Clin Invest. Dec. 1995;96(6):2676-82.

Morita et al., Smooth muscle cell-derived carbon monoxide is a regulator of vascular cGMP. Proc Natl Acad Sci US A. Feb. 28, 1995;92(5):1475-9.

Morse et al., Suppression of inflammatory cytokine production by carbon monoxide involves the JNK pathway and AP-1. J Biol Chem. Sep. 26, 2003;278(39):36993-8. Epub Jul. 11, 2003.

Motterlini et al., Bioactivity and pharmacological actions of carbon monoxide-releasing molecules. Curr Pharm Des. 2003;9(30):2525-39.

Motterlini et al., Carbon monoxide-releasing molecules: characterization of biochemical and vascular activities. Circ Res. Feb. 8, 2002;90(2):E17-24.

Motterlini et al., Chapter 16: Studies on the development of carbon-monoxide-releasing molecules: potential applications for the treatment of cardiovascular dysfunction. Ed., Rui Wang. CRC Press, New York. 2002:249-72.

Motterlini et al., Characterization of vasoactive effects elicited by carbon monoxide-releasing molecules. Abstracts 8th Intl Symposium on Mechanisms of Vasodilation. J Vasc Res. May 31-Jun. 3, 2001;055.

Motterlini et al., CORM-A1: a new pharmacologically active carbon monoxide-releasing molecule. FASEB J. Feb. 2005;19(2):284-6. Epub Nov. 19, 2004.

Motterlini et al., Functional and metabolic effects of propionyl-L-carnitine in the isolated perfused hypertrophied rat heart. Mol Cell Biochem. Oct. 21, 1992;116(1-2):139-45.

Motterlini et al., Heme oxygenase-1-derived carbon monoxide contributes to the suppression of acute hypertensive responses in vivo. Circ Res. Sep. 7, 1998;83(5):568-77. Correction included.

Motterlini et al., Therapeutic applications of carbon monoxide-releasing molecules. Expert Opin Investig Drugs. Nov. 2005;14(11):1305-18. Review.

Motterlini, Vasoactive properties of carbon monoxide-releasing molecules. Biomed Pharmacother. 2002;56(7):349-50.

Moya et al., Metal carbonyl complexes containing heterocyclic nitrogen ligands: Part IX. MnBr(CO)3(3,3'-R-2,2'-biquinoline) compounds. Polyhedron. Mar. 1, 2002; 21(4):439-44. Abstract only.

Mungrue et al., From molecules to mammals: what's NOS got to do with it? Acta Physiol Scand. Oct. 2003;179(2):123-35. Review. Abstract only.

Musameh et al., Improved myocardial function after cold storage with preservation solution supplemented with a carbon monoxide-releasing molecule (CORM-3). J Heart Lung Transplant. Nov. 2007;26(11):1192-8.

Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.

Nagai et al., Unusual CO bonding geometry in abnormal subunits of hemoglobin M Boston and hemoglobin M Saskatoon. Biochemistry. Jul. 2, 1991;30(26):6495-503.

Nakao et al., Carbon monoxide inhalation protects rat intestinal grafts from ischemia/reperfusion injury. Am J Pathol. Oct. 2003;163(4):1587-98.

Nakao et al., Protective effect of carbon monoxide in transplantation. J Cell Mol Med. Jul.-Sep. 2006;10(3):650-71. Review.

Nathan, Points of control in inflammation. Nature. Dec. 19-26, 2002;420(6917):846-52. Review.

Ndisang et al., Modulation of the immunological response of guinea pig mast cells by carbon monoxide. Immunopharmacology. Jun. 1999;43(1):65-73.

Neto et al., Protection of transplant-induced renal ischemia-reperfusion injury with carbon monoxide. Am J Physiol Renal Physiol. Nov. 2004;287(5):F979-89. Epub Aug. 3, 2004.

Nitschke et al., Properties of (trifluoromethanesulfonato)pentacarbonylmanganese(I) and -rhenium(I). Reactions in superacid solvents. Inorg Chem. 1985;24(13):1972-8.

Nobre et al., Antimicrobial action of carbon monoxide-releasing compounds. Antimicrob Agents Chemother. Dec. 2007;51(12):4303-7. Epub Oct. 8, 2007.

Nudelman et al., Prodrugs of butyric acid. Novel derivatives possessing increased aqueous solubility and potential for treating cancer and blood diseases. Eur J Med Chem. Jan. 2001;36(1):63-74. Abstract only.

Nudelman et al., The role of intracellularly released formaldehyde and butyric acid in the anticancer activity of acyloxyalkyl esters. J. Med. Chem. Feb. 24, 2005. 2005;48(4):1042-54. Epub Jan. 22, 2005. Abstract only.

Nydegger et al., New concepts in organ preservation. 4):215-25. Transpl Immunol. May 2002;9(2-4):215-25.

O'Brien et al., Aldehyde sources, metabolism, molecular toxicity mechanisms, and possible effects on human health. Crit Rev Toxicol. Aug. 2005;35(7):609-62. Review.

Otterbein et al., Carbon monoxide has anti-inflammatory effects involving the mitogen-activated protein kinase pathway. Nat Med. Apr. 2000;6(4):422-8.

Otterbein et al., Carbon monoxide provides protection against hyperoxic lung injury. Am J Physiol. Apr. 1999;276(4 Pt 1):L688-94.

Otterbein et al., Carbon monoxide suppresses arteriosclerotic lesions associated with chronic graft rejection and with balloon injury. Nat Med. Feb. 2003;9(2):183-90. Epub Jan. 21, 2003.

Otterbein et al., Exogenous administration of heme oxygenase-1 by gene transfer provides protection against hyperoxia-induced lung injury. J Clin Invest. Apr. 1999;103(7):1047-54.

Otterbein et al., Heme oxygenase-1: unleashing the protective properties of heme. Trends Immunol. Aug. 2003;24(8):449-55. Review.

Otterbein, Carbon monoxide: innovative anti-inflammatory properties of an age-old gas molecule. Antioxid Redox Signal. Apr. 2002;4(2):309-19. Review.

Ozawa et al., Leydig cell-derived heme oxygenase-1 regulates apoptosis of premeiotic germ cells in response to stress. J Clin Invest. Feb. 2002;109(4):457-67.

Pae et al., Carbon monoxide produced by heme oxygenase-1 suppresses T cell proliferation via inhibition of IL-2 production. J Immunol. Apr. 15, 2004;172(8):4744-51.

Paintner et al., Synthesis and antimicrobial activity of tetrodecamycin partial structures. Bioorg Med Chem. Jul. 3, 2003;11(13):2823-33. Abstract only.

Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.

Patel et al., Preparation of ($\eta$5-cyclopentadienyl) and ($\eta$5-Methylcyclopentadienyl)Fe(CO)2Me cyclodextrin inclusion compounds and their subsequent ligand substitution reactions. Attempts at cyclodextrin mediated enantioselective ligand substitution. J Organometal Chem. 1997;547:103-112.

Peloso et al., Expanding the armamentarium for the spondyloarthropathies. Arthritis Res Ther. 2004;6 Suppl 2:S36-43. Epub Jun. 21, 2004.

Pena et al., A novel carbon monoxide-releasing molecule fully protects mice from severe malaria. Antimicrob Agents Chemother. Mar. 2012;56(3):1281-90. Epub Dec. 12, 2011.

Piantadosi, Biological chemistry of carbon monoxide. Antioxid Redox Signal. Apr. 2002;4(2):259-70. Review.

Pneumatikakis et al., Interactions of bis-[$\mu$-chloro-chlorotricarbonylruthenium(II) and poly-[$\mu$-dichloro-dicarbonylruthenium (Ii)] with nucleotides. Inorg Chimica Acta. 1988;151:243-8.

Quick et al., Pentacarbonylmanganese halides. In Inorganic Syntheses, vol. 19. Duward F. Shriver., Ed. Inorganic Syntheses, Inc. 1979:158-63.

(56) References Cited

OTHER PUBLICATIONS

Rattan et al., Mechanism of internal anal sphincter relaxation by CORM-1, authentic CO, and NANC nerve stimulation. Am J Physiol Gastrointest Liver Physiol. Sep. 2004;287(3):G605-11.
Rehder et al., 55Mn NMR characteristics of carbonylmanganese complexes with hetero-substituted dithioformato-, thioformamido- and thioformamide ligands [1]. Inorg Chim Acta. 1983;73:243-7. Abstract only.
Reimann et al., Reactions of metal carbonyls. Part III. Steric and stereochemical limitations of higher substitution of manganese carbonyl bromide. J Chem Soc Dalton Trans. 1973;841-6. Abstract only.
Rodella et al., Carbon monoxide and biliverdin prevent endothelial cell sloughing in rats with type I diabetes. Free Radic Biol Med. Jun. 15, 2006;40(12):2198-205. Epub Mar. 20, 2006.
Rutkowska-Zbik et al., Theoretical density functional theory studies on interactions of small biologically active molecules with isolated heme group. J Comput Chem. Mar. 2007;28(4):825-31.
Ryan et al., Renal vascular responses to CORM-A1 in the mouse. Pharmacol Res. Jul. 2006;54(1):24-9. Epub Mar. 9, 2006.
Ryter et al., Carbon monoxide in biology and medicine. Bioessays. Mar. 2004;26(3):270-80.
Ryter et al., Carbon monoxide: to boldly go where NO has gone before. Sci STKE. Apr. 20, 2004;2004(230):RE6. Review.
Ryter et al., Heme oxygenase/carbon monoxide signaling pathways: regulation and functional significance. Mol Cell Biochem. May-Jun. 2002;234-235(1-2):249-63. Review.
Ryter et al., Heme oxygenase-1/carbon monoxide: from basic science to therapeutic applications. Physiol Rev. Apr. 2006;86(2):583-650. Review.
Sacerdoti et al., Treatment with tin prevents the development of hypertension in spontaneously hypertensive rats. Science. Jan. 20, 1989;243(4889):388-90.
Sacks et al., Comparative bioavailability of elemental iron powders for repair of iron deficiency anemia in rats. Studies of efficacy and toxicity of carbonyl iron. Am J Clin Nutr. Apr. 1978;31(4):566-71.
Salazar-Salinas et al., Molecular biosensor based on a coordinated iron complex. J Chem Phys. Mar. 14, 2009;130(10):105101.
Sammut et al., Carbon monoxide is a major contributor to the regulation of vascular tone in aortas expressing high levels of haeme oxygenase-1. Br J Pharmacol. Dec. 1998;125(7):1437-44.
Sandborn, Strategies for targeting tumour necrosis factor in IBD. Best Pract Res Clin Gastroenterol. Feb. 2003;17(1):105-17. Review.
Sandouka et al., Carbon monoxide-releasing molecules (CO-RMs) modulate respiration in isolated mitochondria. Cell Mol Biol (Noisy-le-grand). Sep. 30, 2005;51(4):425-32.
Sandouka et al., Treatment with CO-RMs during cold storage improves renal function at reperfusion. Kidney Int. Jan. 2006;69(2):239-47.
Santucci et al., Pentoxifylline prevents indomethacin induced acute gastric mucosal damage in rats: role of tumour necrosis factor alpha. Gut. Jul. 1994;35(7):909-15.
Sarady et al., Carbon monoxide protection against endotoxic shock involves reciprocal effects on iNOS in the lung and liver. FASEB J. May 2004;18(7):854-6. Epub Mar. 4, 2004.
Sato et al., Carbon monoxide generated by heme oxygenase-1 suppresses the rejection of mouse-to-rat cardiac transplants. J Immunol. Mar. 15, 2001;166(6):4185-94.
Sato et al., Heme oxygenase-1 or carbon monoxide prevents the inflammatory response associated with xenograft rejection. Acta Haematologica. 13th Symposium on Mol Biol Hematopoiesis and Treatment of Leukemia and Cancer. New York, NY. Jul. 14-18, 2000. Released Jul. 2000;103(Supp11): Abstract 345, p. 87.
Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.
Sawle et al., Homocysteine attenuates endothelial haem oxygenase-1 induction by nitric oxide (NO) and hypoxia. FEBS Lett. Nov. 23, 2001;508(3):403-6.
Schmidt et al., Manganese(I) and rhenium(I) pentacarbonyl(Trifluoromethanesulfatonato) complexes. In Inorganic Syntheses, Ed. Herbert D. Kaesz. Inorganic Syntheses, Inc. vol. 26. 1989:113-17.
Schubert, The action of carbon monoxide on iron and cobalt complexes of cysteine. Carbon Monixide on Iron and Cobalt Cysteine Complexes. 1933;55:4563-70.
Severin et al., Metal complexes of biologically important ligands. LXX. Synthesis, stereochemistry and reactions of ruthenium (II) and osmium (II) complexes with .alpha.-amino carboxylates. 1994; 127(4): 615-620. English abstract provided.
Shapiro, Carbonyl-trapping therapeutic strategies. Am J Ther. Sep. 1998;5(5):323-53. Review.
Shiohira et al., Protective effect of carbon monoxide donor compounds in endotoxin-induced acute renal failure. Am J Nephrol. 2007;27(5):441-6. Epub Jul. 12, 2007.
Silver et al., Mossbauer studies on protoprophyrin IX iron (II) solutions containing sulphur ligands and their carbonyl adducts. Inorg Chimica Acta. 1984;9:279-83.
Siow et al., Heme oxygenase-carbon monoxide signalling pathway in atherosclerosis: anti-atherogenic actions of bilirubin and carbon monoxide? Cardiovasc Res. Feb. 1999;41(2):385-94.
Sjöstrand, Endogenous formation of carbon monoxide in man under normal and pathological conditions. Scan J Clin Lab Invest. 1949;1:201-14.
Skattebøl et al., Synthesis of (±)-Lineatin, an aggregation pheromone component of Trypodendron lineatum. Acta Chem Scand B. 1985;39:291-304.
Soares et al., Expression of heme oxygenase-1 can determine cardiac xenograft survival. Nat Med. Sep. 1998;4(9):1073-7.
Song et al., Carbon monoxide inhibits human airway smooth muscle cell proliferation via mitogen-activated protein kinase pathway. Am J Respir Cell Mol Biol. Nov. 2002;27(5):603-10.
Song et al., Carbon monoxide inhibits T lymphocyte proliferation via caspase-dependent pathway. J Immunol. Jan. 15, 2004;172(2):1220-6.
Spector, Review: Oxidative stress and disease. J Ocul Pharmacol Ther. Apr. 2000;16(2):193-201. Review. Abstract only.
Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.
Srisook et al., Role of NO in enhancing the expression of HO-1 in LPS-stimulated macrophages. Methods Enzymol. 2005;396:368-77.
Staal et al., The syntheses and coordination properties of M(CO)3X(DAB) (M=Mn, Re; X=Cl, Br, I; Dab=1,4-diazabutadiene). J Organometal Chem. May 1, 1979;170( 2):235-45. Abstract only.
Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.
Stanford et al., Carbon monoxide inhibits endothelin-1 release by human pulmonary artery smooth muscle cells. Eur J Pharmacol. Feb. 23, 2004;486(3):349-52.
Stanford et al., Heme oxygenase is expressed in human pulmonary artery smooth muscle where carbon monoxide has an anti-proliferative role. Eur J Pharmacol. Jul. 25, 2003;473(2-3):135-41.
Stec et al., Heme oxygenase-1 induction does not improve vascular relaxation in angiotensin II hypertensive mice. Am J Hypertens. Feb. 2008;21(2):189-93. Epub Jan. 3, 2008.
Stein et al., Administration of a CO-releasing molecule induces late preconditioning against myocardial infarction. J Mol Cell Cardiol. Jan. 2005;38(1):127-34. Epub Dec. 8, 2004.
Stone et al., Soluble guanylate cyclase from bovine lung: activation with nitric oxide and carbon monoxide and spectral characterization of the ferrous and ferric states. Biochemistry. May 10, 1994;33(18):5636-40.
Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

(56) References Cited

OTHER PUBLICATIONS

Suematsu et al., Carbon monoxide: an endogenous modulator of sinusoidal tone in the perfused rat liver. J Clin Invest. Nov. 1995;96(5):2431-7.
Sun et al., Attenuation of leukocytes sequestration by carbon monoxide-releasing molecules: liberated carbon monoxide in the liver of thermally injured mice. J Burn Care Res. Jan.-Feb. 2007;28(1):173-81.
Sun et al., CO-releasing molecules (CORM-2)-liberated CO attenuates leukocytes infiltration in the renal tissue of thermally injured mice. Int J Biol Sci. Jun. 16, 2008;4(3):176-83.
Sun et al., Preconditioning of carbon monoxide releasing molecule-derived CO attenuates LPS-induced activation of HUVEC. Int J Biol Sci. Aug. 22, 2008;4(5):270-8.
Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.
Suzuki et al., Activated platelets in ulcerative colitis enhance the production of reactive oxygen species by polymorphonuclear leukocytes. Scand J Gastroenterol. Dec. 2001;36(12):1301-6. Abstract only.
Szakács-Schmidt et al., Iron (II) thiolates as reversible carbon monoxide carriers. Inorg Chimica Acta. 1992;198-200:401-5.
Szallasi et al., Dialdehyde sesquiterpenes and other terpenoids as vanilloids. Eur J Pharmacol. Aug. 28, 1998;356(1):81-9. Abstract only.
Taillé et al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.
Takács et al., Synthesis and molecular structure of carbonyl derivatives of Iron (II) thiolates containing nitrogen-donor ligands. Inorg Chemica Acta. 1989;166:39-46.
Tamaki, Role of second messenger gases in ischemia and reperfusion injury. Low Temp Med. 2001;27(1):1-5. English abstract provided.
Tamm et al., Isocyanide Complexes of Molybdenum. Comprehensive Organometallic Chemistry III Elsevier, Oxford. 2007;5:486-96.
Tayem et al., Protection against cisplatin-induced nephrotoxicity by a carbon monoxide-releasing molecule. Am J Physiol Renal Physiol. Apr. 2006;290(4):F789-94. Epub Nov. 15, 2005.
Tenhunen et al., Microsomal heme oxygenase. Characterization of the enzyme. J Biol Chem. Dec. 10, 1969;244(23):6388-94.
Tilg et al., Antitumour necrosis factor therapy in Crohn's disease. Expert Opin Biol Ther. Oct. 2002;2(7):715-21. Review. Abstract only.
Togane et al., Protective roles of endogenous carbon monoxide in neointimal development elicited by arterial injury. Am J Physiol Heart Circ Physiol. Feb. 2000;278(2):H623-32.
Tomita et al., Structure and reaction of bis(L-cysteinato)dicarbonyliron(II). Inorg Nucl Chem Lett. 1968;4:715-8.
Treichel et al., Synthesis and reactivity of bridging thiolato-manganese carbonyl complexes, Et4N[Mn2(µ-SR)3(CO)6]. J Organometall Chem. Sep. 10, 1985;292(3):385-93.
Tsuburai et al., The role of heme oxygenase in pulmonary circulation. Low Temp Med. 2001;27(1):28-35. English abstract provided.
Urban et al., Metal complexes of biologically important ligands, LXXXVII α-amino carboxylate complexes of palladium(II), iridium(III) and ruthenium (II) from chloro-bridged ortho-metallated metal compounds and [(OC)3Ru(Cl)(µ-Cl)]2. J Organomett Chem. 1996;517:191-200.
Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.
Van Staveren et al., Spectroscopic Properties, Electrochemistry, and Reactivity of Mo0, MoI, and MoII Complexes with the [Mo(bpa)(CO)3] Unit [bpa=bis(2-picolyl)amine] and Their Application for the Labelling of Peptides. Eur J Inorg Chem. 2002;6:1518-29.
Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.
Vannacci et al., The effect of a carbon monoxide-releasing molecule on the immunological activation of guinea-pig mast cells and human basophils. Inflamm Res. 2004;53 Suppl 1:S09-10.
Varadi et al., Beneficial effects of carbon monoxide-releasing molecules on post-ischemic myocardial recovery. Life Sci. Apr. 3, 2007;80(17):1619-26. Epub Feb. 2, 2007.
Vera et al., Protective effect of carbon monoxide-releasing compounds in ischemia-induced acute renal failure. J Am Soc Nephrol. Apr. 2005;16(4):950-8. Epub Feb. 23, 2005.
Verma et al., Carbon monoxide: a putative neural messenger. Science. Jan. 15, 1993;259(5093):381-4.
Verona et al., Regioselectivity in the nucleophilic functionalization of xanthene complexes of Mn(CO)3. J Organelle Chem. Nov. 1, 1996;524(1-2)71-80.
Viswanathamurthi et al., Synthesis, characterization and biocidal studies of ruthenium (II) carbonyl complexes containing tetradentate Schiff bases. Transition Metal Chemistry. 1999; 24(6):638-641.
Volkl et al., Fixation of Metallo Nitrile Ylides and Metallo Nitrile Imines as Ligands in Transition Metal Complexes. Z. Anorg. Allg. Chem. 2010;636:1339-46.
Volti et al., Carbon monoxide signaling in promoting angiogenesis in human microvessel endothelial cells. Antiox Redox Signal. May 2005;7(5-6):704-10.
Vreman et al., Determination of carbon monoxide (CO) in rodent tissue: effect of heme administration and environmental CO exposure. Anal Biochem. Jun. 15, 2005;341(2):280-9. Abstract only.
Vulapalli et al., Cardioselective overexpression of HO-1 prevents I/R-induced cardiac dysfunction and apoptosis. Am J Physiol Heart Circ Physiol. Aug. 2002;283(2):H688-94.
Waibel et al., Stable one-step technetium-99m labeling of His-tagged recombinant proteins with a novel Tc(I)-carbonyl complex. Nat Biotechnol. Sep. 1999;17(9):897-901.
Wang et al., A correlation of the visible and Soret spectra of dioxygen- and carbon monoxideheme complexes and five-coordinate heme complexes with the spectra of oxy-, carboxy-, and deoxyhemoglobins. Biochemistry. Oct. 30, 1979;18(22):4960-77.
Wang et al., Carbon monoxide-induced vasorelaxation and the underlying mechanisms. Br J Pharmacol. Jul. 1997;121(5):927-34.
Wang et al., Preconditioning limits mitochondrial Ca(2+) during ischemia in rat hearts: role of K(ATP) channels. Am J Physiol Heart Circ Physiol. May 2001;280(5):H2321-8.
Wang et al., Syntheses and evaluation of drug-like properties of CO-releasing molecules containing ruthenium and group 6 metal. Eur J Med Chem. Mar. 3, 2014;74:199-215. Epub Jan. 9, 2014.
Wang et al., The chemical modification of KCa channels by carbon monoxide in vascular smooth muscle cells. J Biol Chem. Mar. 28, 1997;272(13):8222-6.
Weigel et al., Inhibition of DNA replication in *Escherichia coli* by cyanide and carbon monoxide. J Biol Chem. Nov. 10, 1975;250(21):8536-42.
Willis et al., Heme oxygenase: a novel target for the modulation of the inflammatory response. Nat Med. Jan. 1996;2(1):87-90.
Winter, Hexacorbonyls and carbonyl complexes of carbon sigma-bonded ligands of chromium, molybdenum and tungsten in Comprehensive Organometallic Chemistry II. Pergamon, Oxford. Section 3.6. 1995; vol. 5:161-5.
Wu et al., Carbon monoxide: endogenous production, physiological functions, and pharmacological applications. Pharmacol Rev. Dec. 2005;57(4):585-630. Review.
Wu et al., Different mechanisms underlying the stimulation of K(Ca) channels by nitric oxide and carbon monoxide. J Clin Invest. Sep. 2002;110(5):691-700.
Xi et al., Carbon monoxide activates KCa channels in newborn arteriole smooth muscle cells by increasing apparent Ca2+ sensi-

(56) References Cited

OTHER PUBLICATIONS tivity of alpha-subunits. Am J Physiol Heart Circ Physiol. Feb. 2004;286(2):H610-8. Epub Oct. 16, 2003.

Xu et al., A facile method for synthesis of (R)-(−)- and (S)-(+)-homocitric acid lactones and related α-hydroxy dicarboxylic acids from d- or l-malic acid. Tetrahedron Lett. May 30, 2005;46(22):3815-18. Abstract only.

Yachie et al., Oxidative stress causes enhanced endothelial cell injury in human heme oxygenase-1 deficiency. J Clin Invest. Jan. 1999;103(1):129-35.

Yan et al., Cytotoxicity of rhenium(I) alkoxo and hydroxo carbonyl complexes in murine and human tumor cells. Pharmazie. Apr. 2000;55(4):307-13.

Yeo et al., YC-1: a potential anticancer drug targeting hypoxia-inducible factor 1. J Natl Cancer Inst. Apr. 2, 2003;95(7):516-25.

Yet et al., Cardiac-specific expression of heme oxygenase-1 protects against ischemia and reperfusion injury in transgenic mice. Circ Res. Jul. 20, 2001;89(2):168-73.

Yet et al., Induction of heme oxygenase-1 expression in vascular smooth muscle cells. A link to endotoxic shock. J Biol Chem. Feb. 14, 1997;272(7):4295-301.

Zhang et al., Carbon monoxide inhibition of apoptosis during ischemia-reperfusion lung injury is dependent on the p38 mitogen-activated protein kinase pathway and involves caspase 3. J Biol Chem. Jan. 10, 2003;278(2):1248-58. Epub Oct. 23, 2002.

Zimmerman et al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

U.S. Appl. No. 15/218,564, filed Jul. 25, 2016, Rodrigues et al.

U.S. Appl. No. 14/848,047, filed Sep. 8, 2015, Blättler et al.

PCT/US2012/047661, Nov. 23, 2012, International Search Report and Written Opinion.

PCT/US2012/047661, Jan. 30, 2014, International Preliminary Report on Patentability.

\* cited by examiner

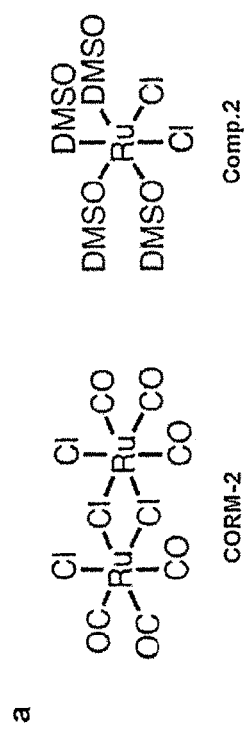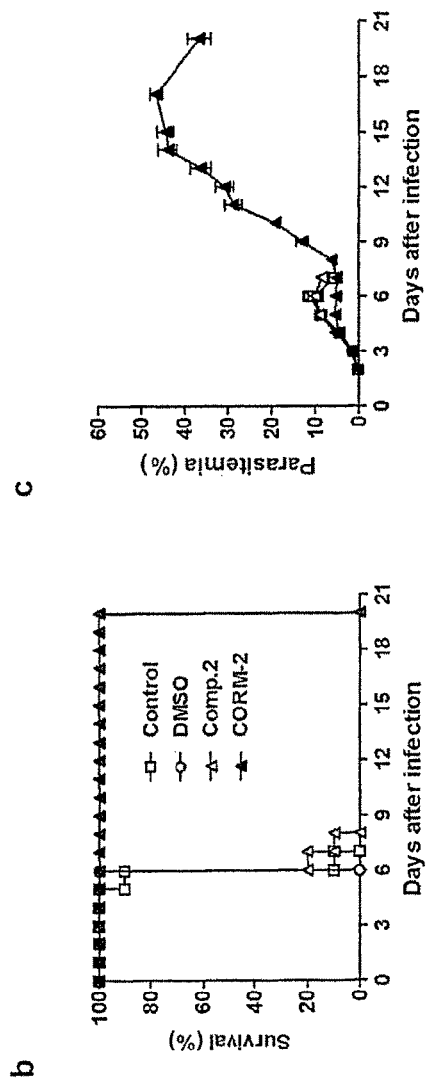
Figures 1a-1c

SEQUENCE LISTING

<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
gttggataca ggccagactt tgttg                                              25

<210> SEQ ID NO 2
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 2
gattcaacct tgcgctcatc ttaggc                                             26

<210> SEQ ID NO 3
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 3
tctcaggggg tcaggtc                                                       17

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
ggagcggtgt ctgggatg                                                      18

<210> SEQ ID NO 5
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 5
aagcattaaa taaagcgaat acatccttac                                         30

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 6
ggagattggt tttgacgttt atgtg                                              25

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
tgctcgagat gtgatgaagg                                                    20

<210> SEQ ID NO 8
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 8
tcccctgttg actggtcatt                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
cacactgcat cttggctttg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
tctggctctg caggattttc                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
cgaaggtggt tcttctgagc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
gtctgctgag acccctcttg                                               20
```

RUTHENIUM CARBON MONOXIDE RELEASING MOLECULES AND USES THEREOF

RELATED APPLICATIONS

The present application is a continuation of and claims priority under 35 U.S.C. §120 to U.S. patent application, U.S. Ser. No. 14/234,024, filed Apr. 10, 2014, now U.S. Pat. No. 9,062,089, which is a national stage filing under 35 U.S.C. §371 of International PCT Application, PCT/US2012/047661, filed Jul. 20, 2012, which claims priority under 35 U.S.C. §119(e) to U.S. provisional application, U.S. Ser. No. 61/510,136, filed Jul. 21, 2011, the entire contents of each of which are incorporated herein by reference.

BACKGROUND OF THE INVENTION

Malaria remains a devastating global health problem, resulting in up to one million annual deaths (see, e.g., Sachs, Science (2002) 298:122-124; Mwangi et al., J Infect Dis (2005) 191:1932-1939; Snow et al., Nature (2005) 434:214-217; World Health Organization (WHO). World malaria report 2008). Plasmodium falciparum causes the most severe forms of malaria infection such as cerebral malaria (CM) and acute lung injury (ALI) (see, e.g., Trampuz et al., Crit Care (2003) 7:315-323). The case-fatality rate in severe malaria treated with either artemisinin or quinine derivatives remains unacceptably high. Cerebral malaria is among the deadliest syndromes with 13-21% mortality even after anti-malarial treatment (see, e.g., Idro et al., Lancet Neurol (2005) 4:827-840).

Primary therapy with quinine or artemisinin derivatives is generally effective in controlling P. falciparum parasitemia, but mortality from cerebral malaria (CM) and other forms of severe malaria remains unacceptably high. In an effort to reduce malaria-related mortality adjunctive/adjuvant therapies complementing treatment to an anti-malarial therapy have been suggested and tested (see, e.g., John et al., Expert Rev Anti Infect Ther (2010) 8:997-1008). Heme oxygenase-1 (HO-1) is a key protective gene against the development of CM in mice (see, e.g., Pamplona et al., Nat Med (2007) 13:703-710). Inhalation of carbon monoxide (CO), one of the end-products of HO-1 activity, fully prevented cerebral malaria and malaria-associated acute lung injury (M-AALI) incidence in C57BL/6 mice (see, e.g., Pamplona supra; Epiphanio et al., PLoS Pathog (2010) 6:e1000916). Research conducted in other experimental models has further shown that HO-1/CO display cytoprotective and anti-inflammatory properties that are beneficial for the resolution of acute inflammation (see, e.g., Hayashi et al., Circ Res (1999) 85:663-671; Lee et al., Nat Med (2002) 8:240-246).

Carbon monoxide holds great promise as a therapeutic agent (see, e.g., Motterlini et al., Nat Rev Drug Discov (2010) 9:728-743). However, the safety and practicability of the application of carbon monoxide gas in the clinic remains questionable due to its toxicity and the need for highly controlled medical facilities. Thus, CO-releasing molecules (CO-RMs) have been put forward as a valid alternative. Among the early-developed and still widely used CO-RMs in experimental models are the lipid-soluble CORM-2, $[Ru(CO)_3Cl_2]_2$ and the water-soluble CORM-3, $[Ru(CO)_3Cl_2(H_2NCH_2CO)_2]$. Both CORM-2 and CORM-3 do not elevate the carboxyhemoglobin (COHb) levels in blood after in vivo administration (see, e.g., Clark et al., Circ Res (2003) 93:2-8). Substantial protective effects similar to those observed for CO inhalation have been reported using CORM-2 and CORM-3 in various experimental models of disease, such as bacterial infection, vascular dysfunction, and thermal- and ischemia-reperfusion injury (see, e.g., Clark supra; Alcaraz et al., Curr Pharm Des (2008) 14:465-72); Kim et al., Annu Rev Pharmacol Toxicol (2006) 46:411-449). Moreover, CORM-2 lacks desirable drug-like properties, such as water solubility and stability in its own solvent (see Motterlini et al., Circ Res (2002) 90:e17-e24). Thus, there continues to remain a need for the development of new CORMs as therapeutic agents.

SUMMARY OF THE INVENTION

The present application provides inventive ruthenium CORM compounds, pharmaceutical compositions thereof, and methods of their use and treatment. Such compounds have been found useful in the treatment of malaria, for example, as adjuvants in combination with anti-malarial agents. Such compounds have also also been found to induce the expression of HO-1, and thus are also deemed useful in the treatment of various inflammatory conditions, such as acute lung injury and acute respiratory distress syndrome, which optionally is associated with a malaria infection.

For example, in one aspect, provided is a compound of the Formula (I):

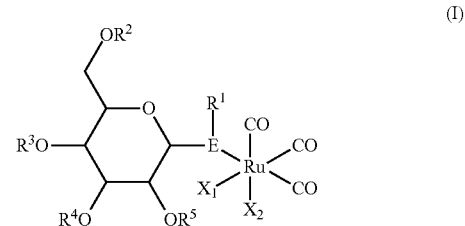

or a salt, isomer, hydrate, or solvate thereof, or combination thereof;

wherein:

E is —S— or —Se—;

$R^1$ is hydrogen or $C_{1-6}$alkyl;

each instance of $R^2$, $R^3$, $R^4$, and $R^5$ is, independently, hydrogen, a carbohydrate group, or an oxygen protecting group; and $X_1$ and $X_2$ are each independently halogen.

In certain embodiments, E is —S—. In certain embodiments, E is —Se—. In certain embodiments, $R^1$ is hydrogen. In certain embodiments, $R^1$ is —$CH_3$. In certain embodiments, each instance of $R^2$, $R^3$, $R^4$, and $R^5$ is hydrogen. In certain embodiments, $X_1$ and $X_2$ are each —Cl.

In certain embodiments, the substituent:

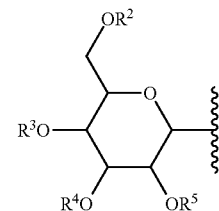

is a stereoisomer selected from the group consisting of:

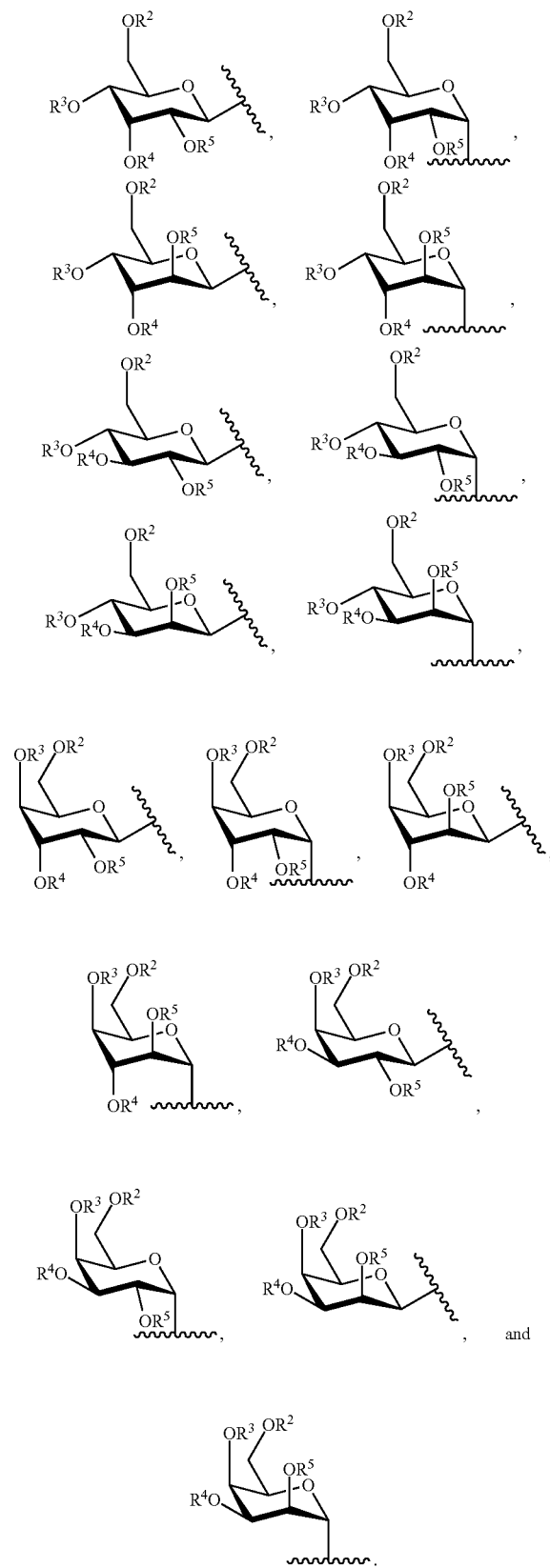

In certain embodiments, the compound is a stereoisomer of Formula (I-a):

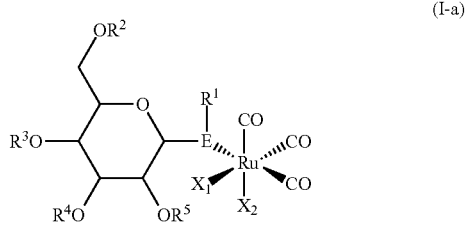

(I-a)

or a salt, isomer, hydrate, or solvate thereof, or combination thereof.

In certain embodiments, the compound is a stereoisomer of Formula (I-b):

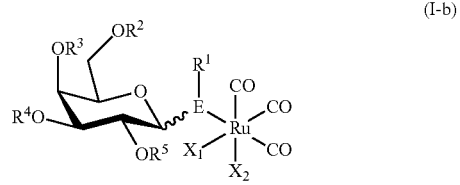

(I-b)

or a salt, isomer, hydrate, or solvate thereof, or combination thereof.

In certain embodiments, the compound is:

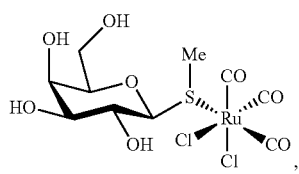

also referred to herein as Compound 1.

In another aspect, provided is a pharmaceutical composition comprising a compound of Formula (I), or a salt, isomer, hydrate, or solvate thereof, or combination thereof, and a pharmaceutically acceptable excipient. In certain embodiments, the compound is Compound 1.

In yet another aspect, provided is a method of treating a malaria infection comprising administering an effective amount of a compound of Formula (I), or a salt, isomer, hydrate, or solvate thereof, or combination thereof, to a subject in need thereof. In certain embodiments, the compound is Compound 1. In certain embodiments, the malaria infection is severe malaria due to a *Plasmodium* infection. In certain embodiments, the *Plasmodium* infection is a *Plasmodium falciparum* infection, a *Plasmodium vivax* infection, a *Plasmodium malariae* infection, a *Plasmodium ovale* infection, or a *Plasmodium knowlesi* infection. In certain embodiments, the malaria infection is cerebral malaria (CM). In certain embodiments, the malaria infection is pregnancy-associated malaria (PAM). In certain embodiments, the subject has a suspected or confirmed malaria infection. In certain embodiments, the method prevents malaria infection in the subject, e.g., in certain embodiments, the method inhibits infection of the subject by malaria parasites. In certain embodiments, the malarial infection is a recrudescent (relapsed) malarial infection.

In certain embodiments, the method further comprises administering one or more additional agents. In certain embodiments, the agent is an anti-inflammatory agent. In certain embodiments, the agent is an anti-malarial agent. In certain embodiments, the compound of Formula (I), or a salt, isomer, hydrate, or solvate thereof, is used in combination with an anti-malarial agent. In certain embodiments, the compound of Formula (I), or a salt, isomer, hydrate, or solvate thereof, is useful as an anti-malarial adjuvant, e.g., the compound of Formula (I) is an agent which potentiates the therapeutic effect of the anti-malarial agent when used in combination. In certain embodiments, the agent is an activator of pyruvate dehydrogenase. In certain embodiments, the agent is selected from the group consisting of quinazolines, protein kinase inhibitors, quinines, tetracyclines, aminoquinolones, biquanides, cinchona alkaloids, sulfonamides, artemisinins, clindamycin, dapsone, atovaquone, lumefantrine, piperaquine, pyronaridine, atovaquone, mefloquine, pyrimethamine, halofantrine, TNF inhibitors, iron chelators, dexamethasone, intravenous immunoglobulin, curdlan sulfate, dichloroacetate, and salts thereof; CO gas, and combinations thereof. In certain embodiments, the agent is artesunate. In certain embodiments, is the agent is CO gas In certain embodiments, the agent is a TNF inhibitor. In certain embodiments, the agent is an iron chelator. In certain embodiments, the agent is dichloroacetate. In certain embodiments, the agent is a protein kinase inhibitor (e.g., genistein).

In yet another aspect, provided is a method of treating acute lung injury comprising administering an effective amount of a compound of Formula (I), or a salt, isomer, hydrate, or solvate thereof, or combination thereof, to a subject in need thereof. In certain embodiments, the acute lung injury is malaria-associated acute lung injury. In certain embodiments, the compound is Compound 1.

In still yet another aspect, provided is a method of treating acute respiratory distress syndrome comprising administering an effective amount of a compound of Formula (I), or a salt, isomer, hydrate, or solvate thereof, or combination thereof, to a subject in need thereof. In certain embodiments, the acute respiratory distress syndrome is associated with a malaria infection. In certain embodiments, the compound is Compound 1.

The details of one or more embodiments of the invention are set forth herein. Other features, objects, and advantages of the invention will be apparent from the description, the figures, the examples, and the claims.

BRIEF DESCRIPTION OF THE DRAWINGS

FIGS. 1a-1c. CORM-2 protects from ECM. FIG. 1a: Chemical structure of tricarbonyldichlororuthenium (II) dimer (CORM-2) and tetrakis(dimethylsulfoxide) dichlororuthenium(II) (Compound 2). FIGS. 1b-1c: Effect of CORM-2 on survival (FIG. 1b) and parasitemia (FIG. 1c) of P. berghei ANKA GFP-infected C57BL/6 mice. Infected mice (Control) treated with DMSO, Compound 2 and CORM-2 between day 2 and day 3 after infection (2×/day). (□), Infected (Control) (n=10), (○) DMSO (n=10), (Δ) ALF466 (n=10) and (▲) CORM-2 (n=10). Parasitemias are shown as mean±standard error of the mean. Shaded area indicates the time period of Compound 2 and CORM-2 administration. Data are representative of 2 independent experiments.

FIG. 2a: Schematic synthesis of tricarbonylchloro (thiogalactopyranoside)ruthenium(II) (Compound 1). FIGS. 2b-2c: Concentration of Ru and CO in organs of non-infected (NI) mice after i.v. treatment with Compound 2, inactive form, and Compound 1. Results are shown as mean concentration±standard error of the mean (n=3-5 animals per group). Effect of Compound 1 on survival (FIG. 2d) and parasitemia (FIG. 2d) of P. berghei ANKA GFP-infected C57BL/6. Treatment with Compound 2 and Compound 1 between day 2 and day 3 after infection (2×/day). (□), Control (n=10), (Δ) Compound 2 (n=10) and (●) Compound 1 (n=10). Parasitemias are shown as mean±standard error of the mean. Shaded area indicates the time period of Compound 2 and Compound 1 administration. Data are representative from 3 independent experiments. FIG. 2f: COHb measurement in whole blood of non-infected (NI), P. berghei ANKA-infected C57BL/6 mice (Control) and treated with Compound 2, Compound 1 and CO (250 ppm, 24 h), at day 3 after infection. NI (n=6); Control (n=4); Compound 2 (n=4); Compound 1 (n=4) and CO (n=4). Error bars represent standard error of the mean. Compound 1 induces the expression of HO-1 in the liver (FIG. 2g) and brain (FIG. 2h) of P. berghei ANKA infected C57BL/6 mice, respectively, at day 3 after infection, the last day of treatment with Compound 2 and Compound 1. HO-1 mRNA was quantified by qRT-PCR. NI (n=4-6); I+Compound 2 (n=4) and I+Compound 1 (n=3-5).

FIGS. 3f-3i: Semi-quantification of histological findings in hematoxylin and eosin stained brain sections, analyzed at the same time as in FIGS. 3a-3e, using a blinded score system. Dot plots compare the number of animals assigned the severity scores from 1 (less severe) to 3 (most severe) in infected, infected Compound 2-treated and Compound 1-treated mice. Images are representative of 3-8 mice. The bar corresponds to 100 μm.

FIG. 4a: Survival (%) of P. berghei ANKA-infected DBA/2 mice receiving no treatment or treated i.v. with Compound 2 and Compound 1 between day 2 and day 3 after infection (2×/day). I (n=5); I+Compound 2 (n=9); I+Compound 1 (n=7). Parasitemias are shown as mean±standard error of the mean. FIG. 4b: Levels of VEGF protein in the plasma of P. berghei ANKA-infected DBA mice with ALI symptoms, Compound 2-treated and Compound 1 compared to non-infected mice (NI). NI (n=3), I (ALI) (n=3); I+Compound 2 (n=5) and I+Compound 1 (n=5). Results are shown as mean concentration±standard error of the mean. FIGS. 4c-4e: Semi-quantification of the histological findings in hematoxylin and eosin stained lung sections, analyzed at the same time as in FIG. 4b, using a blinded score system. Dot plots show the number of animals assigned the severity scores from 1 (less severe) to 3 (most severe) in infected (ALI), infected Compound 2-treated (ALI) and Compound 1-treated mice. Images are representative of 4-6 mice. The bar corresponds to 100 μm.

FIG. 5a: Survival of C57BL/6 mice infected with *P. berghei* ANKA GFP, treated with AS (d5-d6), or AS (d5-d6) and Compound 1 (d5-d9) or AS (d5-d6) and Compound 1 (d8-d9). Survival was monitored over a 24-day period. Data representative of 2 independent experiments. The treatment with AS started when the infected mice (control) showed a score of 1 (ruffled fur), initial stage of ECM. Overall survival was significantly improved by Compound 1 treatment (P<0.01). FIG. 5*b*: Parasitemia from mice infected with *P. berghei* ANKA (control), infected and treated with AS (d5-d6) (AS) (Δ), infected and treated with AS (d5-d6) and Compound 1 (d5-d9) (AS+Compound 1) (▲), and infected treated with AS (d5-d6) and Compound 1 (d8-d9) (AS→Compound 1) (●) are shown. (□) Control (n=5), (Δ) AS (n=11), (▲) AS+Compound 1 (d5-d9) (n=6), (●) AS→Compound 1 (d8-d9) (n=9). Data represent mean±standard error of the mean. FIG. 5*c*: To each of the ECM clinical stage (no detectable symptoms, ruffled fur, ruffled fur and motor impairment, respiratory distress and convulsions and/or coma) was given a score (0, 1, 2, 3, and 4). Mice were graphically ranked based on symptoms presented after day 5 of infection.

FIG. 11*a*: ESI-MS spectrum of native lysozyme C (2 mg/mL in $H_2O$). FIG. 11*b*: ESI-MS of lysozyme (2.0 mg/mL) when incubated with CORM-3 (10 equiv) in $H_2O$ for 10 minutes at room temperature. FIG. 11*c*: ESI-MS of lysozyme (2.0 mg/mL) when incubated with CORM-3 (10 equiv) in $H_2O$ for 1 hour at room temperature.

FIG. 11*d*: ESI-MS of lysozyme (2.0 mg/mL) when incubated with $Ru(CO)_3Cl_2$(Gal-S-Me) (Compound 1) (10 equiv) in $H_2O$ for 10 minutes at room temperature. FIG. 11*e*: ESI-MS of lysozyme (2.0 mg/mL) when incubated with $Ru(CO)_3Cl_2$(Gal-S-Me) (Compound 1) (10 equiv) in $H_2O$ for 1 hour at room temperature.

FIGS. 12*a*-12*b*: Effect of CORM-3 on survival (FIG. 12*a*) and parasitemia (FIG. 12*b*) of *P. berghei* ANKA GFP-infected C57BL/6 mice. Infected mice (Control), Compound 2 and CORM-3 between day 2 and day 3 after infection (2×/day). (□), Infected (Control) (n=5), (Δ) ALF466 (n=5) and (▲) CORM-3 (n=4). Parasitemias are shown as mean±standard error of the mean. Data are representative of 1 independent experiment.

DETAILED DESCRIPTION OF CERTAIN EMBODIMENTS OF THE INVENTION

Figures 2A, 2B, 2C, 2D, 2E:
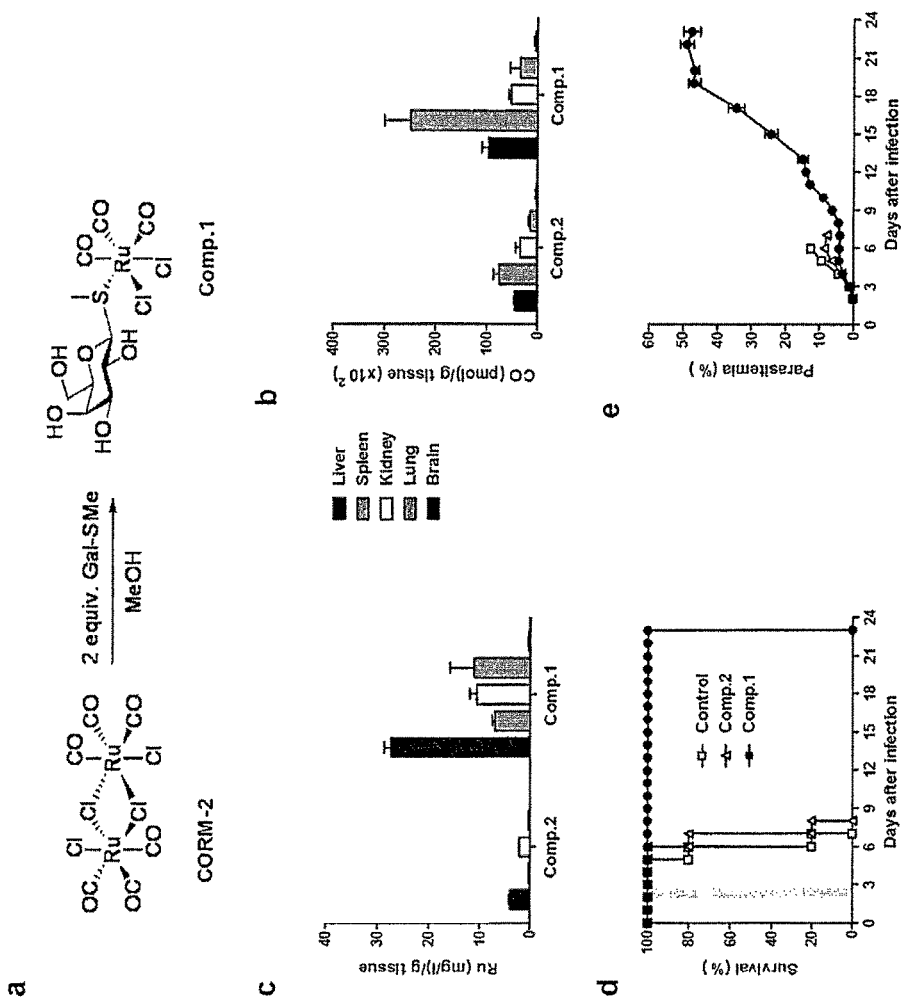
FIGS. 2a-2h. Compound 1 is a liver-targeted water-soluble CORM and protects from ECM.

The present invention is based on the discovery that the addition of a thiosugar ligand to the CORM-2 complex, $[Ru(CO)_3Cl_2]_2$, provides a new complex with improved drug-like properties, such as improved stability, aqueous solubility, and/or tissue specificity. An exemplary compound is the thiomethyl-beta-galactose derivative, referred to herein as Compound 1, which has demonstrated improved stability, improved aqueous solubility, and improved specificity for the liver compared to CORM-2. CO delivered from Compound 1 can induce similar protection as was seen with CO gas therapy, but without the toxic effects (elevated COHb levels) of CO inhalation. The inventors discovered that Compound 1 is an effective therapy in the protection from death caused by malaria infection, such as cerebral malaria (CM). Remarkably, the present invention demonstrates that Compound 1 is an effective adjunctive agent when used in combination with another anti-malarial agent, e.g., artesunate, after onset of the malarial infection. The inventors further discovered that Compound 1 induces the expression of HO-1, and thus the inventors envision Compound 1 as an effective therapy in the amelioration of inflammatory conditions, e.g., acute lung injury and acute respiratory distress syndrome, which optionally may be associated with malaria infection. The inventors envision that certain bioisosters of the thiosugar ligand, such as selenosugars, may optionally be found useful in the practice of one or more of the inventive methods.

Thus, in one aspect, the present invention provides inventive compounds of the Formula (I):

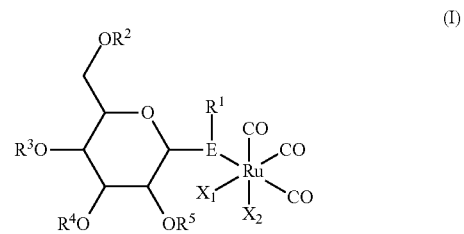
(I)

or salts, isomers, hydrates, or solvates thereof, or combinations thereof;

wherein:

E is —S— or —Se—;

$R^1$ is hydrogen or $C_{1-6}$alkyl;

each instance of $R^2$, $R^3$, $R^4$, and $R^5$ is, independently, hydrogen, a carbohydrate group, or an oxygen protecting group; and $X_1$ and $X_2$ are each independently halogen.

The present invention also provides pharmaceutical compositions comprising a compound of Formula (I) or a salt, isomer, hydrate, or solvate thereof, or combination thereof. The present invention further provides methods of use and treatment of a compound of Formula (I), or a salt, isomer, hydrate, or solvate thereof, or combination thereof, or a pharmaceutical composition thereof.

Specific chemical terms are described below and herein. General principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. General principles of organometallic chemistry is described in S. W. Kirtley in *Comprehensive Organometallic Chemistry I* (G. Wilkinson, F. G. A. Stone, W. Abel Eds, Vol 3, 1080, Pergamon, Oxford 1982; M. J. Winter in *Comprehensive Organometallic Chemistry II* (W. Abel, F. G. A. Stone, G. Wilkinson Eds), Vol 5, 163, Pergamon, Oxford 1995; and M. Tamm, R. J. Baker, in *Comprehensive Organometallic Chemistry III* (R. H. Crabtree and D. M. P. Mingos Eds), Vol 5, 391, Elsevier, Oxford 2007.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl.

When a range of values is listed, it is intended to encompass each value and sub-range within the range. For example "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl.

"Alkyl" refers to a radical of a straight-chain or branched saturated hydrocarbon group having from 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl groups include methyl (C1), ethyl (C2), n-propyl (C3), isopropyl (C3), n-butyl (C4), tert-butyl (C4), sec-butyl (C4), iso-butyl (C4), n-pentyl (C5), 3-pentanyl (C5), amyl (C5), neopentyl (C5), 3-methyl-2-butanyl (C5), tertiary amyl (C5), and n-hexyl (C6). Additional examples of alkyl groups include n-heptyl (C7), n-octyl (C8), n-nonyl (C9), n-decyl (C10), and the like.

"Carbocyclyl" refers to a radical of a non-aromatic cyclic hydrocarbon group having from 3 to 4 ring carbon atoms ("C3-4 carbocyclyl") and zero heteroatoms in the non-aromatic ring system. Exemplary C3-4 carbocyclyl groups include, without limitation, cyclopropyl (C3), cyclopropenyl (C3), cyclobutyl (C4), and cyclobutenyl (C4). In some embodiments, "carbocyclyl" is a monocyclic, saturated carbocyclyl group having from 3 to 4 ring carbon atoms ("C3-4 cycloalkyl").

"Alkenyl" refers to a radical of a straight-chain or branched hydrocarbon group having from 2 to 10 carbon atoms and one or more carbon-carbon double bonds ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like.

"Alkynyl" refers to a radical of a straight-chain or branched hydrocarbon group having from 2 to 10 carbon atoms and one or more carbon-carbon triple bonds ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like. Examples of C2-6 alkenyl groups include the aforementioned C2-4 alkynyl groups as well as pentynyl (C5), hexynyl (C6), and the like. Additional examples of alkynyl include heptynyl (C7), octynyl (C8), and the like.

"Heterocyclyl" refers to a radical of a 5- to 10-membered non-aromatic ring system having ring carbon atoms and 1 to 4 ring heteroatoms, wherein each heteroatom is independently selected from nitrogen, oxygen, and sulfur ("5-10 membered heterocyclyl"). In heterocyclyl groups that contain one or more nitrogen atoms, the point of attachment can be a carbon or nitrogen atom, as valency permits. A heterocyclyl group can either be monocyclic or bicyclic, and can be saturated or can contain one or more carbon-carbon double or triple bonds. Heterocyclyl bicyclic ring systems can include one or more heteroatoms in one or both rings. Heterocyclyl also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, and the like.

"Aryl" refers to a radical of a monocyclic or bicyclic 4n+2 aromatic ring system (e.g., having 6 or 10 π electrons shared in a cyclic array) having 6-10 ring carbon atoms and zero heteroatoms provided in the aromatic ring system ("C6-10 aryl"). In some embodiments, an aryl group has 6 ring carbon atoms ("C6 aryl"; e.g., phenyl). In some embodiments, an aryl group has 10 ring carbon atoms ("C10 aryl"; e.g., naphthyl such as 1-naphthyl and 2-naphthyl). Aryl also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. Heteroaryl also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl moieties) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ l, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two RC groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, 13 P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_1$-6 perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^{30}$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —C1), bromine (bromo, —Br), or iodine (iodo, —I).

Exemplary nitrogen atom substituents include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. In certain embodiments, the nitrogen atom substituent is a nitrogen protecting group. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate (—Ac), chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, two proximal oxygens atoms are protected as a cyclic acetal, e.g., 1,2- or 1,3-diols may be protected as a isopropylidinyl, a cycloalkylidene ketal (e.g., cyclopentylidene or cyclohexylidene), a benzylidene acetal (e.g., p-methoxybenzylidine), a carbonate, a silylene (e.g., di-t-butylsilylene, 1,3-(1,1,1,3,3)-tetraisopropyldisiloxanylide), a 1,3-dioxolanyl, or a 1,3-dioxanyl group.

"Salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, see Berge et al., describes pharmaceutically acceptable salts in detail in *J. Pharmaceutical Sciences* (1977) 66:1-19, and P. Heinrich Stahl and Camille G. Wermuth, Handbook of Pharmaceutical Salts: Properties, Selection and Use. International Union of Pure and Applied Chemistry, Wiley-VCH 2002. Pharmaceutically acceptable salts include pharmaceutically acceptable acid addition salts (i.e., a salt formed from the compound upon addition of an acid) and pharmaceutically acceptable base addition salts (i.e., a salt formed from the compound upon addition of a base). Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate salts. Pharmaceutically acceptable base addition salts include, but are not limited to, aluminum, calcium, lithium, magnesium, potassium, sodium, zinc, and quaternary amine salts.

An "isomer" includes any and all geometric isomers and stereoisomers. For example, "isomers" include cis- and trans-isomers, E- and Z— isomers, R— and S— enantiomers, diastereomers, (D)-isomers, (L)-isomers, fac and mer isomers, racemic mixtures thereof, and other mixtures thereof, as falling within the scope of the invention.

A "hydrate" refers to a compound of the present disclosure non-covalently associated with one or more molecules of water. Likewise, a "solvate" refers to a compound of the present disclosure non-covalently associated with one or more molecules of an organic solvent.

A "carbohydrate group" or a "carbohydrate" refers to a monosaccharide or a polysaccharide (e.g., a disaccharide or oligosaccharide). Exemplary monosaccharides include, but are not limited to, allose, altrose, glucose, mannose, gulose, idose, galactose, talose, ribose, arabinose, xylose, and lyxose. Disaccharides are two joined monosaccharides.

Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

Embodiments of the Compound of Formula (I)

As generally described above, the present invention provides compounds of Formula (I):

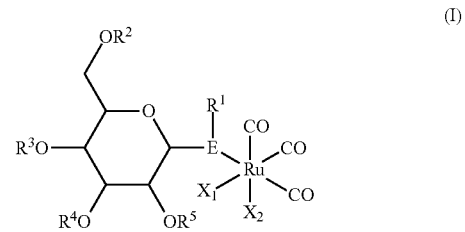

or salts, isomers, hydrates, or solvates thereof, or combinations thereof;
wherein:
E is —S— or —Se—;
$R^1$ is hydrogen or $C_{1-6}$alkyl;
each instance of $R^2$, $R^3$, $R^4$, and $R^5$ is, independently, hydrogen, a carbohydrate group, or an oxygen protecting group; and
$X_1$ and $X_2$ are each independently halogen.

In certain embodiments, E is —S—. In certain embodiments, E is —Se—.

In certain embodiments, $R^1$ is $C_{1-3}$alkyl. In certain embodiments, $R^1$ is $C_{1-4}$alkyl. In certain embodiments, $R^1$ is $C_{1-5}$alkyl. In certain embodiments, $R^1$ is $C_{1-2}$alkyl. In certain embodiments, $R^1$ is $C_{2-6}$alkyl. In certain embodiments, $R^1$ is $C_{2-5}$alkyl. In certain embodiments, $R^1$ is $C_{2-4}$alkyl. In certain embodiments, $R^1$ is $C_{2-3}$alkyl. In certain embodiments, $R^1$ is $C_{3-6}$alkyl. In certain embodiments, $R^1$ is $C_{3-5}$alkyl. In certain embodiments, $R^1$ is $C_{3-4}$alkyl. In certain embodiments, $R^1$ is $C_{4-6}$alkyl. In certain embodiments, $R^1$ is $C_{4-5}$alkyl. In certain embodiments, $R^1$ is $C_1$alkyl. In certain embodiments, $R^1$ is $C_2$alkyl. In certain embodiments, $R^1$ is $C_3$alkyl. In certain embodiments, $R^1$ is $C_4$alkyl. In certain embodiments, $R^1$ is $C_5$alkyl. In certain embodiments, $R^1$ is $C_6$alkyl. In certain embodiments, $R^1$ is selected from the group consisting of —$CH_3$, —$CH_2CH_3$, —$(CH_2)_2CH_3$, —$(CH_2)_3CH_3$, —$(CH_2)_4CH_3$, —$(CH_2)_5CH_3$, —$CH(CH_3)_2$, —$C(CH_3)_3$, —$CH(CH_3)CH_2CH_3$, —$CH_2CH(CH_3)CH_3$, —$CH(CH_3)(CH_2)_2CH_3$, —$CH_2CH(CH_3)CH_2CH_3$, —$(CH_2)_2CH(CH_3)_2$, —$CH(CH_3)(CH_2)_3CH_3$, —$CH_2CH(CH_3)(CH_2)_2CH_3$, and —$(CH_2)_3CH(CH_3)_2$. In certain embodiments, $R^1$ is —$CH_3$ or —$CH_2CH_3$. In certain embodiments, $R^1$ is —$CH_3$.

As generally described above, each instance of $R^2$, $R^3$, $R^4$, and $R^5$ is, independently, hydrogen, a carbohydrate group, or an oxygen protecting group.

In certain embodiments, at least one instance of $R^2$, $R^3$, $R^4$, and $R^5$ is, independently, hydrogen. In certain embodiments, at least two instances of $R^2$, $R^3$, $R^4$, and $R^5$ is, independently, hydrogen. In certain embodiments, at least three instances of $R^2$, $R^3$, $R^4$, and $R^5$ is, independently, hydrogen. In certain embodiments, each instance of $R^2$, $R^3$, $R^4$, and $R^5$ is, independently, hydrogen.

In certain embodiments, at least one instance of $R^2$, $R^3$, $R^4$, and $R^5$ is, independently, a carbohydrate group. In certain embodiments, at least two instances of $R^2$, $R^3$, $R^4$, and $R^5$ is, independently, a carbohydrate group. In certain embodiments, at least three instances of $R^2$, $R^3$, $R^4$, and $R^5$ is, independently, a carbohydrate group. In certain embodiments, each instance of $R^2$, $R^3$, $R^4$, and $R^5$ is, independently, a carbohydrate group. Exemplary carbohydrate groups are described above and herein. For example, in certain embodiments, the carbohydrate group is a monosaccaharide, e.g., glucose or galactose. In certain embodiments, the carbohydrate is a disaccharide, e.g., sucrose. In certain embodiments, the carbohydrate is an oligiosaccharide.

In certain embodiments, at least one instance of $R^2$, $R^3$, $R^4$, and $R^5$ is, independently, an oxygen protecting group. In certain embodiments, at least two instances of $R^2$, $R^3$, $R^4$, and $R^5$ is, independently, an oxygen protecting group. In certain embodiments, at least three instances of $R^2$, $R^3$, $R^4$, and $R^5$ is, independently, an oxygen protecting group. In certain embodiments, each instance of $R^2$, $R^3$, $R^4$, and $R^5$ is, independently, an oxygen protecting group. Exemplary carbohydrate groups are described above and herein. For example, in certain embodiments, the oxygen protecting group is selected from the group consisting of —$R^{aa}$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the oxygen protecting group is —C(=O)$R^{aa}$, wherein $R^{aa}$ is $C_{1-10}$ alkyl. In certain embodiments, the oxygen protecting group is —C(=O)CH$_3$.

As generally described above, $X_1$ and $X_2$ are each independently halogen. In certain embodiments, $X_1$ and $X_2$ are each independently selected from the group consisting of bromo, iodo, or chloro. In certain embodiments, $X_1$ and $X_2$ are each independently selected from the group consisting of bromo or chloro. In certain embodiments, at least one $X_1$ and $X_2$ is iodo. In certain embodiments, at least one $X_1$ and $X_2$ is bromo. In certain embodiments, at least one $X_1$ and $X_2$ is chloro. In certain embodiments, $X_1$ and $X_2$ are each iodo. In certain embodiments, $X_1$ and $X_2$ are each bromo. In certain embodiments, $X_1$ and $X_2$ are each chloro.

In certain embodiments, the sugar substituent:

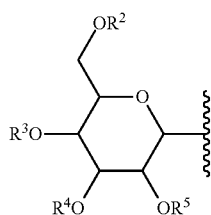

is a stereoisomer selected from the group consisting of:

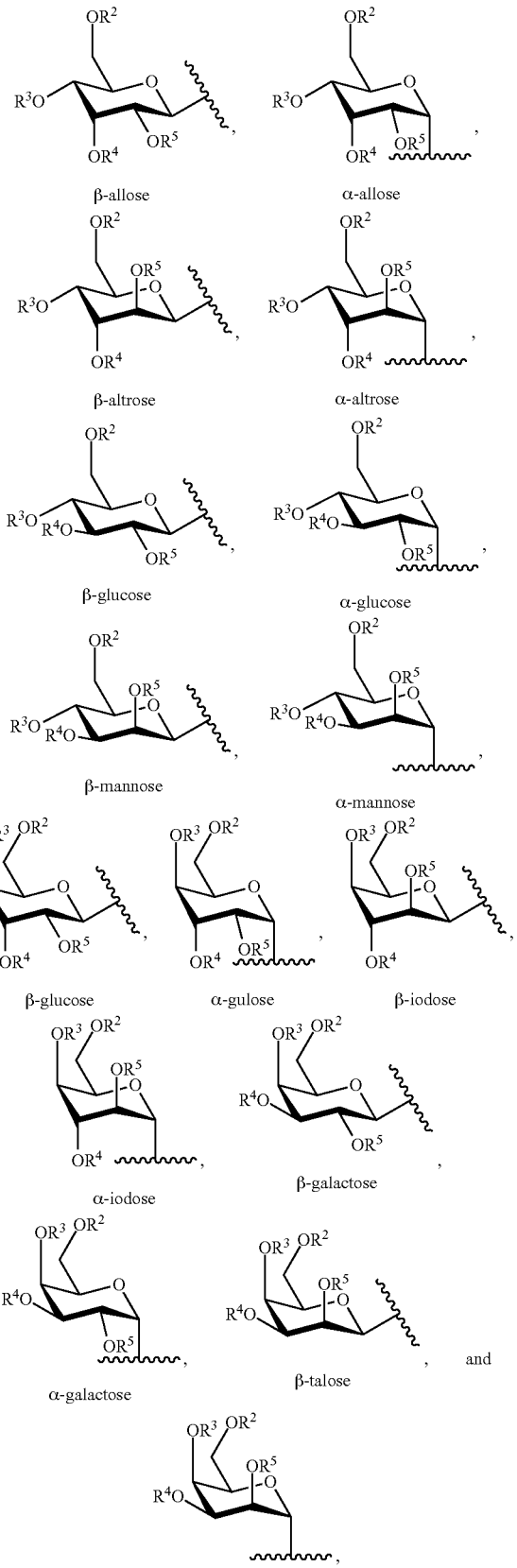

wherein $R^2$, $R^3$, $R^4$, and $R^5$ are as defined herein.

α-talose

Alpha and beta designate the stereochemistry at the anomeric carbon C1 of the sugar substituent. In certain embodiments, the sugar substituent is alpha at the anomeric carbon. In certain embodiments, the sugar substituent is beta at the anomeric carbon.

In certain embodiments, the sugar substituent is selected from the group consisting of α-glucose, β-glucose, α-mannose, β-mannose, α-galactose, and β-galactose. In certain embodiments, the sugar substituent is selected from the group consisting of α-glucose and β-glucose. In certain embodiments, the sugar substituent is selected from the group consisting of α-mannose and β-mannose. In certain embodiments, the sugar substituent is selected from the group consisting of α-galactose and β-galactose. In certain embodiments, the sugar substituent is α-glucose. In certain embodiments, the sugar substituent is β-glucose. In certain embodiments, the sugar substituent is α-mannose. In certain embodiments, the sugar substituent is β-mannose. In certain embodiments, the sugar substituent is α-galactose. In certain embodiments, the sugar substituent is β-galactose.

In certain embodiments, the ruthenium complex:

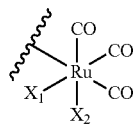

is a stereoisomer of formula:

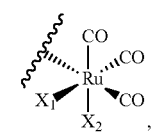
(i)

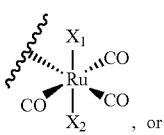
(ii) , or

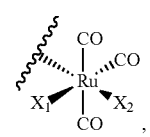
(iii) , wherein $X_1$ and $X_2$ are as defined herein.

In certain embodiments, the ruthenium complex is a stereoisomer of formula (i). In certain embodiments, the ruthenium complex is a stereoisomer of formula (ii). In certain embodiments, the ruthenium complex is a stereoisomer of formula (iii).

In certain embodiments of Formula (I), wherein the ruthenium complex is a stereoisomer of formula (i), the compound is of Formula (I-a):

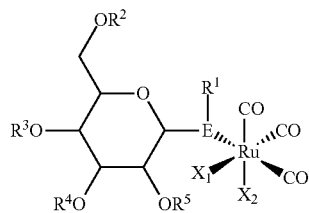
(I-a)

or a salt, isomer, hydrate, or solvate thereof, or combination thereof, wherein E, $R^1$, $R^2$, $R^3$, $R^4$, $R^5$, $X_1$, and $X_2$, are as defined herein. In certain embodiments, E is —S—. In certain embodiments, E is —Se—. In certain embodiments, $R^1$ is hydrogen. In certain embodiments, $R^1$ is —CH$_3$. In certain embodiments, each instance of $R^2$, $R^3$, $R^4$, and $R^5$ is hydrogen. In certain embodiments, $X_1$ and $X_2$ are each chloro (—Cl). In certain embodiments, the sugar substituent α-galactose or β-galactose. In certain embodiments, the sugar substituent is α-galactose. In certain embodiments, the sugar substituent is β-galactose.

In certain embodiments of Formula (I), wherein the sugar substituent is α-galactose or β-galactose, the compound is of Formula (I-b):

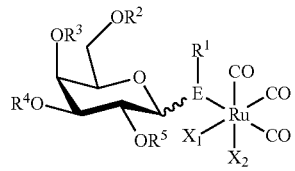
(I-b)

or a salt, isomer, hydrate, or solvate thereof, or combination thereof, wherein E, $R^1$, $R^2$, $R^3$, $R^4$, $R^5$, $X_1$, and $X_2$, are as defined herein. In certain embodiments, E is —S—. In certain embodiments, E is —Se—. In certain embodiments, $R^1$ is hydrogen. In certain embodiments, $R^1$ is —CH$_3$. In certain embodiments, each instance of $R^2$, $R^3$, $R^4$, and $R^5$ is hydrogen. In certain embodiments, $X_1$ and $X_2$ are each chloro (—Cl). In certain embodiments, the ruthenium complex is a stereoisomer of formula (i). In certain embodiments, the sugar substituent is α-galactose. In certain embodiments, the sugar substituent is β-galactose.

In certain embodiments of Formula (I-b), wherein the ruthenium complex is a stereoisomer of formula (i), the compound is of Formula (I-c):

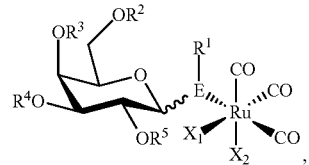
(I-c)

or a salt, hydrate, or solvate thereof, or combination thereof, wherein E, $R^1$, $R^2$, $R^3$, $R^4$, $R^5$, $X_1$, and $X_2$, are as defined herein. In certain embodiments, E is —S—. In certain embodiments, E is —Se—. In certain embodiments, $R^1$ is hydrogen. In certain embodiments, $R^1$ is —CH$_3$. In certain embodiments, each instance of $R^2$, $R^3$, $R^4$, and $R^5$ is hydrogen. In certain embodiments, $X_1$ and $X_2$ are each chloro (—Cl). In certain embodiments, the sugar substituent is α-galactose. In certain embodiments, the sugar substituent is β-galactose.

In certain embodiments of Formula (I-c), wherein $X_1$ and $X_2$ are each chloro (—Cl), the compound is of Formula (I-d):

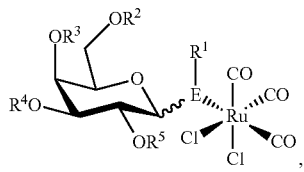
(I-d)

or a salt, hydrate, or solvate thereof, or combination thereof, wherein E, $R^1$, $R^2$, $R^3$, $R^4$, and $R^5$, are as defined herein. In certain embodiments, E is —S—. In certain embodiments, E is —Se—. In certain embodiments, $R^1$ is hydrogen. In certain embodiments, $R^1$ is —$CH_3$. In certain embodiments, each instance of $R^2$, $R^3$, $R^4$, and $R^5$ is hydrogen. In certain embodiments, the sugar substituent is α-galactose. In certain embodiments, the sugar substituent is β-galactose.

In certain embodiments of Formula (I-d), wherein $R^1$ is —$CH_3$, the compound is of Formula (I-e):

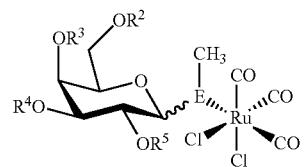
(I-e)

or a salt, hydrate, or solvate thereof, or combination thereof, wherein E, $R^2$, $R^3$, $R^4$, and $R^5$, are as defined herein. In certain embodiments, E is —S—. In certain embodiments, E is —Se—. In certain embodiments, each instance of $R^2$, $R^3$, $R^4$, and $R^5$ is hydrogen. In certain embodiments, the sugar substituent is α-galactose. In certain embodiments, the sugar substituent is β-galactose.

In certain embodiments of Formula (I-e), wherein the sugar substituent is β-galactose, the compound is of Formula (I-f):

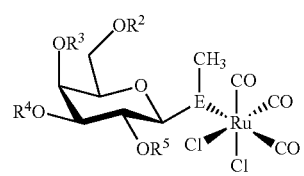
(I-f)

or a salt, hydrate, or solvate thereof, or combination thereof, wherein E, $R^2$, $R^3$, $R^4$, and $R^5$, are as defined herein. In certain embodiments, E is —S—. In certain embodiments, E is —Se—. In certain embodiments, each instance of $R^2$, $R^3$, $R^4$, and $R^5$ is hydrogen.

In certain embodiments of Formula (I-f), wherein E is —S— and each instance of $R^2$, $R^3$, $R^4$, and $R^5$ is hydrogen, the compound is:

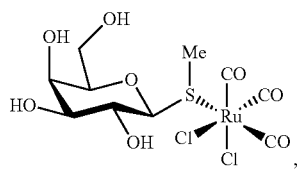

also referred to herein as Compound 1, or a hydrate or solvate thereof, or combination thereof.

Pharmaceutical Compositions and Administration

The present invention provides pharmaceutical compositions comprising a compound of the present invention, e.g., a compound of Formula (I) or a salt, isomer, hydrate, or solvate thereof, or combination thereof, as described herein, and a pharmaceutically acceptable excipient. In certain embodiments, the compound of the present invention is provided in an effective amount in the pharmaceutical composition. In certain embodiments, the effective amount is a therapeutically effective amount. In certain embodiments, the effective amount is a prophylactically effective amount.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. *acacia*, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of adminsitration.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 1 mg to about 3000 mg, about 1 mg to about 2000 mg, about 1 mg to about 1000 mg, about 1 mg to about 100 mg, about 10 mg to about 100 mg, or about 20 mg to about 100 mg, of a compound per unit dosage form.

In certain embodiments, the compounds of the invention may be administered at dosage levels sufficient to deliver from about 1 mg/kg to about 100 mg/kg, from about 0.01 mg/kg to about 100 mg/kg, preferably from about 0.1 mg/kg to about 100 mg/kg, preferably from about 0.5 mg/kg to about 100 mg/kg, from about 10 mg/kg to about 100 mg/kg, from about 20 mg/kg to about 100 mg/kg, and more preferably from about 25 mg/kg to about 100 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. Therapeutically active agents include but are not limited to small organic molecules (i.e., having a molecular weight under 800 g/mol) such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small organic molecules linked to proteins, glycoproteins, steroids, nucleic acids, DNAs, RNAs, nucleotides, nucleosides, oligonucleotides, antisense oligonucleotides, lipids, hormones, vitamins, vaccines, gases, and cells. Specific examples of therapeutically active agents are further described herein. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects. In general, each particular agent will be administered at a dose and/or on a time schedule determined for that agent. In will further be appreciated that the additional agents utilized in this combination can be administered together in a single pharmaceutical composition or administered separately in different pharmaceutical compositions. The particular combination to employ in a regimen will take into account compatibility of the inventive compound with the additional agent and/or the desired therapeutic effect to be achieved. In general, it is expected that additional agents utilized in combination be utilized at levels that do not exceed the levels at which they are utilized individually. In some embodiments, the levels utilized in combination will be lower than those utilized individually.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Uses

The present invention also provides methods of use and treatment of compounds of the present invention, e.g., compounds of Formula (I), or salts, isomers, hydrates, or solvates thereof, or combinations thereof, as described herein.

A "subject" to which administration is contemplated is a human subject,e.g., a male or female human of any age group, e.g., a pediatric subject (e.g, infant, child, adolescent) or adult subject (e.g., young adult, middle-aged adult or senior adult.

"Treat," "treating" and "treatment" contemplate an action that occurs while a subject is suffering from a condition which reduces the severity of the condition or symptoms associated with the condition, or retards or slows the progression of the condition or symptoms associated with the condition ("therapeutic treatment"), and also contemplates an action that occurs before a subject begins to suffer from the condition and which inhibits or reduces the severity of the condition or symtoms associated with the condition ("prophylactic treatment"). For example, "treating a malarial infection" involves administering a compound of the present invention to a subject having malarial infection, or a subject exhibiting one or more symptoms of malarial infection (e.g., cyclical occurrence of sudden coldness followed by rigor and then fever and sweating, joint pain, vomiting, anemia, hemoglobinuria, retinal damage, and/or convulsions) ("therapeutically treating a malarial infection"), and also involves preventative care, such as administering a compound of the present invention to a subject at risk of malarial infection ("prophylactically treating a malarial infection").

An "effective amount" of a compound refers to an amount sufficient to elicit the desired biological response, i.e., treating the condition (e.g., a malarial infection, an inflammatory condition). As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of a compound of the present invention, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutically active agent.

A "prophylactically effective amount" of a compound is an amount sufficient to prevent a condition, or one or more symptoms associated with the condition or prevent its recurrence. A prophylactically effective amount of a compound means an amount of a compound of the present invention, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

In certain embodiments, the present invention provides a method of treating a malaria infection comprising administering an effective amount of a compound of Formula (I), or a salt, isomer, hydrate, or solvate thereof, or combination thereof, to a subject in need thereof.

In certain embodiments, the present invention provides a method of treating a malaria infection comprising instructing a subject in need thereof to administer an effective amount of a compound of Formula (I), or a salt, isomer, hydrate, or solvate thereof, or combination thereof.

In certain embodiments, the present invention provides a compound of Formula (I) or a salt, isomer, hydrate, or solvate thereof, or combination thereof, for use in treating a malaria infection.

In certain embodiments, the effective amount is a therapeutically effective amount. For example, in certain embodiments, the method improves survival from a malarial infection in the subject. In certain embodiments, the subject has a suspected or confirmed malaria infection.

In certain embodiments, the effective amount is a prophylatically effective amount. For example, in certain embodiments, the method prevents or reduces the likelihood of malaria infection in the subject, e.g., in certain embodiments, the method comprises administering a compound of Formula (I) to a subject in need thereof in an amount sufficient to prevent or reduce the likelihood of an infection by malaria parasites. In certain embodiments, the subject is at risk to malaria infection (e.g., has been exposed to another subject who has a suspected or confirmed malaria infection).

In certain embodiments, the malaria infection is severe malaria due to a *Plasmodium* infection. In certain embodiments, the *Plasmodium* infection is a *Plasmodium falciparum* infection, a *Plasmodium vivax* infection, *Plasmodium malariae* infection, a *Plasmodium ovale* infection, or a *Plasmodium knowlesi* infection. In certain embodiments, the *Plasmodium* infection is a *Plasmodium falciparum* infection. In certain embodiments, the *Plasmodium* infection is a *Plasmodium vivax* infection. In certain embodiments, the *Plasmodium* infection is a *Plasmodium malariae* infection. In certain embodiments, the *Plasmodium* infection is a *Plasmodium ovale* infection. In certain embodiments, the *Plasmodium* infection is a *Plasmodium knowlesi* infection.

In certain embodiments, the malarial infection is cerebral malaria (CM). In certain embodiments, the malaria infection is pregnancy-associated malaria (PAM). In certain embodiments, the malarial infection is a recrudescent (relapsed) malarial infection.

Compounds of the present invention have been found to induce the expression of HO-1, and thus compounds of the present invention are also contemplated useful in the treatment of an inflammatory condition, such as ALI and ARDS, which is not necessarily associated with malaria infection. However, in certain embodiments, the subject suffering from a malaria infection is further suffering from an inflammatory condition, e.g. acute lung injury (ALI) or acute respiratory distress syndrome (ARDS). In certain embodiments, the inflammatory condition is complication of the malaria infection. ARDS is considered to be the most severe form of ALI in malaria. ALI and ARDS have been described as complications arising in subjects suffering from malaria infection, and could be associated with cerebral malaria; see, e.g., Mohan et al., *J Vector Borne Dis*. (2008) 45:179-93; Taylor et al., *Treat Respir Med* (2006) 5: 419-28.

Thus, in certain embodiments, the present invention provides a method of treating acute lung injury (ALI) comprising administering an effective amount of a compound of Formula (I), or a salt, isomer, hydrate, or solvate thereof, or combination thereof, to a subject in need thereof.

In certain embodiments, the present invention provides a method of treating acute lung injury comprising instructing a subject in need thereof to administer an effective amount of a compound of Formula (I), or a salt, isomer, hydrate, or solvate thereof, or combination thereof.

In certain embodiments, the present invention provides a compound of Formula (I) or a salt, isomer, hydrate, or solvate thereof, or combination thereof, for use in treating acute lung injury.

In certain embodiments, the acute lung injury is malaria-associated acute lung injury (M-AALI).

In certain embodiments, the effective amount is a therapeutically effective amount. For example, in certain embodiments, the method improves survival from malaria associated acute lung injury in the subject. In certain embodiments, the subject has a suspected or confirmed malaria infection.

In certain embodiments, the effective amount is a prophylatically effective amount. For example, in certain embodiments, the method prevents or reduces the likelihood of malaria-associated acute lung injury in the subject.

In certain embodiments, the present invention provides a method of treating acute respiratory distress syndrome (ARDS) comprising administering an effective amount of a compound of Formula (I), or a salt, isomer, hydrate, or solvate thereof, or combination thereof, to a subject in need thereof.

In certain embodiments, the present invention provides a method of treating acute respiratory distress syndrome (ARDS) comprising instructing a subject in need thereof to administer an effective amount of a compound of Formula (I), or a salt, isomer, hydrate, or solvate thereof, or combination thereof.

In certain embodiments, the present invention provides a compound of Formula (I) or a salt, isomer, hydrate, or solvate thereof, or combination thereof, for use in treating acute respiratory distress syndrome (ARDS).

In certain embodiments, the acute respiratory distress syndrome is malaria-associated acute respiratory distress syndrome (M-AARDS).

In certain embodiments, the effective amount is a therapeutically effective amount. For example, in certain embodiments, the method improves survival from malaria-associated acute respiratory distress syndrome in the subject. In certain embodiments, the subject has a suspected or confirmed malaria infection.

In certain embodiments, the effective amount is a prophylatically effective amount. For example, in certain embodiments, the method prevents or reduces the likelihood of malaria-associated acute respiratory distress syndrome in the subject.

In any of the above described methods, one or more additional therapeutic agents (also referred to as the "agent") may be administered concurrently with, prior to, or subsequent to, the compound of Formula (I), as described herein. The agent may be added at the same time as the compound of Formula (I) (simultaneous administration), before or after administration of the compound of Formula (I) (sequential administration), or any combination thereof. For example, in certain embodiments, the agent is administered first, followed by simultaneous administration of the agent and the compound of Formula (I). In certain embodiments, the compound of Formula (I) is administered first, followed by simultaneous administration of the agent and the compound of Formula (I). In any of the above embodiments, either the agent or the compound of Formula (I) may be further administered alone after the simultaneous administration.

In certain embodiments, the compound of Formula (I) is used as an adjunctive agent in combination with one or more additional therapeutic agents (also referred to as the "primary agent"). As used herein, an "adjunctive agent" or "adjuvant" is an agent used in combination with the primary agent, and which potentiates the therapeutic effects (e.g., either additively or synergistically) of the primary agent. Adjunctive therapy includes administration of the adjuvant before administration of the primary agent ("neoadjuvant therapy"), during administration of the primary agent ("concomitant" or "concurrent systemic adjuvant therapy"), or after administration of the primary agent.

In certain embodiments, the additional therapeutic agent is an anti-malarial agent. Exemplary anti-malarial agents include, but are not limited to, quinazolines (e.g., 2,4-diamino-6(3,4-dichlorobenzyamine quinazoline (PAM1392), 2,4-diamino-6-[93,4-dichiorobenzyl0-nitroso-amino]-quinazoline (CI-679)). protein kinase inhibitors (e.g., radicicol, staurosproin, genistein, methyl 2,5-dihydroxycinnamate, tyrphostin B44 and B46, lavendustin A and RO3), quinines (e.g., quinine, quinacrine, quinidine), tetracyclines (e.g., doxycycline, tetracycline), aminoquinolones (e.g., amodiaquine, chloroquine, hydroxychloroquine, primaquine), biquanides (e.g., proguanil, chlorproquanil), cinchona alkaloids (e.g., cinchoine, cinchonidine), sulfonamides (e.g., sulfonamide, sulfadoxine, sulfamethoxypridazine), artemisinins (e.g., artemisinin, artemether, dihydroartemesinin, artesunate, artether), clindamycin, dapsone, atovaquone, lumefantrine, piperaquine, pyronaridine, atovaquone, mefloquine, pyrimethamine, halofantrine, and salts thereof. In certain embodiments, the anti-malarial agent is an artemisinin compound (e.g., artemisinin, artemether, dihydroartemesinin, artesunate, artether). In certain embodiments, the anti-malarial agent is artemisinin, artemether, dihydroartemesinin, artesunate, or artether. In certain embodiments, the anti-malarial agent is artemisinin. In certain embodiments, the anti-malarial agent is genistein.

In certain embodiments, the additional therapeutic agent is an anti-inflammatory agent. Exemplary anti-inflammatory agents include, but are not limited to TNF inhibitors (e.g., monoclonal antibodies such as infliximab, adalimumab, certolizumab pegol, and golimumab; a circulating receptor fusion protein such as etanercept; xanthine derivatives such as pentoxifylline; Bupropion); iron chelators (e.g., desferrioxamine); dexamethasone; intravenous immunoglobulin; curdlan sulfate; salts thereof; and CO gas. In certain embodiments, the anti-inflammatory agent is CO gas.

In certain embodiments, the additional therapeutic agent is an activator of pyruvate dehydrogenase, e.g., dicloroacetate (DCA), DCA has been shown to reduce hyperlactatemia and acidosis (e.g., increased blood acidity) of severe malaria (see, e.g., Krishna et al, *Br. J. Clin. Pharmacol.* (1996) 41:29-34).

EXAMPLES

In order that the invention described herein may be more fully understood, the following examples are set forth. It should be understood that these examples are for illustrative purposes only and are not to be construed as limiting this invention in any manner.

Example 1

CORM-2 Protects Against ECM Development

It has previously been shown that administration of CO by inhalation protects *P. berghei* ANKA infected C57BL/6 mice from developing ECM (see, e.g., Pamplona et al. *Nat Med* (2007) 13:703-710). The inventors questioned whether CO-RMs could mimic the protection conferred by CO inhalation in *P. berghei* ANKA infection. To this end, a known ruthenium CORM, $Ru(CO)_3Cl_2$, also referred to herein as CORM-2, was tested on different schedules of treatment and doses in *P. berghei* ANKA infected C57BL/6 mice (data not shown). As negative control, a CO-depleted analogue of CORM-2, $[Ru(DMSO)_4Cl_2]$(also referred to herein as "Compound 2") where all CO ligands of Ru(II) are replaced by DMSO ligands (FIG. 1a) was used. Treatment twice daily with CORM-2 between days 2 and 3 after infection prevented death or symptoms of ECM in all infected C57BL/6 mice ($P<0.001$ versus DMSO or Compound 2-treated). These mice developed hyperparasitemia and anemia (>30% infected red blood cells) and were sacrificed 3 weeks after infection (FIG. 1b,c). In contrast, mice in the Compound 2-treated ("mock-treated" mice) and DMSO-treated control groups died between days 6 and 7 after infection with ECM symptoms, such as hemi- or paraplegia, head deviation, tendency to roll over on stimulation, ataxia and convulsions (FIG. 1b). A statistically significant delay in parasitemia was also observed after day 5 of infection in mice treated with CORM-2 ($P<0.01$) (FIG. 1c).

Figure 12:
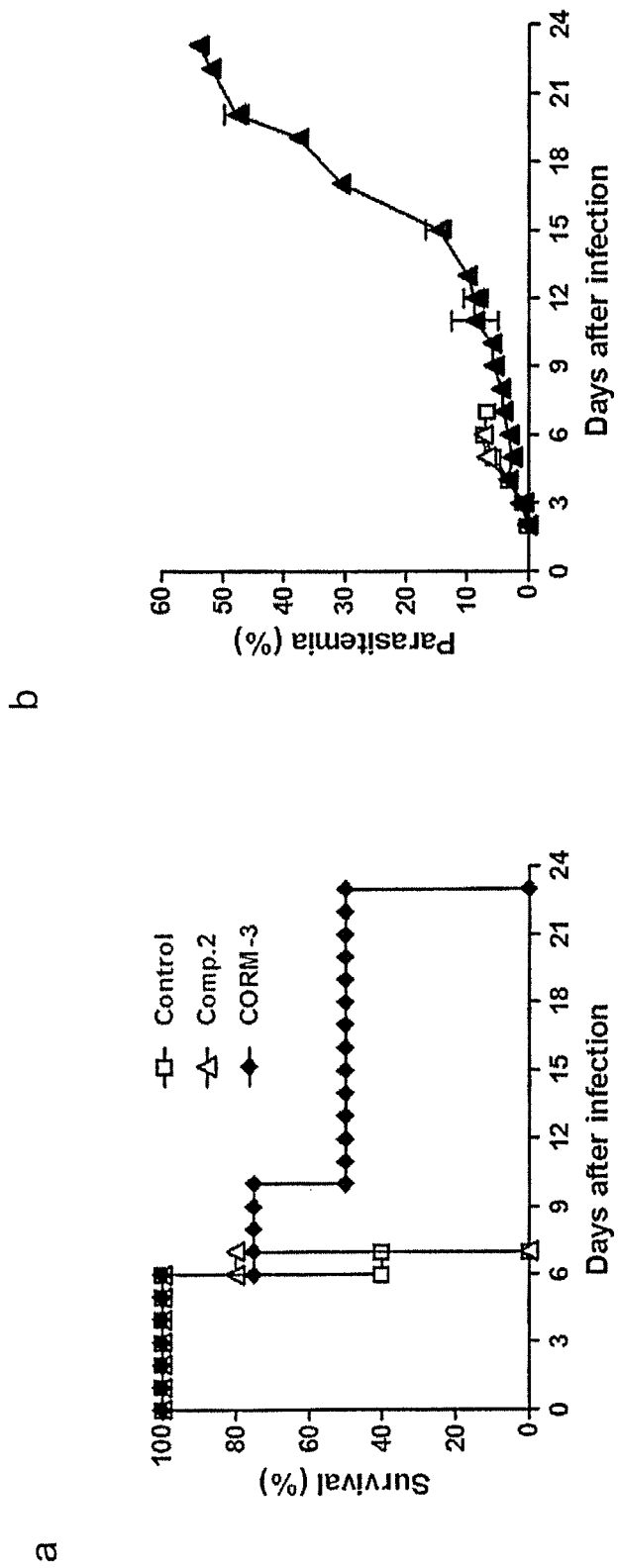
FIG. 12. CORM-3 partially protects from ECM.

The inventors also tested the therapeutic effect of CORM-3, $[Ru(CO)_3Cl_2(H_2NCH_2CO_2)]$, a water-soluble compound using the ECM model. It was observed that the administration of CORM-3 at equimolar concentration to CORM-2, within the same schedule of treatment as CORM-2, protected mice from ECM in 50% (FIG. 12a). Like with CORM-2 treatment, there was a statistically significant delay in parasitemia in CORM-3 treated mice between day 6 and day 8 of infection, compared with the controls (i.e., infected Compound 2-treated ($P<0.001$) and infected control mice ($P<0.05$)) (FIG. 12b). The protected CORM-3-treated mice died 3 weeks after infection due to the development of hyperparasitemia and anemia (>50% infected red blood cells) (FIG. 12b). Although CORM-3 could afford 50% protection against ECM, it was not as efficient as CORM-2.

Example 2

A Novel CO-Releasing Molecule (Compound 1)Protects Mice from ECM without COHb Formation A novel water soluble CO-RM, tricarbonyldichloro(methylthiogalactopyranoside) Ru(II) $[Ru(CO)_3Cl_2(Gal-S-Me)]$ (Compound 1), was synthesized through the reaction of CORM-2 with methylthiogalactopyranoside (Gal-S-Me) (FIG. 2a). This Ru tricarbonyl complex features a galactose (Gal) derived ligand coordinated to the Ru centre via a thioether linkage. The presence of the galactose ligand may confer a certain degree of liver specificity.

Tricarbonyldichloro(methylthiogalactopyranoside) Ru(II) $[Ru(CO)_3Cl_2(Gal-S-Me)]$, also referred to herein as Compound 1, was prepared by reacting CORM-2 with methylthiogalactopyranoside (Gal-S-Me) as described herein (see FIG. 2a and Materials and Methods section). The biodistribution of Compound 1 in tissues was assessed by quantifying the levels of Ru and CO in the host by the method of Vreman et al., *Anal Biochem* (2005) 341:280-9. Liver, kidney, spleen, lung and brain tissues of non-infected mice (NI) were analyzed one hour after administration of Compound 1 and the control molecule, Compound 2 (FIG. 2b). In Compound 1-treated mice, Ru could be detected in all organs analyzed with a marked affinity for the liver (FIG. 2b). In fact, the concentration of Ru in the liver of Compound 1-treated mice was approximately 7.0±0.3 times higher than that measured in the Compound 2-treated mice ($P<0.05$) (FIG. 2b). The brain was the organ where the levels of Ru were lower (401.8±17.3 times less than in the liver) indicating a low potential for neurotoxicity (FIG. 2b). The amount of Ru retained in the liver after the last injection of Compound I represented about 13.7±0.6% of the Ru administered in all doses. The levels of Ru in Compound 1-treated mice were higher than those in Compound 2-treated mice for all the organs analyzed ($P<0.05$) (FIG. 2b), implying a lower excretion rate of Compound 1 or its Ru-containing metabolites. The measured levels of CO for Compound 2-treated and Compound 1-treated mice were significantly different in all organs ($P<0.05$) (FIG. 2c). Compound 1 showed higher levels of CO in the liver and spleen, with the spleen showing the highest level. The spleen is an organ that plays a crucial role in erythrophagocytosis, process important for red blood cell turnover, and recycling of iron. Erythrocytes are hydrolyzed by splenic macrophages, where the degradation of hemoglobin occurs, haem is release, and is catabolized by heme oxygenase-1 into biliverdin, carbon monoxide and ferrous iron ($Fe^{2+}$). The endogenous production of CO due to increased HO-1 activity could explain the higher levels of CO seen in the spleen of Compound 1-treated mice. It is hypothesized that Compound 1 promotes/increases erythrophagocytosis.

The hen egg white lysozyme (HEWL) assay was used to assess the reactivity of Compound 1 in the presence of proteins (see, e.g., Santos-Silva, T. et al. *J Am Chem Soc* (2011) 133, 1192-1195). This paper describes the interactions of CORM-3 with plasma proteins. CORM-3 reacts rapidly with proteins, losing chloride ion, glycinate, and one CO ligand. It was envisioned that Compound 1 could react with serum proteins in a similar manner as seen previously for CORM-3 and form CO-adducts from which CO may then be released and exert its protective effects. Indeed, Compound 1 in the presence of HEWL forms protein-$Ru^{II}(CO)_2$ adducts but reacts slower than CORM-3 (see Materials and Methods, described herein, and FIG. 11a-11e), and thus may mean the CO release is slower and more efficient. It was observed that CORM-3 reacts faster and has a much weaker efficacy than Compound 1 in this ECM treatment.

The CO donation capacity of Compound 1 by a deoxymyoglobin (Mb) carbonylation assay was then evaluated (see, e.g., Clark et al., *Am J Pathol* (1992) 140:325-336). It was observed that Compound 1 transfers approximately 1 equivalent of CO to Mb after 15 minutes of incubation with deoxy-Mb, as seen for Ru tricarbonyl CORM-3 (see Materials and Methods, described herein). Altogether, these data demonstrate that Compound 1 is capable of transferring CO to the heme of Mb, reacts with proteins to form protein-$Ru^{II}(CO)_2$ adducts, and preferably distributes to the liver.

The potential protective effect of Compound 1 was next evaluated in ECM. *P. berghei* ANKA-infected C57BL/6 mice were treated twice daily with Compound 1 between days 2 and 3 after infection. Compound 1 treatment protected 100% of *P. berghei* ANKA-infected C57BL/6 mice from developing ECM in contrast to infected control and Compound 2-treated mice that died with ECM symptoms between days 6 and 8 after infection (P<0.0001) (FIG. 2d). A small but significant arrest in parasitemia in Compound 1-treated mice between days 5 and 7 after infection (P<0.01) (FIG. 2e) was also observed.

Figures 6A, 6B:
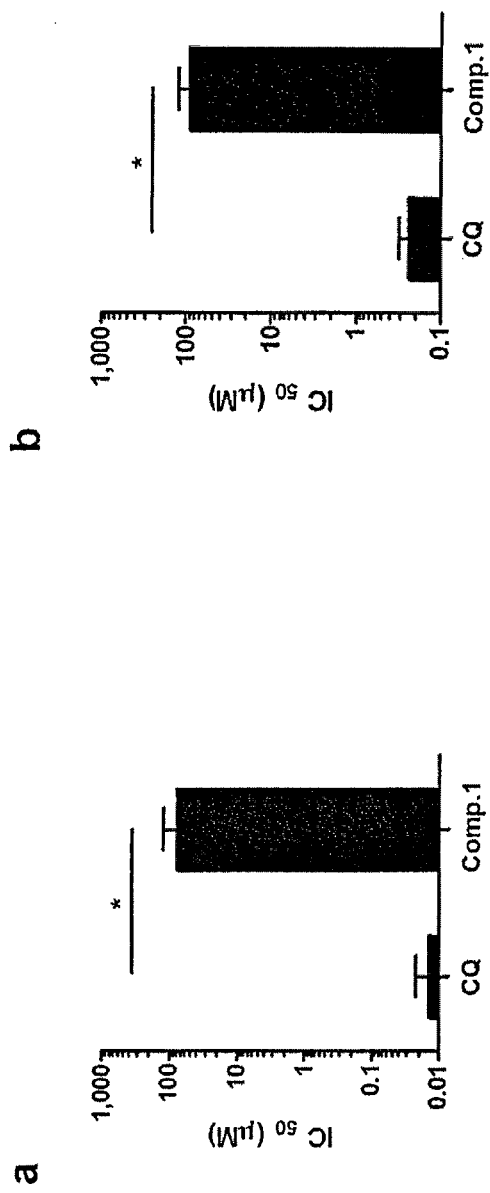
FIGS. 6*a*-6*b*. Compound 1 does not inhibit in vitro growth of and *P. falciparum* and *P. berghei* ANKA parasites. $IC_{50}$ of Compound 1 in *P. falciparum* clone 3D7 (FIG. 6*a*) and *P. berghei* ANKA parasites (FIG. 6*b*) in vitro cultures compared to the anti-malarial chloroquine (CQ). Plots representative of 3-4 experiments for each set of data.

The data led the inventors to wonder whether Compound 1 could have a direct anti-parasitic effect on *P. berghei* ANKA and *P. falciparum* parasites. To this end, the effect of Compound 1 and the anti-malarial chloroquine (CQ) was monitored on the in vitro replication of *P. falciparum* 3D7 isolate and *P. berghei* ANKA for 48 h and 24 h, respectively. Compound 1 showed $IC_{50}$ values remarkably high when compared to CQ, approximately 5600 and 350-fold higher in *P. falciparum* 3D7 and *P. berghei* ANKA parasites, respectively (see FIG. 6a-6b). The $IC_{50}$ for Compound 2 was not determined due to absence of inhibitory effect in the range of concentrations tested.

Figures 2F, 2G, 2H:
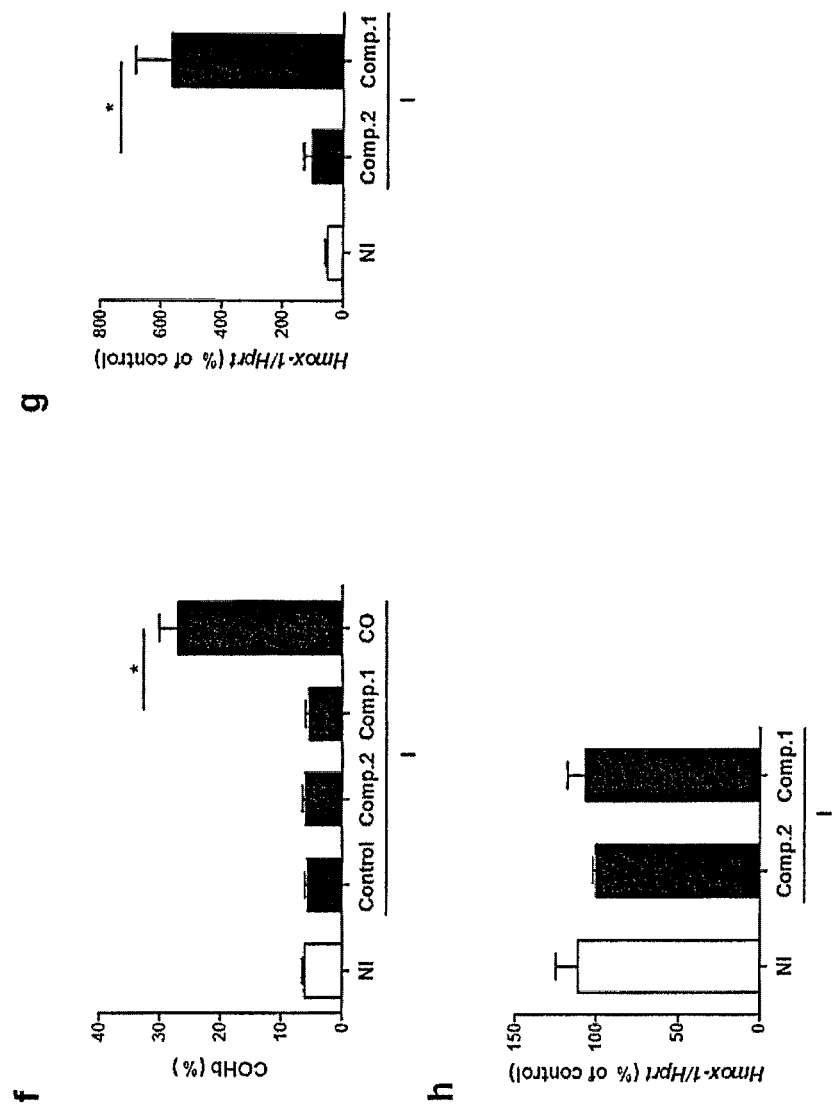

Altogether, the above results show that the therapeutic administration of Compound 1, while not having an anti-parasitic effect, has a significant impact on the overall outcome of the infection, as indicated by 100% survival of the infected Compound 1 treated mice (FIG. 2d). CO inhalation at a dose necessary to obtain similar protective effects for ECM (250 ppm for 24 h, starting at day 2 after infection) induced 30.3±2% COHb formation (P<0.05), which is an unacceptable value for humans. Remarkably, Compound 1 fully protected mice against ECM without causing measurable increase in COHb levels in the blood. The COHb levels in Compound 1-treated mice were similar to those observed for non-infected (NI), infected control, Compound 2-treated, and DMSO-treated mice (FIG. 2f). The levels of CO-Hb when using CO-RM-3 are similar to those of Compound 1. Taken together, these data demonstrate that Compound 1 fully protects mice from ECM onset without affecting oxygen transport by hemoglobin, thereby overcoming the main adverse effect of CO gas therapy.

Example 3

Compound 1 Induces the Expression of HO-1

It has been shown that HO-1 induction reduced CM incidence in *P. berghei* ANKA infected C57BL/6 mice (see, e.g., Pamplona et al., *Nat Med* (2007) 13:703-710). Compound 1 distributes preferentially to the liver, which is considered a mediator of systemic and local innate immunity and has been implicated in the regulation of genes that contribute to the control of inflammation, such as HO-1 (see, e.g., Nemeth et al., *Semin Immunopathol* (2009) 31:333-343). No signs of ruthenium are found in the brain. The inventors questioned whether Compound 1 could modulate the expression of HO-1 and thus contribute to the observed protection against ECM. Expression of HO-1 mRNA was significantly up-regulated in the liver of *P. berghei* ANKA infected Compound 1-treated C57BL/6 mice, 11.1±2.3 and 5.7±1.2 fold, when compared, respectively, to non-infected and infected Compound 2-treated mice (P<0.05) (FIG. 2g). Moreover, the expression of HO-1 mRNA in the brain of infected Compound 1-treated mice at day 3 after infection was not significantly different from non-infected and infected Compound 2-treated mice (FIG. 2h). These results show that treatment with Compound 1 induced the up-regulation of HO-1 expression in the liver of infected mice, thus contributing to the control of the systemic inflammatory response of the host to *P. berghei* ANKA infection.

Example 4

Compound 1 Prevents BBB Disruption and Neuroinflammation

Figures 3A, 3B, 3C, 3D, 3E:
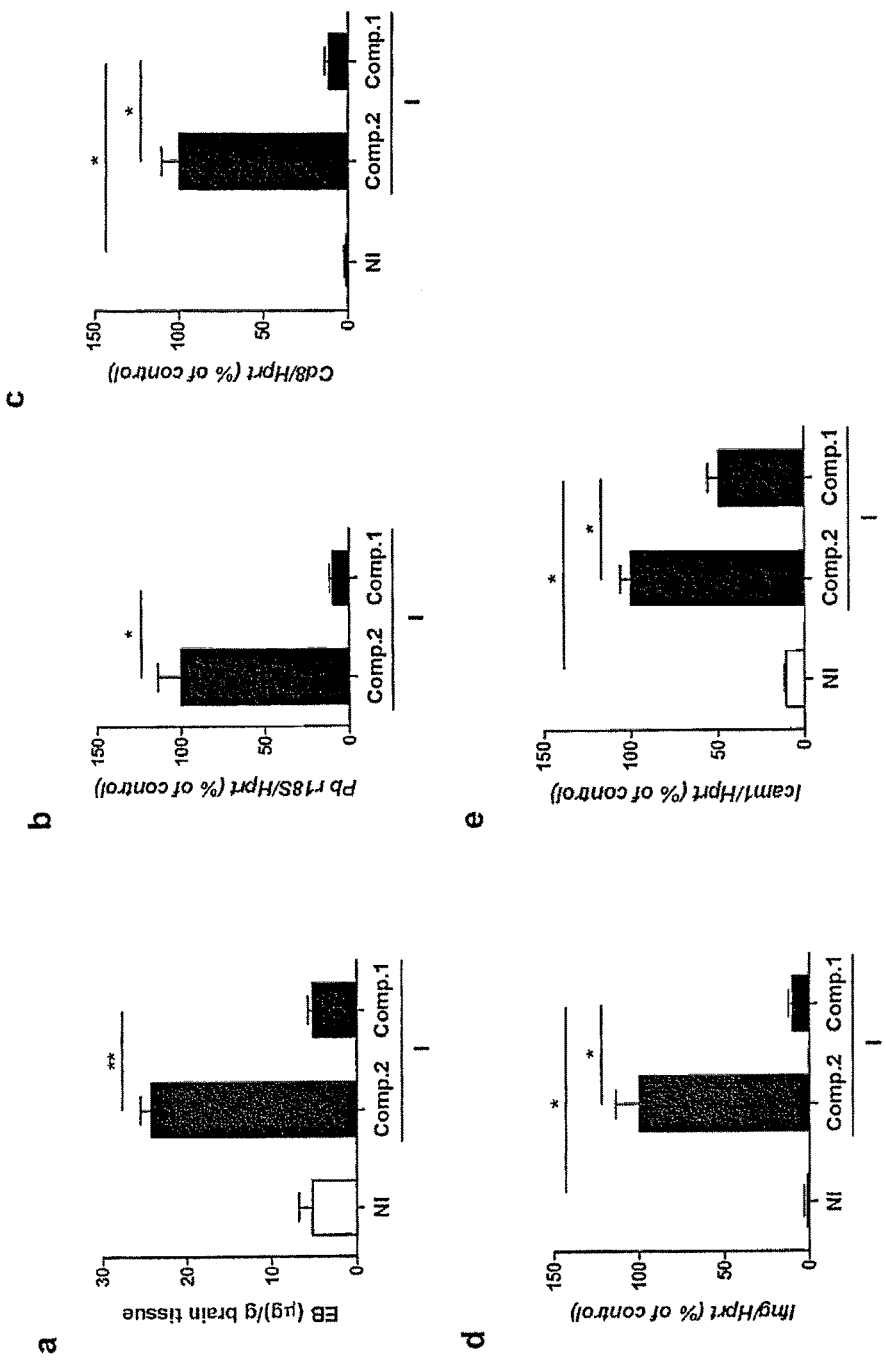
FIGS. 3a-3i. Compound 1 reduces parasite accumulation in the brain and neuroinflammation. BBB permeability (FIG. 3a), Parasite r18S (FIG. 3b), CD8β (FIG. 3c), IFN-γ (FIG. 3d) and ICAM-1 (FIG. 3e) mRNA expression were quantified by qRT-PCR. NI (n=4), I+Compound 2 (n=4) and I+Compound 1 (n=5). Evans Blue quantification is shown as mean μg of Evans Blue (EB) per g of brain tissue±standard error of the mean. NI (n=4); Compound 2 (n=5) and Compound 1 (n=5). Non-infected (NI), infected Compound 2-treated and Compound 1-treated mice were sacrificed when the control group, Compound 2-treated mice, showed signs of ECM and brains were harvested after intracardiac perfusion.
Figures 3F, 3G, 3H, 3I:
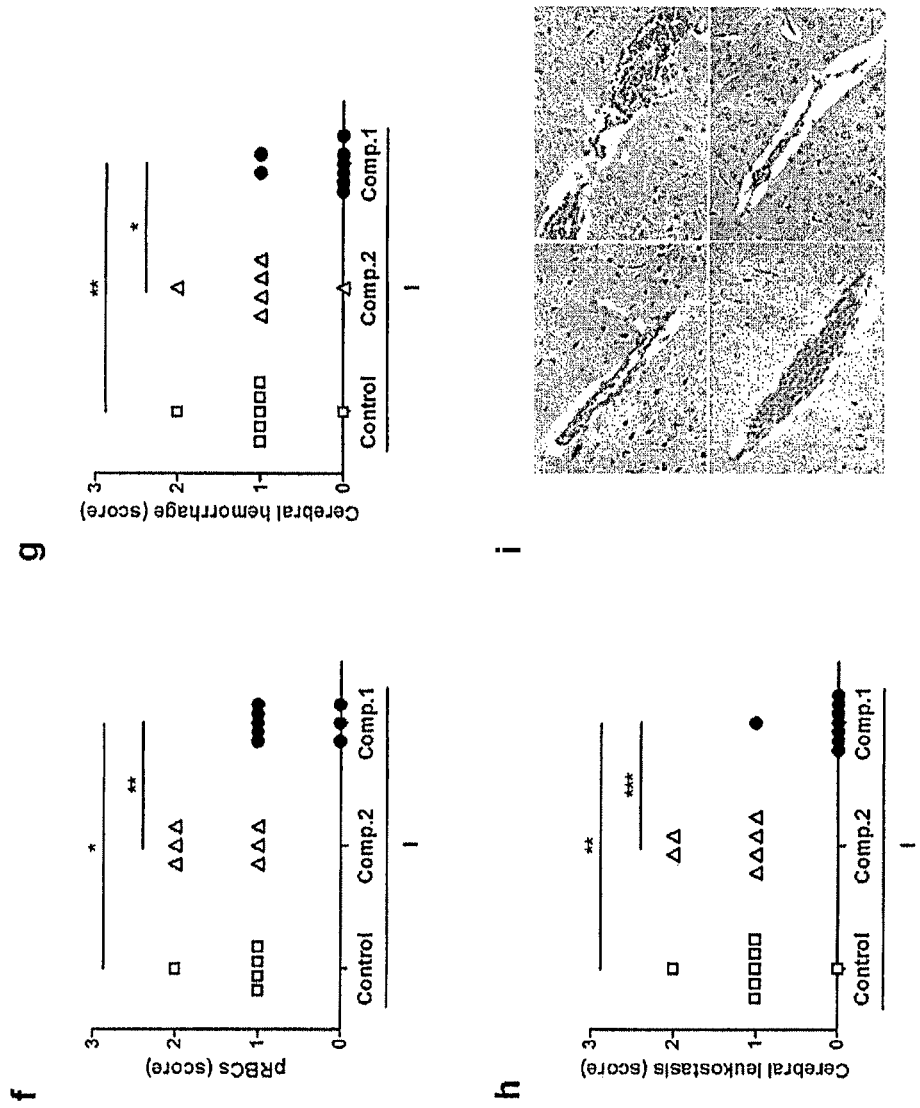
Figures 7A, 7B:
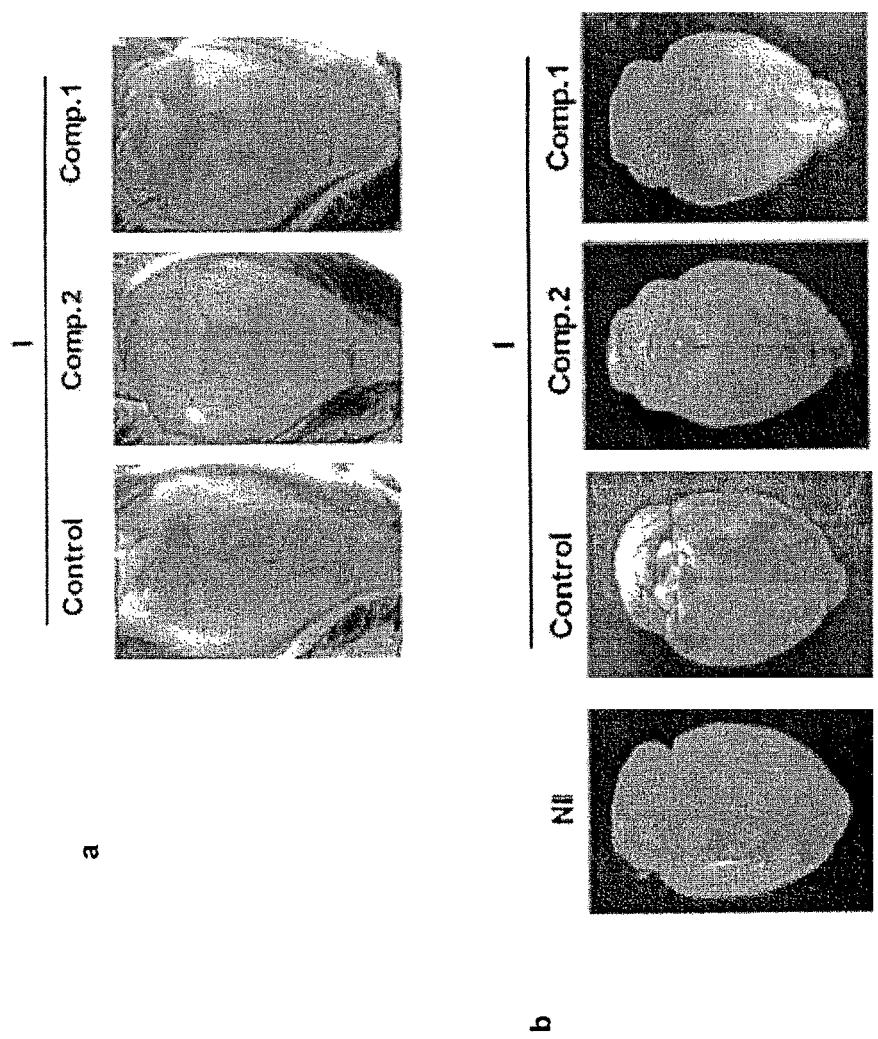
FIGS. 7*a*-7*b*. Compound 1 reduced Blood Brain Barrier (BBB) disruption and parenchymal brain hemorrhage in *P. berghei* ANKA infected mice. Cranium (FIG. 7*a*) and brains (FIG. 7*b*) after BBB disruption assessment by Evans Blue staining of non-infected (NI) versus *P. berghei* ANKA infected (control) and infected Compound 2-treated (I+Compound 2) or Compound 1-treated C57BL/6 mice (I+Compound 1). Images are representative of a total of 5 mice per group.
Figure 8:
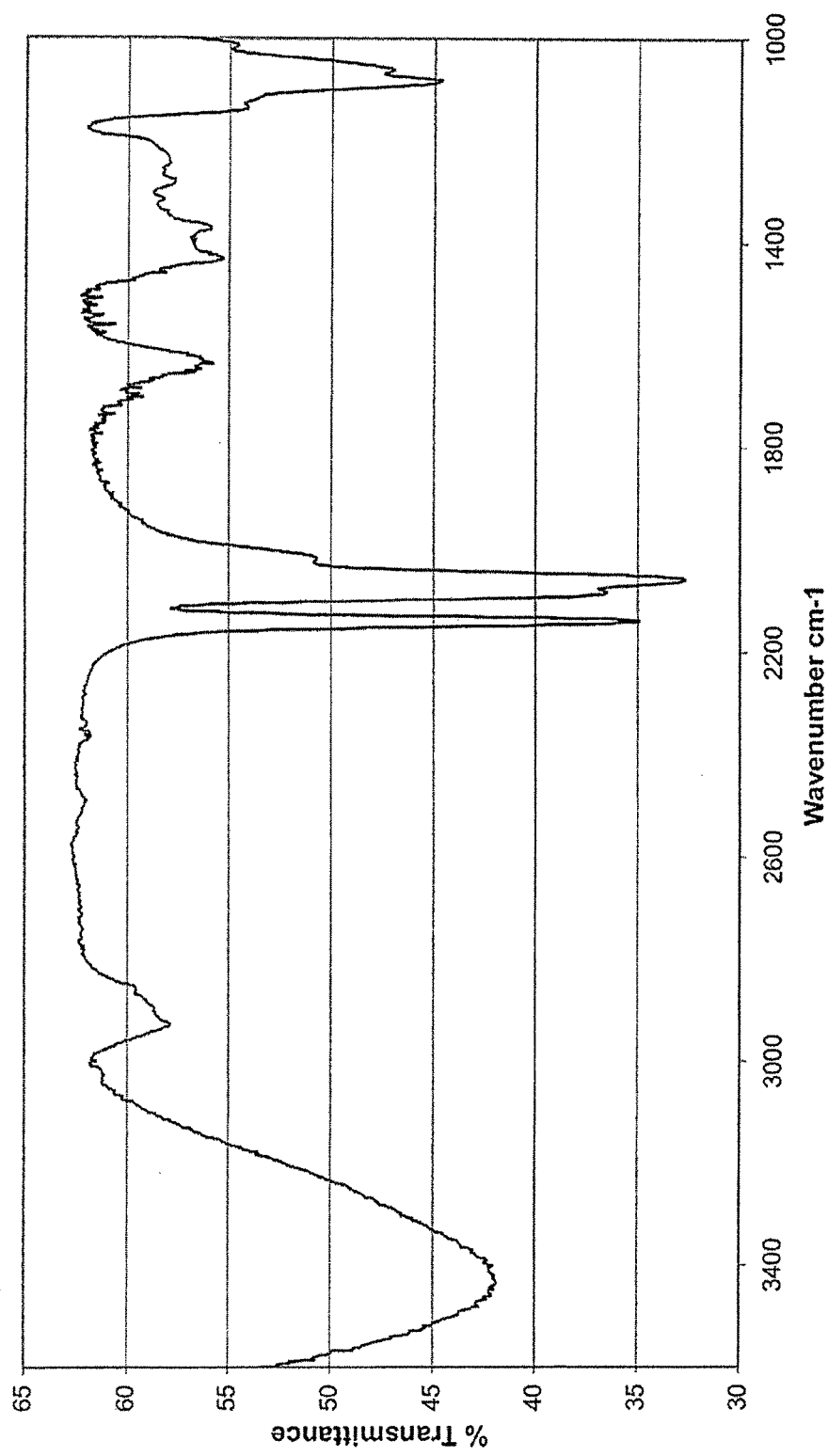
FIG. 8. IR spectrum (KBr) of $RuCl_2(CO)_3$(methyl β-D-thiogalactopyranoside) (Compound 1).
Figure 9:
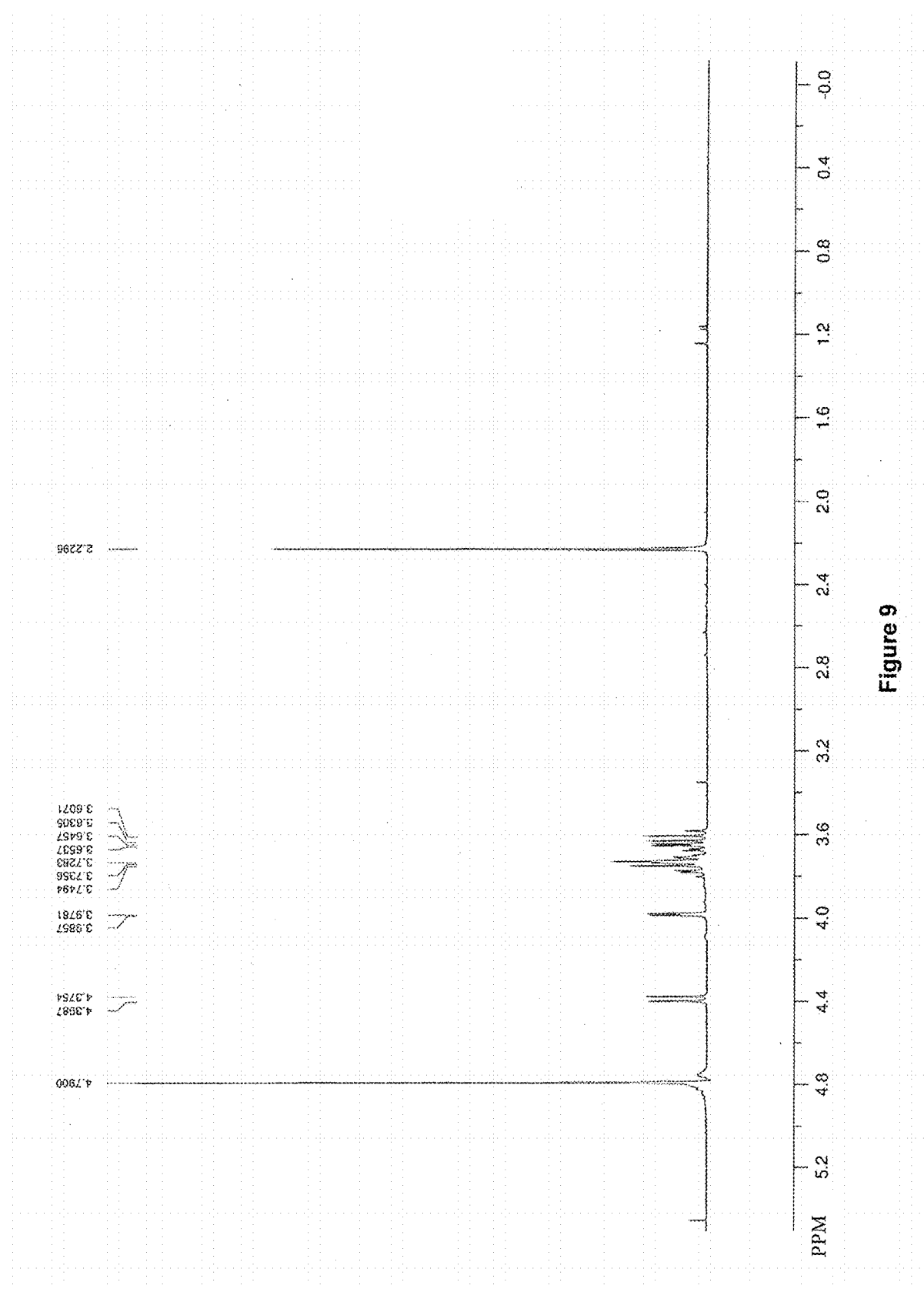
FIG. 9. $^1$H-NMR spectrum of $RuCl_2(CO)_3$(methyl β-D-thiogalactopyranoside) (Compound 1) in $D_2O$.

Blood-brain barrier (BBB) disruption is a hallmark of ECM and has been reported in human CM (see, e.g., Thumwood et al., *Parasitology* (1988) 96:579-589; Medana et al., *Int J Parasitol* (2006) 36:555-568). *P. berghei* ANKA-infected non-treated and Compound 2-treated C57BL/6 mice showed BBB disruption as measured by Evans blue accumulation in brain parenchyma, i.e. 4.3±0.65 and 6.7±1,5 fold increase, respectively, as compared to NI mice (P<0.01), whereas Compound 1-treated mice did not show any evidence of BBB disruption as the levels of Evans blue accumulation were similar to NI mice (FIG. 3a and FIG. 7a-7b). Inhibition of BBB disruption is known to contribute to the suppression of ECM development (see, e.g., Favre et al., *Microbes Infect* (1999) 1:961-8). Furthermore, several reports have unequivocally demonstrated that the development of ECM in *P. berghei* ANKA-infected mice is dependent on the presence of T cells, mainly $CD8^+$ T cells (see, e.g., Berendt et al., *Parasitol Today* (1994) 10:412-414; Belnoue et al., *J Immunol* (2002) 169:6369-6375; Yanez et al., *J Immunol* (1996) 157:1620-1624). More recently, it has been demonstrated that accumulation of $CD8^+$ T cells in the brain is not sufficient for the development of ECM in C57BL/6 mice, but the concomitant presence of parasitized red blood cells (pRBC) is necessary for the pathology onset (see, e.g., Baptista et al., *Infect Immun* (2010) 78:4033-9). Both pRBC accumulation and CD8-β-chain mRNA expression in the brain were significantly lower in Compound 1-treated mice when compared with Compound 2-treated mice, which showed clear signs of CM (P<0.01) (FIG. 3b, c). During ECM, pro-inflammatory cytokines, like IFN-γ, and adhesion molecules, such as ICAM-1, are up-regulated and play a decisive role in the pathogenesis of ECM (Favre supra; de Kossodo et al., *J Immunol* (1993) 151:4811-4820; Rudin et al., *Eur J Immunol* (1997) 27:810-815). Importantly, treatment with Compound 1 reduced IFN-γ mRNA expression compared to infected Compound 2-treated mice (P<0.01) (FIG. 3d) and decreased ICAM-1 expression 2.02±0.06-fold, (P<0.01, Compound 1-treated versus Compound 2-treated mice), when assessed at day 6 after infection (FIG. 3e).

Compound 1 treatment also prevented the neuropathologic features associated with ECM (see, e.g., Pamplona et al., *Nat Med* (2007) 13:703-710; Neill et al., *Parasitology* (1992) 105:165-175). Brains from infected and Compound 2-treated *P. berghei* ANKA-infected mice showed evidence of microvascular congestion with pRBC and leukocytes and hemorrhagic foci. In contrast, Compound 1-treated infected mice showed less hemorrhages, and the vessels had lower accumulation of pRBC and leukocytes (FIG. 3f-i). Overall, these results show that Compound 1 treatment prevents BBB permeability, decreases congestion, hemorrhages, and neuroinflammation in the brain of infected mice.

Example 5

Compound I Protects Mice from Developing Malaria-Associated ALI

Figures 4A, 4B, 4C, 4D, 4E:
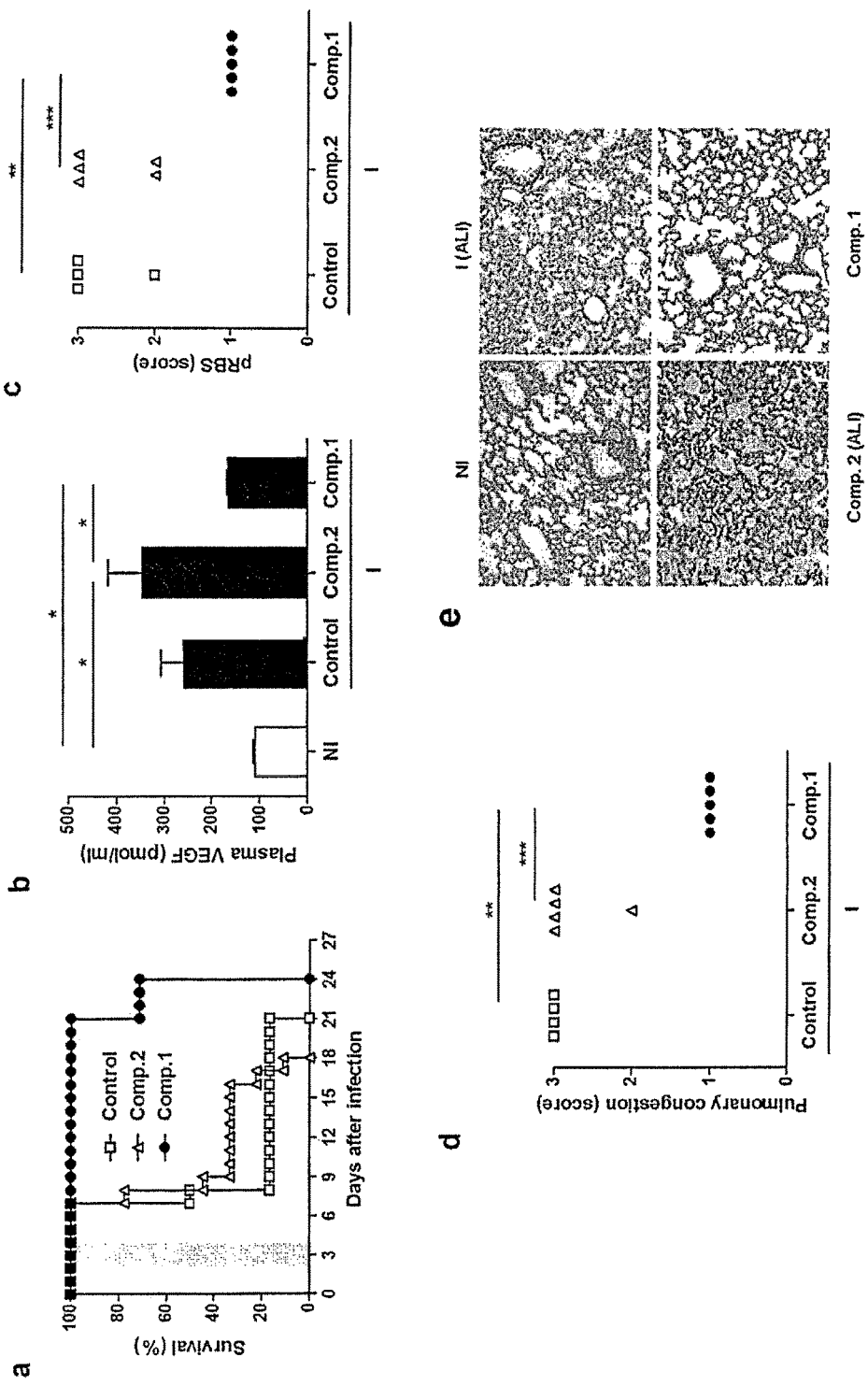
FIGS. 4a-4e. Compound 1 protects mice from malaria-associated ALI (M-AALI).

The pathogenesis of severe *P. falciparum* malaria is complex and results in a broad spectrum of disease manifestations, such as CM and ALI. The inventors next evaluated the protective effect of Compound 1 in a model of malaria-associated acute lung injury (M-AALI) (see, e.g., Epiphanio et al. *PLoS Pathog* (2010) 6:1-10). The M-AALI model, based on the infection of DBA-2 mice with *P. berghei* ANKA, is characterized by dyspnea, airway obstruction, hypoxemia, pulmonary exudate and elevated VEGF levels in plasma, followed by death between days 7 and 12 after infection. None of *P. berghei* ANKA-infected DBA/2 mice, treated twice daily with Compound 1 between days 2 and 4 after infection, developed M-AALI. In the control groups of infected mice non-treated and Compound 2-treated, 83% and 67% of the mice, respectively, died displaying M-AALI symptoms such as dyspnea, respiratory insufficiency (as first symptoms), and pulmonary exudate and high VEGF levels in the plasma analysed post-mortem (FIG. 4a). Moreover, VEGF levels were significantly lower in infected mice treated with Compound 1 (P<0.001; FIG. 4b). Histological examination of lung tissue from infected mice, infected Compound 2 and Compound 1-treated mice showed major differences in the vascular congestion with pRBCs (FIG. 4c-e). In sum, the data shows that treatment with Compound 1 significantly improves the infection outcome in the M-AALI model.

Example 6

Compound 1—a Potential Adjunctive/Adjuvant Therapy for ECM

The above data shows that treatment with Compound 1 protects *P. berghei*-infected mice from death caused by ECM and M-AALI when administered before symptoms of disease are observed. However, to be useful in humans, Compound 1 should show therapeutic activity after the onset of disease, either alone or in combination with anti-malarial drugs. Thus, the inventors decided to test Compound 1 as an adjunctive and adjuvant therapy during the acute phase of ECM. Artesunate (AS) is the primary treatment in severe malaria and is generally effective in controlling *P. falciparum* parasitemia and has been used previously to treat *P. berghei* ANKA infected mice (see, e.g., Vivas et al., *Acta Trop* (2008) 105:222-228; Bienvenu et al., *Acta Trop* (2008) 106:104-8; Sinclair et al., *Cochrane Database Syst Rev* 3, CD005967). Therefore, the inventors assessed the combination of Compound 1 and AS on parasite clearance and clinical recovery from ECM. Two AS and Compound 1 combinations were tested: (i) Adjunctive therapy: AS and Compound 1 were administered concomitantly for 2 days after the onset of CM followed by a 3-day treatment with Compound 1 alone, or (ii) Adjuvant therapy: AS was administered on the first 2 days after CM onset followed by Compound 1 administration for 3 more days.

Figures 5A, 5B:
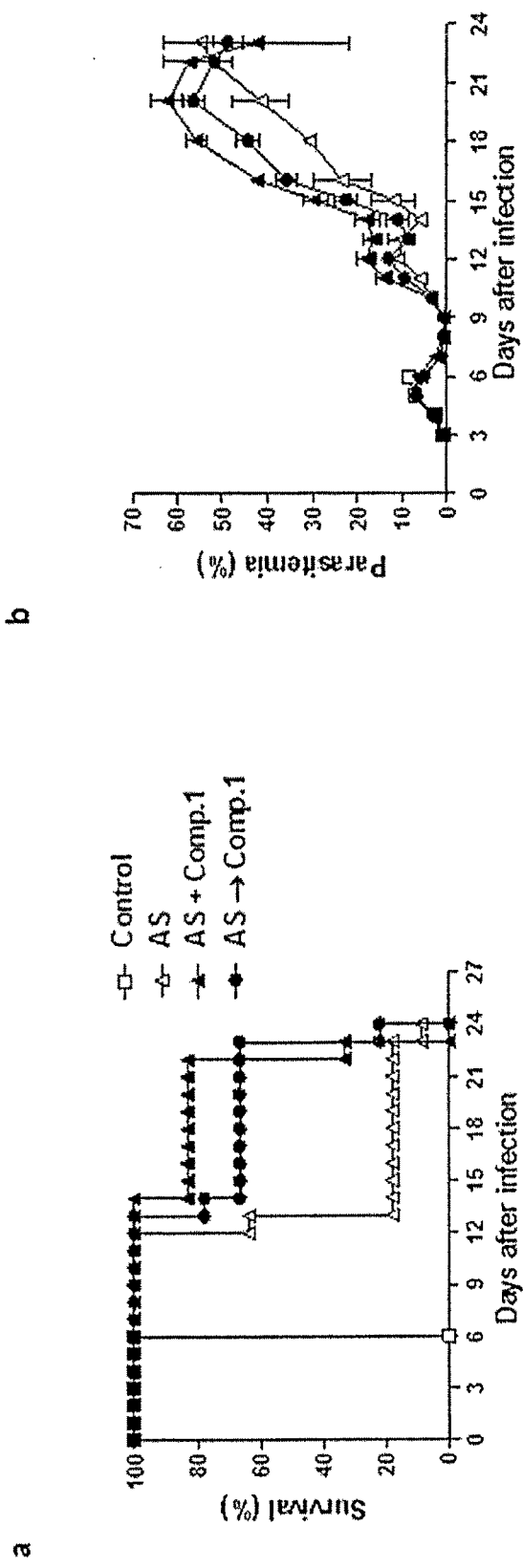
FIGS. 5a-5c. Compound 1 is a potential adjunctive/adjuvant therapy for ECM.
Figure 5C:
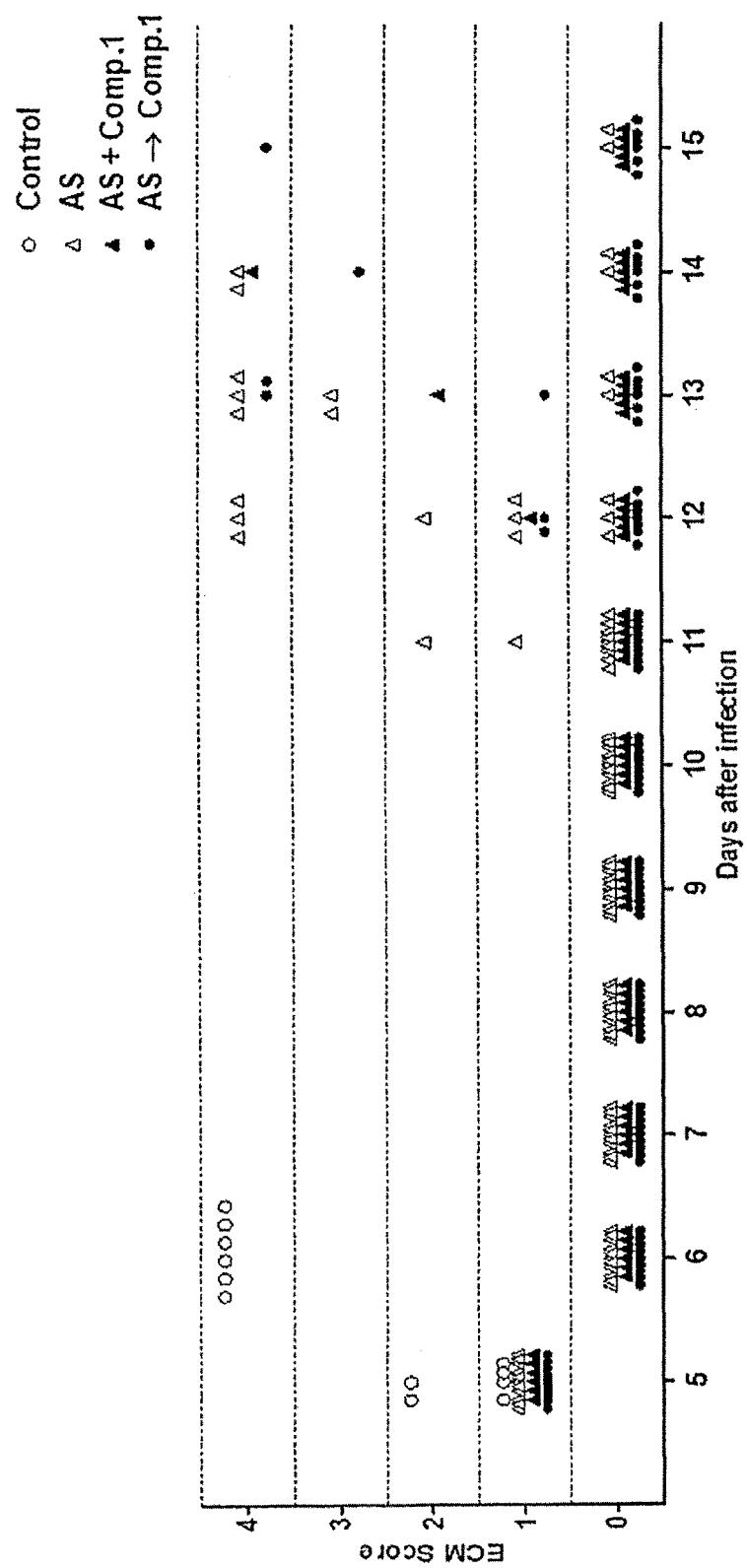

The treatment with AS started when the infected mice (control) showed the initial stage of ECM (score of 1). All infected non-treated mice died of ECM by day 6 after infection (FIG. 5a). The effect of anti-malarial treatment with AS alone was shown by the decrease of parasitemia from 6.8±0.3% to 0.59±0.06% % (at days 5 and 9 post-infection, respectively). AS treatment alone delayed, but in most cases did not prevent death by CM (FIG. 5b). Nine out of 11 (82%) AS-treated mice died with ECM between days 12 and 13 after infection (FIG. 5a). Mice treated simultaneously with AS and Compound 1 under the adjunctive protocol showed a significant increase in survival (83%) when compared with AS-treated group (18%) (P<0.01) (FIG. 5a). The infected group treated with the AS and Compound 1 combination under the adjuvant protocol showed an improved survival of 67% from ECM (P<0.01 versus AS-treated mice) (FIG. 5a). Since no anti-malarial agents were administered after day 7, mice that did not have ECM developed hyperparasitemia and anemia (>30% parasitemia) and were sacrificed within 3 weeks after infection (FIG. 5a). During the administration of AS, between days 5 and 6, Compound 1 did not interfere with the anti-malarial action of AS in vivo (FIG. 5b). These results clearly show that an anti-malarial drug and Compound 1 used in combination after the onset of ECM can significantly improve survival.

Discussion

The inventors have discovered a novel, water-soluble, CORM, tricarbonyldichloro (thiogalactopyranoside) Ru(II) (Compound 1), capable of transferring CO to heme proteins and that protects mice from death caused by severe malaria. The inventors have observed that the lipid-soluble CORM-2 could fully protect mice from death caused by ECM, while the water-soluble CORM-3 analogue was less active and could only protect 50% of the mice from ECM (see FIG. 12)). CO inhalation suppresses the pathogenesis of CM and M-AALI in mice (see, e.g., Pamplona supra; Epiphanio supra) but produced unacceptable levels of carboxyhaemoglobin (COHb). COHb is routinely used to assess CO toxicity in humans (see, e.g., Motterlini et al., *Nat Rev Drug Discov* (2910) 9:728-743). The data shows that Compound 1, at therapeutic concentrations, did not induce the formation of measurable levels of COHb while preserving the protective effects seen with inhaled CO.

This work also provides evidence that Compound 1 treatment in ECM model induces the expression of HO-1. It has previously been shown that the induction of HO-1 protects mice from developing ECM (see, e.g., Pamplona supra). Additionally, in a model of chronic intestinal inflammation it has been shown that CO could ameliorate chronic murine colitis through a HO-1-dependent pathway (see, e.g., Hegazi et al., *J Exp Med* (2005) 202:1703-1713). The data strongly suggest that HO-1 mediates a significant component of the anti-inflammatory action of Compound 1 in ECM, which is characterized not only by an exacerbated parasite-mediated inflammatory responses but also to pRBC, unparasitized RBCs sequestration in the microvasculature of the brain, and more recently by coagulopathy and microcirculation dysfunction (see, e.g., van der Heyde et al., *Trends Parasitol* (2006) 22:503-508).

Despite the introduction of new anti-malarial agents, such as artemisinin derivatives (e.g. artesunate), these drugs take at least 12-18 h to kill parasites (see, e.g., Mishra et al., *Nat Rev Neurol* (2009) 5:189-198). Deaths from severe malaria may occur within the first 24 h after hospital admission (see, e.g., Idro et al., *Lancet Neurol* (2005) 4:827-840). Thus, administration of adjunctive therapies in the first 24 h is critical to reduce mortality. Children who survive the acute episode of CM often have long-term cognitive (~25%) and neurologic (1.1-4.4%) deficits (see, e.g., Trampuz et al., *Crit Care* (2003) 7:315-323; Idro supra). The use of adjunctive therapies that would reduce neurological injury may prove essential to reduce this burden. A series of adjunctive therapies such as anti-TNF-α agents, iron chelators (such as desferrioxamine) and dichloroacetate (stimulates pyruvate dehydrogenase and so reduces lactate) have been assessed in randomized clinical trials (reviewed in John et al., *Expert Rev Anti Infect Ther* (2010) 8:997-1008).

Remarkably, the present data demonstrates that Compound 1 is an effective adjuvant when in combination with an artemisinin anti-malarial agent (e.g., artesunate (AS)) for the treatment of malaria infection, e.g., ECM. Furthermore, treatment with Compound 1 protected mice from M-AALI, and significantly decreased the levels of VEGF in circulation. Therefore, Compound 1 may be an effective adjuvant agent in the treatment of M-AALI as well as inflammatory conditions such as ALI since the only treatments shown to improve survival and reduce mortality for patients with ALI have been supportive care strategies (see, e.g., Jain et al., Mayo Clin Proc (2006) 81:205-212).

In summary, the novel CO-RM, Compound 1, displays improved water solubility, is able to transfer CO to heme proteins and distributes in vivo with a moderate affinity for the liver. The bioactivity and key therapeutic features of Compound 1 are shown in two distinct models of severe malaria. Importantly, the data shows the use of this compound as a promising adjuvant therapy during the acute phase of cerebral malaria. Compound 1 fully protects mice against experimental CM (ECM) and acute lung injury (ALI). Compound 1 enables specific CO delivery in vivo without affecting oxygen transport by hemoglobin, the major limitation in CO inhalation therapy. The protective effect is CO-dependent and induces the expression of heme oxygenase-1, which contributes for the observed protection. Importantly, when in combination with the anti-malarial drug artesunate, Compound 1 is an effective adjuvant for ECM conferring protection after the onset of severe disease.

The present study further clarifies the anti-inflammatory and cytoprotective effects of a novel Ru tricarbonyl CO-RM in ECM and M-AALI models. The data highlights the therapeutic potential of Compound 1 in targeting pharmacologically the expression of HO-1 that plays a crucial cytoprotective, immunomodulatory and anti-inflammatory roles. The work clearly demonstrates that CO delivered from Compound 1 can induce similar protection as was seen with CO gas therapy, but without the toxic effects (elevated COHb levels) of CO inhalation. Altogether, this work represents an important pre-clinical proof-of-principle for CORMs as a new class of drugs to treat severe forms of malaria infection and establish a novel CO-RM with many important drug-like features relevant to other therapeutic applications.

Materials and Methods

Reagents

For the in vivo studies, tricarbonyldichlororuthenium(II) dimer (CORM-2) and Artesunate (AS) were obtained from Sigma-Aldrich. CORM-3, fac-Ru(CO)$_3$Cl(NH$_2$CH$_2$COO) also referred to as fac-Ru(CO)$_3$Cl(glycinate), was synthesized as described previously (see, e.g., Clark et al., Am J Pathol (1992) 140:325-36), Compound 2 (Tetrakis(dimethylsulfoxide)dichlororuthenium(II)) was purchased from Strem Chemicals, Inc. β-D-thiogalactopyranoside was purchased from Carbosynth. Hen Egg White Lysozyme C (PDB code 3b61; UniProtKB/Swiss-Prot code P00698) (Calculated average isotopic mass=14305.1) was used as a model for the interaction with Ru(CO)$_3$Cl$_2$(Gal-S-Me) and CORM-3.

Mice

C57BL/6 and DBA-2 wild-type mice were purchase from Charles River Laboratories Internation Inc. (Barcelona, Spain) and housed in the pathogen-free facilities of the Instituto de Medicina Molecular. All protocols were approved by and conducted according to the Animal Care regulations of the Direcqao Geral de Veterinairia (Portugal).

Parasites, Infection and Disease Assessment

Red blood cells infected with green fluorescent protein (GFP)-transgenic P. berghei ANKA and P. berghei ANKA was used to infect mice (see, e.g., Franke-Fayard et al. Mol Biochem Parasitol (2004) 137:23-33). Cryopreserved parasites were passed once through C57BL/6 or DBA-2 mice before being used to infect experimental animals. C57BL/6 or DBA-2, 6- to 8-wk-old mice (sex matched in each experiment) were infected by intra-peritoneal (i.p.) injection of $10^6$ infected RBCs. The infected mice were monitored daily for clinical symptoms of experimental cerebral malaria (ECM) including hemi- or paraplegia, head deviation, tendency to roll over on stimulation, ataxia and convulsions, or ALI, including dyspnea. Mice showing severe signs of ECM at day 5, 6 or 7 post-infection (p.i.) and ALI between days 7 and 9 were sacrificed. Parasitemia was assessed by flow cytometry for mice infected with GFP-expressing P. berghei ANKA, using tail blood, as previously described (see, e.g., Pamplona et al., Nat Med (2007) 13:703-710). Mean parasitemia is expressed as percentage of infected red blood cells. For mice infected with non-GFP P. berghei parasitemia was assessed daily by microscopic counting of Giemsa-stained thin blood smears. Mean parasitemia is expressed as percentage of infected red blood cells. Survival is expressed as percentage.

Experimental Cerebral Malaria Clinical Assessment

In order to evaluate the clinical presentation of experimental cerebral malaria, a classification was used in clinical stages from 0 to 4 (see, e.g., Bienvenu et al., Acta Trop (2008) 106:104-8; Franklin et al., Proc Natl Acad Sci USA (2011) 108:3689-94). Briefly, stage 0 indicates no detectable clinical symptoms, stage 1, ruffled fur; stage 2, ruffled fur and unbalancing; stage 3, limb paralysis and respiratory distress and stage 4, convulsions, coma or death. The mice were clinically classified before and after the treatment to evaluate the clinical recovery.

In Vivo Treatments

CORM-2 (Sigma-Aldrich) and Compound 2 were solubilized using 10% dimethyl sulfoxide (DMSO; Sigma-Aldrich) in PBS. CORM-3 and Compound 1 were solubilized in PBS (lx). CORM-2 solution (20 mg/kg of body weight) was administered intravenously (i.v.) according to the chosen schedules. Compound 2, CORM-3 and Compound 1 were administered i.v. at equimolar concentrations relative to CORM-2 (36.7 mg/Kg). As vehicle control, we used a solution of 10% DMSO in PBS administered i.v. The concentrations of CORM-2 used in the present study were based on previous reports (see, e.g., Chen et al. Am. J. Pathol. (2009) 175:422-429; Sun et al., World. J. Gastroenterol. (2008) 14:547-553). Artesunate is presented as a powder of artesunic acid. Artesunate (AS) solution was prepared by dissolving 60 mg of anhydrous artesunic acid in 1 ml of sodium bicarbonate (5%) to form sodium artesunate and then diluted in 5 ml of NaCl (0.9%). An AS solution (i.p.) was administered at 40 mg/Kg/day, as described previously (see, e.g., Bienvenu, Acta Trop (2008) 106:104-108). The AS treatment was started when the infected non-treated mice presented the clinical stage 1 for experimental cerebral malaria.

Quantification of COHb in Peripheral Blood

Blood was collected from the tail of the mice to capillary tubes (VWR) with heparin (100 i.u./ml in PBS 1x; LEO Pharma Inc.), transferred into AVOXimeter 4000 cuvettes (ITC) where the levels of carboxyhemoglobin (COHb), oxyhemoglobin (O$_2$Hb) and methemoglobin (MetHb) were measured in a portable AVOXimeter 4000 CO-oximeter (ITC). Results are shown as mean percentage of total hemoglobin species in circulation.

Determination of CO in Tissues

CO was quantified in different tissues as previously described (see, e.g., Vreman et al., Anal Biochem (2005) 341:280-289). Briefly, CO was liberated as gas in a closed vial by adding 25 μL of water and 5 μL of sulfosalicylic acid (SSA, 30% [wt/vol]) to 30 μL of diluted sample after being homogenized. The vials were incubated on ice for at least 10 min before being analyzed. The gas in the headspace of the vials was analyzed quantitatively with a gas chromatograph (GC) equipped with a reducing-compound photometry detector (RCP detector) (Peak Laboratories, Mountain View, Calif.), which allows to quantify CO in gas at concentrations as low as 1-2 parts per billion (ppb). The amount of CO was calculated using a calibration curve prepared from CO standards. Briefly, blood was collected from the tail of the mice to capillary tubes (VWR) with heparin (100 i.u./ml in PBS 1×; LEO Pharma Inc.), transferred into AVOXimeter 4000 cuvettes (ITC) where the levels of carboxyhemoglobin (COHb), oxyhemoglobin ($O_2$Hb) and methemoglobin (MetHb) were measured in a portable AVOXimeter 4000 CO-oximeter (ITC). Results are shown as mean percentage of total hemoglobin species in circulation.

Quantitative Real-Time Reverse Transcription PCR (qRT-PCR)

Mice were sacrificed, when infected control mice presented signs of ECM, and perfused intracardially with PBS to remove circulating RBC and leukocytes from the organs. RNA was isolated from brains, livers and lungs using Trizol Reagent (Invitrogen, Life technologies), according to the manufacturer's recommendation. The synthesis of the first-strand cDNA from the RNA templates was carried out using the Transcriptor First Strand cDNA Synthesis Kit (Roche). RT-PCR reactions were performed in the presence of SYBER Green (SYBER Green PCR master mix, Applied Biosystems) on an ABI PRISM 7500Fast (Applied Biosystem). Oligonucleotides used for the specific amplification of genes include:

```
SEQ ID NO 1:    hprt 5'-GTTGGATACAGGCCAGACTTTGTTG-3' (forward);

SEQ ID NO 2:    5'-GATTCAACCTTGCGCTCATCTTAGGC-3' (reverse);

SEQ ID NO 3:    ho-1 5'-TCTCAGGGGGTCAGGTC-3' (forward);

SEQ ID NO 4:    5'-GGAGCGGTGTCTGGGATG3' (reverse);

SEQ ID NO 5:    Pb 18S 5'-AAGCATTAAATAAAGCGAATACATCCTTAC-3'
                (forward);

SEQ ID NO 6:    5'-GGAGATTGGTTTTGACGTTTATGTG-3' (reverse);

SEQ ID NO 7:    CD8β 5'TGCTCGAGATGTGATGAAGG-3' (forward);
and

SEQ ID NO 8:    5'-TCCCCTGTTGACTGGTCATT-3' (reverse);

SEQ ID NO 9:    ifn-γ5'-CACACTGCATCTTGGCTTTG-3' (forward);

SEQ ID NO 10:   5'-TCTGGCTCTGCAGGATTTTC-3' (reverse);

SEQ ID NO 11:   icam-1 5'-CGAAGGTGGTTCTTCTGAGC-3' (forward);
and

SEQ ID NO 12:   5'-GTCTGCTGAGACCCCTCTTG-3' (reverse).
```

Quantification of Ru in Tissues

The tissue samples were weighed and dried at 80° C. overnight followed by 2 or more hours at 120° C. The dried tissues were then digested by the addition of 2 mL of tetraethylammonium hydroxide solution (20% wt in water) (Sigma-Aldrich (St. Louis, Mo., USA)) for 24 hours. After the complete tissue digestion, 1 mL of water was added. The Ru content was analyzed by an inductively coupled plasma-atomic emission spectrometer (ICP-AES) (model Ultima-Horiba Jobin Yvon, Longjumeau, France) using an external Ru standard method.

Histology

For evaluation of histological features, mice were deeply anesthetized until cessation of breathing when infected control mice presented signs of ECM or ALI. The livers, lungs, and brains were removed and fixed in 10% buffered formalin for 24-72 h. Four-micron sections were cut from paraffin-embedded tissues and stained with hematoxylin and eosin according to standard procedures. Histological analyses were performed on a Leica microscope DM 2500 (Leica Microsystems).

VEGF Protein Levels Determination

Mouse VEGF in plasma samples was determined using a commercial ELISA kit (R&D Systems) following the manufacturer's instructions. The group classification was only performed by the end of each experiment after determining the cause of death.

The relative changes in gene expression between experimental and control groups were calculated by the Pfaffl method using hprt as internal control gene.

Statistical Analysis

For samples in which n>5, statistical analyses were performed using the Student's t-test and for n<5, statistical analyses were performed using Mann-Whitney U-test.

Survival curves were compared using the Log-rank test and the Gehan-Breslow-Wilcoxon test. P<0.05 was considered significant.

Quantitation of CO Release Using a Mb Assay

Figure 10:
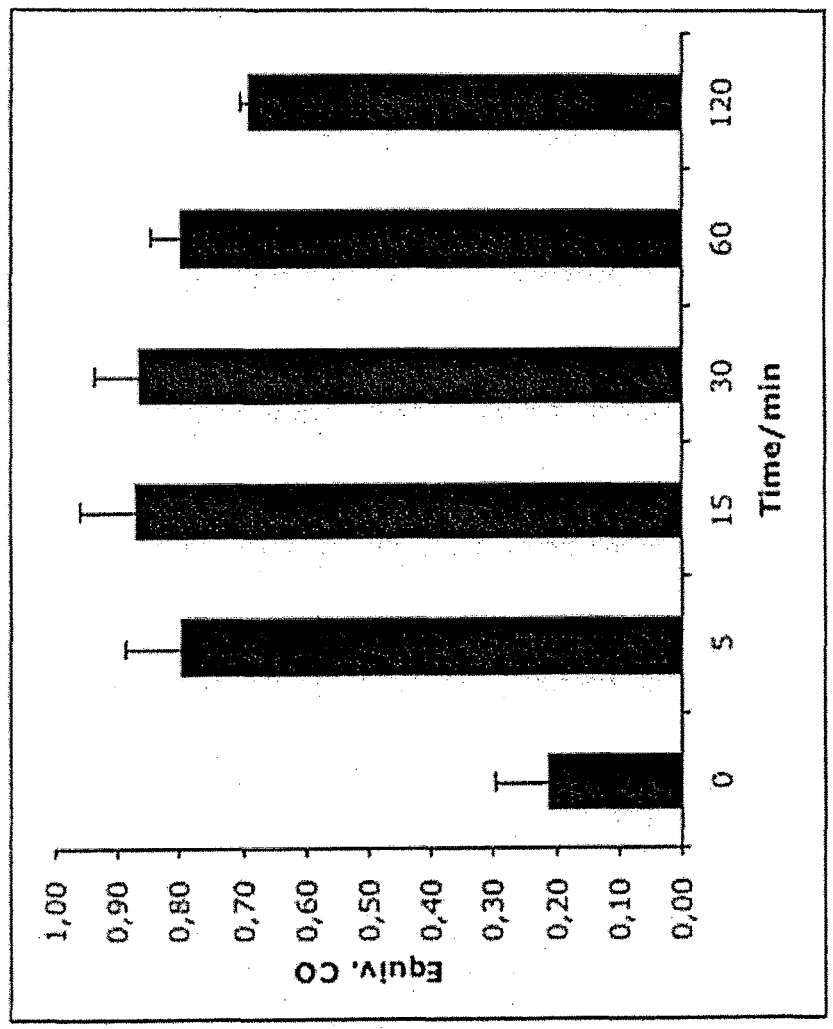
FIG. 10. Equivalents of CO transferred to deoxy-Mb by $RuCl_2(CO)_3$(methyl β-D-thiogalactopyranoside) (Compound 1). Average of 2 experiments performed in PBS7.4 with: [deoxy-Mb]=61 uM and [Compound 1]=51 uM; [deoxy-Mb]=68 uM and [Compound 1]=50 uM.

The Mb assay was performed as described in Clark et al., Circ. Res. (2003) 93:2-8. A stock solution of Myoglobin (Mb) from equine skeletal muscle was prepared by dissolving the protein in PBS7.4. From this solution aliquots were taken to a cuvette (final concentration between ca. 60 μM) and $Na_2S_2O_4$ in PBS, pH 7.4 (10 mg/mL solution; 0.1% final concentration) was added to convert met-Mb into deoxy-Mb. The reactions were done by mixing in the same cuvette and by this order, the Mb stock solution, the $Na_2S_2O_4$ solution, a calculated amount of a solution of Compound 1 and adding PBS to obtain the desired final volume. Before adding the Compound 1 solution a control spectrum was always acquired to see if the protein had been properly reduced with sodium dithionite. Two controls were done in duplicate, the negative control (0% CO-Mb), a deoxy-Mb solution and the positive control (100% CO-Mb), obtained by bubbling pure CO gas into the deoxy-Mb solution for 10-15 min. The experimental spectrum was fitted as a weighted sum of the deoxy-Mb and the CO-Mb spectra. Solver function in MS Excel was used to calculate the percentage of CO-Mb by deconvolution of the spectra using both positive and negative standards as controls. The absorbance spectrum was converted into a percentage of CO-Mb and the amount of CO liberated was calculated as molar equivalents of CO based on the initial concentration of Compound I (see FIG. 10).

Protein Mass Spectrometry

Liquid chromatography-mass spectrometry (LC-MS) was performed on a Micromass Quattro API instrument (ESI-TOF-MS) coupled to a Waters Alliance 2795 HPLC using a MassPREP On-Line Desalting Cartridge. Water:acetonitrile, 95:5 (solvent A) and acetonitrile (solvent B), with solvent A containing 0.1% formic acid, were used as the mobile phase at a flow rate of 0.3 mL min$^{-1}$. The gradient was programmed as follows: 95% A (0.5 min isocratic) to 80% B after 1.5 min then isocratic for 1 min. After 4 min to 95% A and then isocratic for 6 min. The electrospray source of LCT was operated with a capillary voltage of 3.0 kV and a cone voltage of 20 V. Nitrogen was used as the nebulizer and desolvation gas at a total flow of 600 L hr$^{-1}$. Proteins typically elute between 2 and 4 minutes using this method. Spectra were calibrated using a calibration curve constructed from a minimum of 17 matched peaks from the multiply charged ion series of equine myoglobin, which was also obtained at a cone voltage of 20 V. Total mass spectra were reconstructed from the ion series using the MaxEnt algorithm preinstalled on MassLynx software (v. 4.0 from Waters) according to manufacturer s instructions.

Lysozyme Binding Studies

Hen Egg White Lysozyme C (PDB code 3b61; UniProtKB/Swiss-Prot code P00698). The amino acid sequence of the egg white lysozyme employed is described in Canfield et al., *J. Biol. Chem.* (1963) 238:2698-2707 (1963). Quantitative determination of lysozyme-ligand binding in the solution and gas phases by electrospray ionisation mass spectrometry follows Veros et al., *Rapid Commun. Mass Spectrom.* (2007) 21:3505-3510). All manipulations were carried out at room temperature. Lyophilized lysozyme (2 mg, 0.14 mol) was dissolved in 1 mL of water in a 1.5 mL plastic tube. The sample was split into 150 µL aliquots (0.3 mg, 0.02 µmol) and stored at 4° C. A 50 µL aliquot was analyzed by LC-MS (calculated average isotopic mass of the egg white lysozyme=14305.1).

Figure 11A:
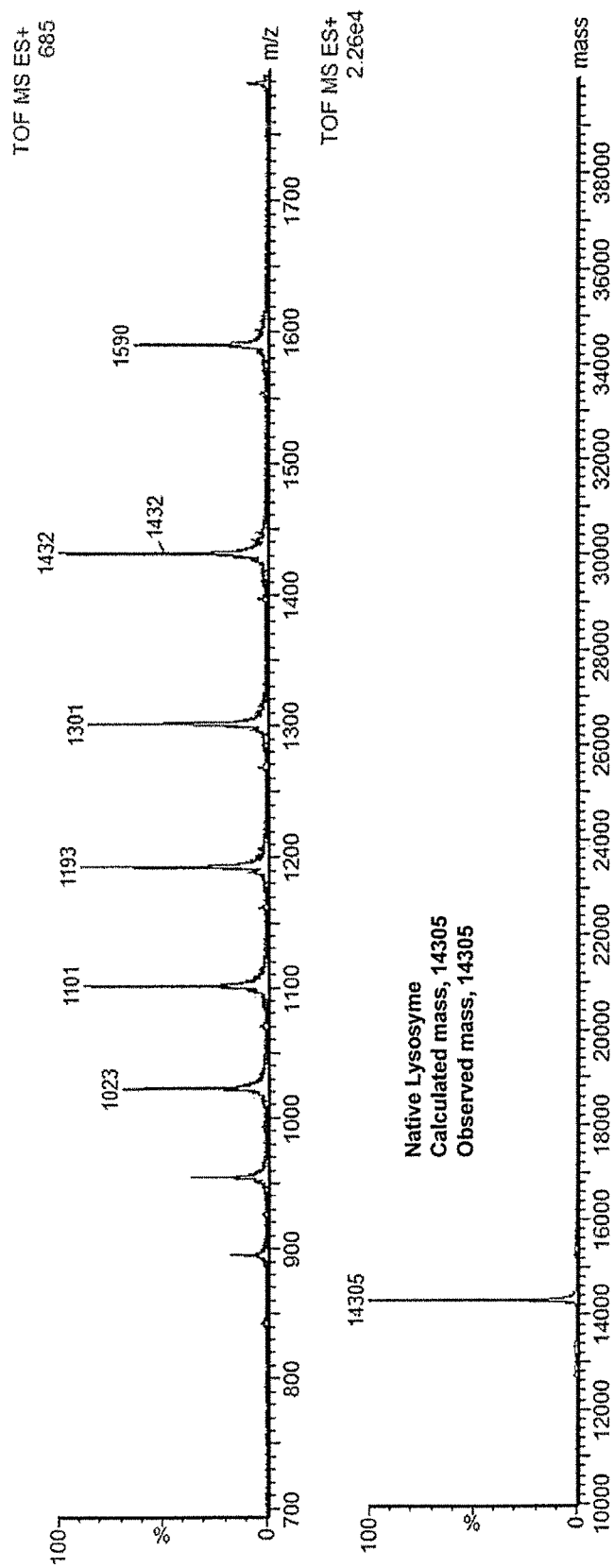
FIGS. 11*a*-11*e*.
Figure 11B:
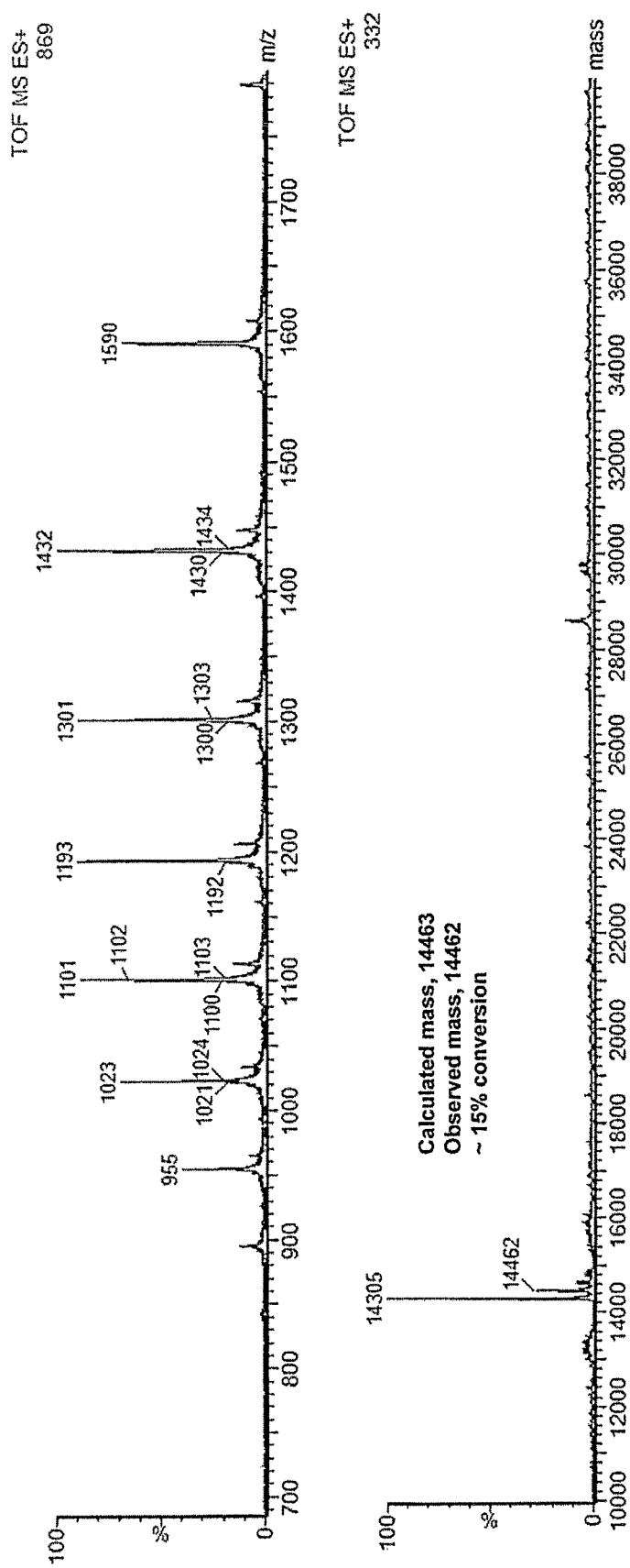
Figure 11C:
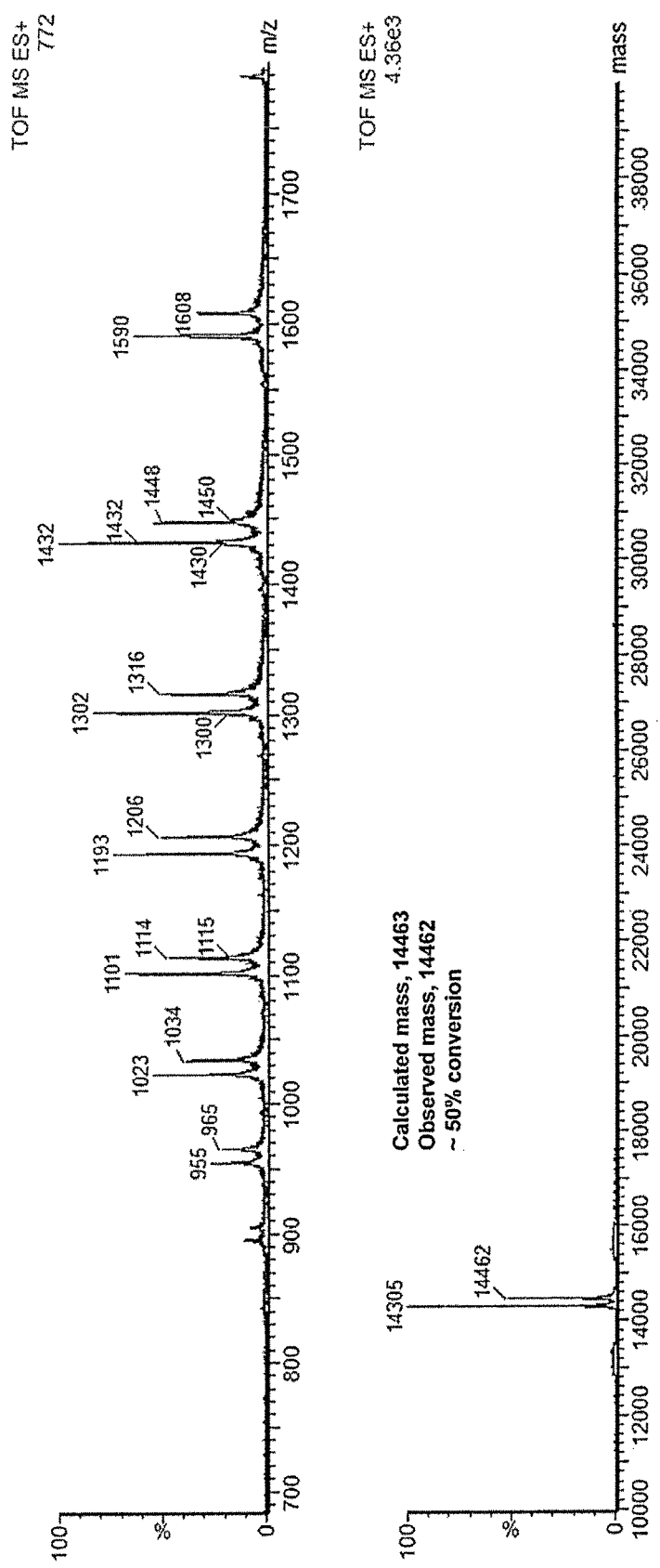
Figure 11D:
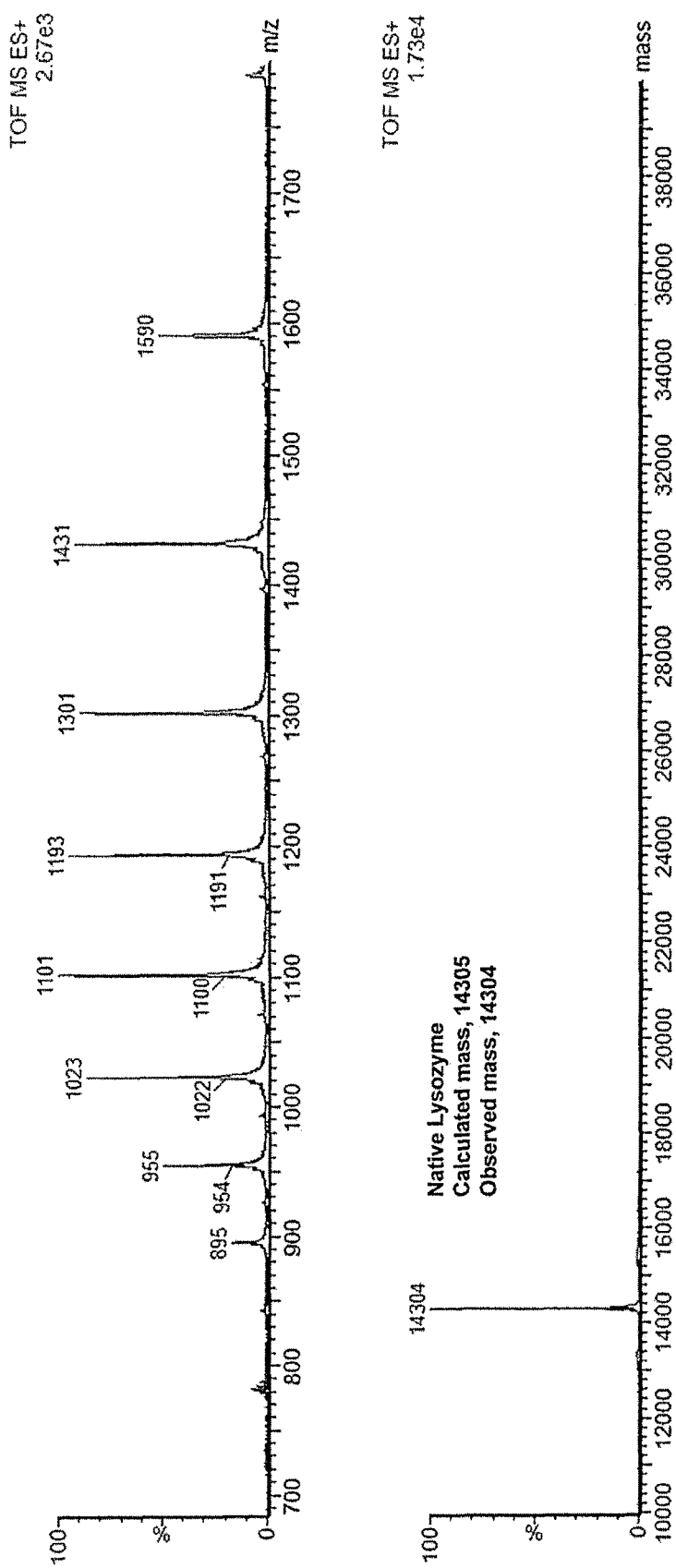
Figure 11E:
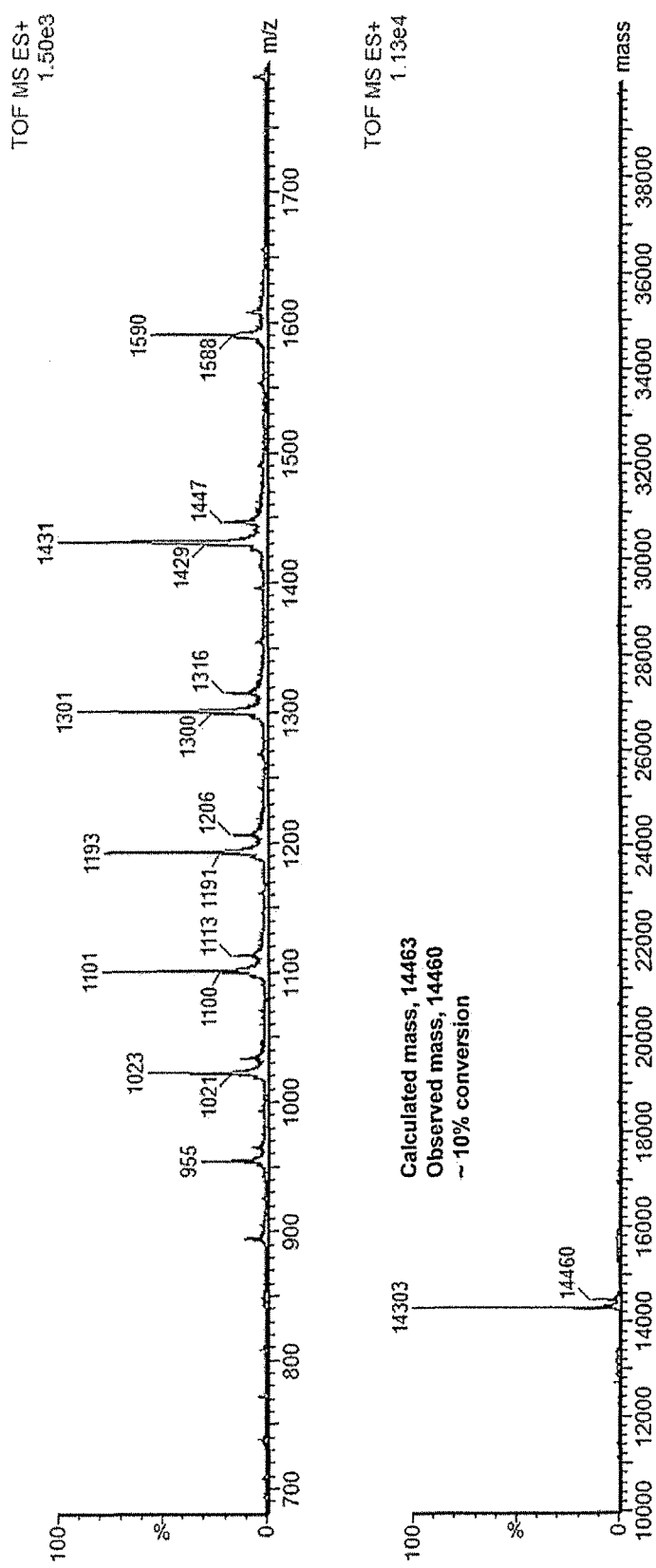

Santos-Silva and co-workers previously describe CORM-3's reactivity towards proteins and formation of a Ru(II) dicarbonyl-lysozyme complex (see, e.g., Santos-Silva et al., *J. Am. Chem. Soc.* (2011) 133:1192-1195). A solution of CORM-3 or Compound 1 (10 equivalents, 0.2 µmol) in water (50 µL) (at this concentration the pH of the solution containing CORM-3 is 3.0 and Compound 1 4.0) was added by micropipette to the lysozyme solution (150 µL) and the reaction mixture was vortexed periodically over 1 minute. The tube was left to shake for 1 hour. 50 µL aliquots were collected and analyzed by LC-MS over the reaction time (10 minutes and 1 hour). Two protein species were detected, one corresponding to the mass of native lysozyme (14305=calculated mass) and another corresponding to the addition of a Ru(CO)$_2$+ unit (m/z 157.9) to the mass of lysozyme (14463=calculated mass). After 1 hour, small molecules were removed from the reaction mixture by loading the sample onto a PD10 desalting column (GE Healthcare) previously equilibrated with 10 column volumes of deionized water and eluting with 3.50 mL of deionized water. The collected sample (now diluted to 0.57 mg/mL) was analyzed by LC-MS at ten minutes and 1 hour at room temperature, see, e.g., ESI-MS of lysozyme when incubated with CORM-3 at 10 minutes (FIG. 11b) and 1 hour (FIG. 11c) and ESI-MS of lysozyme when incubated with Compound 1 at 10 minutes (FIG. 11d) and 1 hour (FIG. 11e).

Preparation of Tricarbonyldichloro(Thiogalactopyranoside) Ruthenium(II) (Compound 1)

Dichlorotricarbonylruthenium (II) dimer (0.52 g, 1.02 mmol) was dissolved in anhydrous methanol (30 mL) and transferred via cannula to a solution of β-D-thiogalactopyranoside (0.42 g, 2.04 mmol) in anhydrous methanol (30 mL). A slightly pale yellow clear solution was formed and stirred for 24 hours at room temperature under nitrogen atmosphere. The solution was concentrated and diethyl ether was added. The white precipitate was filtered, washed with diethyl ether (3×30 mL), and dried. The residue was partially dissolved in diethyl ether and frozen in liquid nitrogen. The solid was crushed and stirred. A white powder formed and was filtered and dried to give tricarbonylchloro(thiogalactopyranoside) ruthenium(II) (348 mg, 73%); the compound was stored under nitrogen; $\nu_{max}$ (KBr disc cm$^{-1}$) 2139 (s, C=O) 2060 (s, C=O) cm$^{-1}$; $\delta_H$ (400 MHz, D$_2$O) 2.23 (3H, s, CH$_3$), 3.58-75 (6H, m), 4.38 (1H, d, J 9.2 Hz, H-1); Found: C, 25.81%; H, 2.94%, S,6.80%. C$_{10}$H$_{14}$Cl$_2$O$_8$RuS Requires: C, 25.76%; H, 3.03%; S, 6.88%.

OTHER EMBODIMENTS

This application refers to various issued patents, published patent applications, journal articles, books, manuals, and other publications, all of which are incorporated herein by reference.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A pharmaceutical composition comprising,

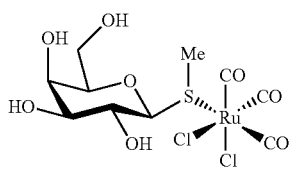

or a salt, isomer, hydrate, or solvate thereof, or combination thereof, and a pharmaceutically acceptable excipient.

2. A method of treating a malaria infection comprising administering an effective amount of the pharmaceutical composition of claim 1, to a subject in need thereof.

3. The method of claim 2, wherein the malaria infection is severe malaria due to a *Plasmodium* infection.

4. The method of claim 3, wherein the *Plasmodium* infection is a *Plasmodium falciparum* infection or a *Plasmodium vivax* infection.

5. The method of claim 2, wherein the malaria infection is cerebral malaria (CM).

6. The method of claim 2, wherein the malaria infection is pregnancy-associated malaria (PAM).

7. The method of claim 2, wherein the method further comprises administering one or more additional agents.

8. The method of claim 7, wherein the one or more additional agents is selected from the group consisting of quinazolines, protein kinase inhibitors, quinines, tetracyclines, aminoquinolones, biquanides, cinchona alkaloids, sulfonamides, artemisinins, clindamycin, dapsone, atovaquone, lumefantrine, piperaquine, pyronaridine, atovaquone, mefloquine, pyrimethamine, halofantrine, TNF inhibitors, iron chelators, dichloroacetate, dexamethasone, intravenous immunoglobulin, curdlan sulfate, and salts thereof; CO gas, and combinations thereof.

9. The method of claim 8, wherein the one or more additional agents is artesunate.

10. The method of claim 8, wherein the one or more additional agents is CO gas.

11. The method of claim 8, wherein the one or more additional agents is a TNF inhibitor.

12. The method of claim 8, wherein the one or more additional agents is an iron chelator.

13. The method of claim 8, wherein the one or more additional agents is dichloroacetate.

14. The method of claim 7, wherein the one or more additional agents is an anti-inflammatory agent.

15. A method of treating acute lung injury comprising administering an effective amount of the pharmaceutical composition of claim 1, to a subject in need thereof.

16. The method of claim 15, wherein the acute lung injury is malaria-associated acute lung injury.

17. A method of treating acute respiratory distress syndrome comprising administering an effective amount of the pharmaceutical composition of claim 1, to a subject in need thereof.

18. The method of claim 17 wherein the acute respiratory distress syndrome is malaria-associated acute respiratory distress syndrome.

* * * * *